US006906050B2

(12) United States Patent
Robinson

(10) Patent No.: US 6,906,050 B2
(45) Date of Patent: Jun. 14, 2005

(54) SUBSTITUTED PORPHYRIN AND AZAPORPHYRIN DERIVATIVES AND THEIR USE IN PHOTODYNAMIC THERAPY, RADIOIMAGING AND MRI DIAGNOSIS

(75) Inventor: Byron C. Robinson, Santa Barbara, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 66 days.

(21) Appl. No.: 10/159,580

(22) Filed: May 31, 2002

(65) Prior Publication Data

US 2003/0100752 A1 May 29, 2003

Related U.S. Application Data

(60) Provisional application No. 60/295,343, filed on May 31, 2001.

(51) Int. Cl.[7] ..................... A61K 31/33; A61K 31/555; A61K 31/695; C07D 487/22
(52) U.S. Cl. .................. 514/183; 514/185; 514/63; 514/189; 514/740; 540/121; 540/145
(58) Field of Search ................. 514/183, 185, 514/63, 189, 740; 540/121, 145

(56) References Cited

U.S. PATENT DOCUMENTS

| | | | |
|---|---|---|---|
| 4,647,447 A | 3/1987 | Gries et al. | 424/9 |
| 4,882,234 A | 11/1989 | Lai et al. | 514/185 |
| 4,885,363 A | 12/1989 | Tweedle et al. | 540/465 |
| 4,996,312 A | 2/1991 | Sakata et al. | 540/145 |
| 5,053,503 A | 10/1991 | Dean et al. | 540/474 |
| 5,275,801 A | 1/1994 | Niedballa et al. | 424/1.65 |
| 5,277,895 A | 1/1994 | Platzek et al. | 424/9 |
| 5,364,614 A | 11/1994 | Platzek et al. | 424/9 |
| 5,633,275 A | 5/1997 | Mori et al. | 514/410 |
| 5,654,423 A | 8/1997 | Kahl et al. | 540/145 |
| 5,675,001 A | 10/1997 | Hoffman et al. | 540/121 |
| 5,676,923 A | 10/1997 | Platzek et al. | 424/4 |
| 5,703,230 A | 12/1997 | Boyle et al. | 540/145 |
| 5,705,622 A | 1/1998 | McCapra | 536/23.1 |
| 5,730,956 A | 3/1998 | Platzek et al. | 424/9.36 |
| 5,849,259 A | 12/1998 | Hilger et al. | 424/1.65 |
| 6,136,841 A | 10/2000 | Platzek et al. | 514/410 |
| 6,251,367 B1 | 6/2001 | Platzek et al. | 424/9.362 |

FOREIGN PATENT DOCUMENTS

| | | | |
|---|---|---|---|
| CA | 1341176 | 1/2001 | C07D/257/02 |
| EP | 0 220 686 A2 | 10/1986 | C07D/487/22 |
| EP | 0 232 751 B1 | 9/1991 | C07D/273/00 |
| EP | 0 811 626 A1 | 12/1997 | C07D/487/22 |
| WO | WO 92/06097 | 4/1992 | C07D/487/22 |
| WO | WO 96/01655 | 1/1996 | A61K/49/00 |
| WO | WO 96/02669 | 2/1996 | C12Q/1/68 |
| WO | WO 97/20846 | 6/1997 | C07D/487/22 |
| WO | WO 99/62512 | 12/1999 | A61K/31/40 |
| WO | WO 00/05235 | 2/2000 | C07D/487/22 |
| ZA | 937194 | 9/1993 | |

OTHER PUBLICATIONS

Chemical Abstract DN 103:188202, also cited as Seria Flzyka, 255–8(1985).*
Chemical Abstract DN 87:53240, also cited as Justus Lieb. Annal. 3, 339–59(1977).*
Chemical Abstract DN 81:113159, also cited as Zhurnal Prikladnoli Spek. 21/1,73–81(1974).*
Chemical Abstract DN 73:30379, also cited as Izvestiya Akademil Nauk SSSR, 34/3,620–4(1970).*
PubMed Abstract 8040757, also cited as J. Photochem. Photobiol B. 23/2–3,239–43(1994).*
PubMed Abstract 12114873, also cited as Q. J. Nucl. Med. 46/2,105–12(2002).*
PubMed Abstract 15073860, also cited as Cancer, 100/8, 1705–11(2004).*
PubMed Abstract 12844192, also cited as Natl. Toxicol. Program. Tech Rep. Ser. Jan. 6, 1–203(1997).*
Dzilinski et al Chemical Abstract DN 103:188202 also cited as Seria Fizyka, 255–8(1985).*
Furhop et al Chemical Abstract DN 87:53240 also cited as Justug Liebigs Ann. der Chem.3,339–59(1977).*
Masshenkov et al, Chemical Abstract DN 81:113159, also cited as Zhurnal Prik. Spektr. 21/1,73–81(1974).*
Gurinovitch et al, Chemical Abstract DN 73:30379, also cited as Izuestiya Akademii Nauk SSSR 34/2,620–4(1970).*
David Kessel, et al., *Tumor–localizing Components of the Porphyrin Preparation Hematoporphyrin*, 43 Cancer Research 1994–1999 (1983).
David R. Sanderson, et al., *Hematoporphyrin As A Diagnostic Tool*, 30 Cancer 1368–1372 (1972).
Frederick R. Longo, et al., *Kinetic and Mechanistic Studies of Metalloporphyrin Formation*, The Porphyrins, V Academic Press 459 (1980).
H. Fischer et al., Z. Physiol. Chem., 201–219 (1936).
James Winkelmann, et al., *The Concentration in Tumor and Other Tissues of Parenterally Administered Tritium– and [14]C–labeld Tetraphenyloporphinesulfonate[1]*, 27 Cancer Research 2060–2064 (1967).
Kark M. Kadish, et al., *Synthesis and Organic Chemistry*, The Porphyrin Handbook, Table of Contents, I Academic Press, Chapters 1–3 (2000).
Kevin M. Smith, *Porphyrins and Metalloporphyrins*, Elsevier (1975).
N.J. Patronas, et al., *Metalloporphyrin Contrast Agents for Magnetic Resonance Imaging of Human Tumors in Mice*, 70 Cancer Treatment Reports 391–395 (1986).

(Continued)

Primary Examiner—Richard L. Raymond
Assistant Examiner—Sudhaker B. Patel
(74) Attorney, Agent, or Firm—Finnegan, Henderson, Farabow, Garrett & Dunner, L.L.P.

(57) ABSTRACT

Substituted porphyrin and azaporphyrin deviations with various substitutents in the 12- and 17-positions of the porphyrin skeleton as pharmaceutical agents for use in photodynamic therapy, MRI diagnosis, and radiodiagnostics.

30 Claims, No Drawings

OTHER PUBLICATIONS

Nagao Kobayashi, *meso–Azaporphyrins and Their Analogues*, The Porphyrin Handbook, 2 Academic Press 301–360 (2000).

P. Hambright, et al., *The Distribution of Various Water Soluble Radioactive Metalloporphyrins in Tumor Bearing Mice*, 5 Bioinorganic Chemistry 87–92 (1975).

Richard L. Lipson, et. al., *Hematoporphyrin Derivative For Detection And Management of Cancer*, 20 Cancer 2250–2257 (1967).

S. Nakajima, et al., *Tumor Imaging with[$^{111}$In]Mono–DTPA ethyleneglycol–Ga–Deuteroporphyrin*, 46 Photochemistry and Photobiology 783–788 (1987).

Saburo Neya, et al., *Remarkable Functional Aspects of Myoglobin Induced by Diazaheme Prosthetic Group*, 121 The Journal of Biochemistry 654–660 (1997).

Theodora W. Greene, et al., *Protective Groups in Organic Synthesis*, Table of Contents (1991).

\* cited by examiner

SUBSTITUTED PORPHYRIN AND AZAPORPHYRIN DERIVATIVES AND THEIR USE IN PHOTODYNAMIC THERAPY, RADIOIMAGING AND MRI DIAGNOSIS

This application claims the benefit of Provisional application Ser. No. 60/295,343, filed May 31, 2001.

FIELD OF THE INVENTION

This invention is directed to substituted porphyrin and azaporphyrin derivatives with various substituents in the 13- and 17-positions of the porphyrin skeleton suitable as pharmaceutical agents for use in photodynamic therapy, MRI diagnosis, and radiodiagnostics. The invention is also directed to pharmaceutical agents that contain these compounds, as well as a process for the production of these compounds and agents.

BACKGROUND OF THE INVENTION

Photodynamic therapy ("PDT") is a new modality for the treatment of malignancies, diseased tissue, hyperproliferating tissues, pathogens or unwanted normal tissues. PDT involves a localized or systemic administration of a photosensitizing compound followed by exposure of target tissue to photoactivating light. The photoactivating light excites the photosensitizer which, in turn, interacts with singlet oxygen causing the production of cytotoxic oxygen species. The interaction of the cytotoxic oxygen species with tissues in which the photosensitizer is localized causes a modification of the tissue, resulting in a desired clinical effect. The tissue specificity of the resultant phototoxic damage is determined largely, although not entirely, by the relative concentrations of the photosensitizer in each tissue at the time of its exposure to the photoactivating light.

Following systemic administration, many photosensitizers accumulate to varying degrees within tissues depending on the pharmacokinetic and distribution profile of the photosensitizing compound and the cell types comprising the tissues. The chemical factors that enable certain photosensitizers to accumulate to a greater degree at a target site than other photosensitizers is not well understood. Indeed, the biological factors that result in the preferential uptake of some photosensitizers in certain tissue types compared to other tissue types are not well understood either. It is clear, however, that each photosensitizer has its own distribution and pharmacokinetic properties within different tissues and these properties determine the relative usefulness of the photosensitizer for the desired therapy. Currently, rigorous screening and biological evaluation in appropriate model systems is required to identify suitable photosensitizers that display the characteristics necessary to effect a therapy within the diseased or target tissues.

Porphyrins and azaporphyrins and their metallated derivatives belong to a family of substances that are suitable for PDT. These compounds accumulate in target tissues and absorb light in a range in which living tissue is still fairly permeable, namely between 380–680 nm. Moreover, porphyrins, azaporphyrins and their photoactive metallated derivatives exhibit high yields of the excited triplet state, a long lifetime in this state, and good energy transfer to oxygen with concomittant production of singlet oxygen. Of the porphyrins and their derivatives, several photosensitizers have been developed largely for use in oncological applications, but have also been examined in other disease areas in the PDT field in humans. (WO 92/06097; WO 97/20846; EP 0 811626; U.S. Pat. Nos. 5,633,275, 5,654, 423, 5,675,001, 5,703,230, and 5,705,622). Such photosensitizers include Photofrin (U.S. Pat. No. 4,882,234), 5-aminolevulinic acid (protoporphyrin IX precursor), SnET2, Visudyne® (Benzoporphyrin derivative), Antrin®, Optrin® (Lutetium texaphyrin) and mono-aspartyl chlorin e6 (MACE). All of these compounds were designed specifically for the treatment of solid tumors. Specifically, many of these compounds were designed to have large absorptions in the 620–740 nm range so as to optimize the photoactivation of the drug with a wavelength that will penetrate to the greatest depths possible all tissue types. In particular, these drugs were designed to absorb outside of the blood absorption profile, thus ensuring efficient photoactivation in most tissue types.

The excitation light source (usually diode lasers or dye lasers) has historically been matched to the far-red absorption bandwidth of the photosensitizer in order to maximize light penetration through tissues. Indeed, the present inventor believes that all the tetrapyrrolic photosensitizers used have been designed for long wavelength absorption of light (>630 nm) to address this perceived issue. Surprisingly, it has been found that short wavelength photosensitizers (with activation absorptions<600 nm) are capable of delivering effective localized therapy to many disease indications where historically long wavelength photosensitizers (with activation absorptions>600 nm) have shown ineffective clinical outcomes. One such example is in coronary artery disease.

While several of the photosensitizers described above have been used to treat atheromatous plaques and some are able to display some inhibition of intimal hyperplasia in animal models, many if not all have characteristics that will limit the usefulness of these drugs in a clinical setting. One particular concern is the half-life of the photosensitizer. A photosensitizer delivered systemically with a long half-life (CASPC, Photofrin, SnET2) may have phototoxic side effects if exposed to direct light, within days of the procedure.

A second even more pressing concern that has to date escaped many of the investigators testing new photosensitizers in cardiovascular disease is photochemically induced damage to "normal" myocardial tissue surrounding the artery due to non-selective photosensitizer uptake and long depths of light penetration, which activates the photosensitizer in the myocardial tissue. Historically, it has been believed that attenuation of the photosensitizer excitation light by blood would inhibit the use of wavelengths of light shorter than 600 nm in the cardiovascular field. This may have been true several years ago when balloon catheter technology in PDT was not as advanced as it is today. New endovascular light ballon catheters, however, can remove most of the blood from the treatment area. This advance enables the use of short wavelengths of light that historically may have been attenuated by blood.

The use of wavelengths of light lower than 600 nm offers significant advantages in PDT because such wavelengths have penetration characteristics that deliver the PDT effect to the target sites (media and adventicia layers of the vessel) and not to myocardial tissue. Thus, effective therapy can be afforded at the target site, while deeper tissues are shielded from a PDT response by blood absorption within these tissues. Previously reported cardiovascular experiments performed to date on tetrapyrrolic molecules have been done at wavelengths>620 nm. Experiments that we have performed in pig arteries with new photosensitizer candidates at light activation>600 nm have resulted in unacceptable levels of damage to myocardial or cardiac muscle tissue surrounding the treatment area. This has major clinical implications to patients with existing ischemic myocardial or muscle tissue due to poor artery perfusion. Attempts to lower the light dosimetry in order to limit treatments to the target tissue (media/intima) leads to long treatment times and less efficacy. In addition, long treatment times in the artery exposes the patient to additional risks with inflation and deflation of the balloon devices. Importantly, we have demonstrated in pig arteries that effective treatment depths can be obtained with shorter wavelengths of light, with sparing of underlying tissue damage.

Thus, it is believed that, long wavelength absorbing molecules (>600 nm), unless highly selective to target myocardial and intimal tissues (which has not to date been reported with any photosensitizer in cardiovascular tissues), may cause unacceptable normal cardiac tissue damage. Therefore, it would appear that activation of lutetium texaphyrin, BPD-MA, MACE, CASPc, SnET2, and pheophorbide PH-II26 with red light may be of limited use in the treatment of cardiovascular disease as all of these compounds are "red" absorbers by design, in so much as all possess low energy absorbtion peaks at wavelengths>600 nm. It should be noted also that chlorins, phthalocyanines and texaphyrin type photosensitizers in general have little absorption in the 500–600 nm regions, and thus may be suboptimal with regard to light activation at green and yellow wavelengths in cardiovascular tissues. In addition, protoporphyrin IX and photofrin do not display absorption maximas at 532 nm, thus they may be inefficient at absorbing treatment light at this wavelength and have very low molar extinction coefficients at 575 nm (~7000 $cm^{-1}/M^{-1}$). Furthermore, because long wavelength photosensitizers by design have red absorption peaks, operating room lighting in an emergency situation may cause serious photosensitivity in light exposed tissues. Attempts to use red light filters on operating room lights results in poor tissue contrast and sub-optimal lighting conditions, making surgical procedures under these conditions extremely difficult, if not impossible. Optical clarity is much better at shorter wavelengths (500–600 nm) where the depth of light peneration is limited to a few mm of tissue penetration during the surgical procedure.

Another significant drawback of the above long wavelength absorbing compounds mentioned is that they are only suitable for therapy; prior or simultaneous MRI-diagnostic monitoring of the success of the therapy is not possible with them, nor is radiodiagnostic imaging. For this purpose, it is necessary to administer another paramagnetic substance, which must have a biodistribution that is as close to that of the therapeutic agent as possible. This requirement often cannot be met.

There have been attempts by groups in the field to provide porphyrin linked MRI or radiodiagnostic compounds. Notable examples include: Hilgar, C. S., et al, U.S. Pat. No. 5,849,259; Niedballa, U., et. al., U.S. Pat. No. 5,275,801; Platzek, J., et. al., U.S. Pat. No. 6,136,841; Niedballa, U., et. al., EP 0355041 A2, A3, and B1; Sakata, I., et. al., U.S. Pat. No. 4,996,312; Sakata, I., et. al., U.S. Pat. No. 4,996,312; and Sakata, I., et. al., U.S. Patent No. EP 0220686. It has been known for some time that porphyrin derivatives selectively accumulate in human and animal tumors (D. Kessel and T.-II. Chu, Cancer Res. 43, pp. 1994–1999, 1983; P. Hambright, Bioinorg. Chem. 5, pp. 87–92,1975; R. Lipson et al., Cancer 20, pp. 2250–2257, 1967; and D. Sanderson et al., Cancer 30, pp. 1368–1372, 1972). First attempts to use this class of compound as a diagnostic agent were also described in the literature (J. Winkelmann et al., Cancer Research 27, pp. 2060–2064, 1967; N. J. Patronas et al, Cancer Treatment Reports 70, pp. 391–395, 1986). However, the compounds so far described are far from being able to satisfactorily meet the desired requirements to be effective PDT, MRI and radiodiagnostic imaging agents.

Substituted hematoporphyrin complex compounds used in diagnosis and treatment are described in patent application EP 0 355 041. While these compounds show a good concentration behavior in various target organs, the described compounds used as NMR diagnostic agents are not satisfacatory because they require a dose necessary for optimal imaging that is too close to the lethal dose. Hematoporphyrin derivatives have the drawback that they can eliminate both pseudobenzylic OH groups in the hydroxyethyl side chains.

Derivatives of the deuteroporphyrin have been proposed (Sakata, et al., U.S. Pat. No. 4,996,312 and EP 0220686) for tumor imaging with radioisotopes, containing as additional complexing groups polyaminopolycarboxylic acids bound to the porphyrin skeleton by ethylene glycol bridges (Photochemistry and Photobiology Vol. 46, pp. 783–788 (1987)). However, such porphyrin esters are not very suitable for parenteral use in patients, especially for NMR or radiodiagnostic diagnosis, since the injection solutions obtained from them can neither be heat-sterilized nor stored for a sufficiently long time.

Other derivatives of deuteroporphyrins have been proposed in Hilgar, C. S., et al. U.S. Pat. No. 5,849,259; Niedballa, U., et. al., U.S. Pat. No. 5,275,801; Platzek, J., et. al. U.S. Pat. No. 6,136,841; and Niedballa, U., et. al., EP 0355041 A2, A3, B1 with striking similarity to overcome certain deficiencies of Sakata's deuteroporphyrins by providing metalloporphyrin amide linkages. However, all of these approaches using deuteroporphyrins are suboptimal with respect to design of short wavelength PDT photosensitizers for use as MRI or radiodiagnostic agents for reasons detailed below.

Sakata's porphyrin-based PDT/MRI/radiodiagnostic compounds are based on a naturally occurring asymmetrical porphyrin ring system shown in FIG. 1.

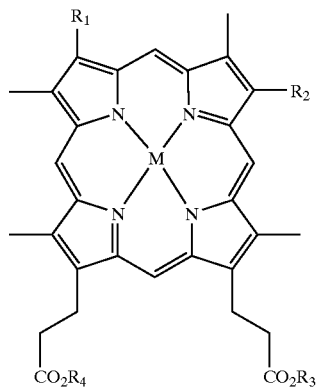

FIG. 1

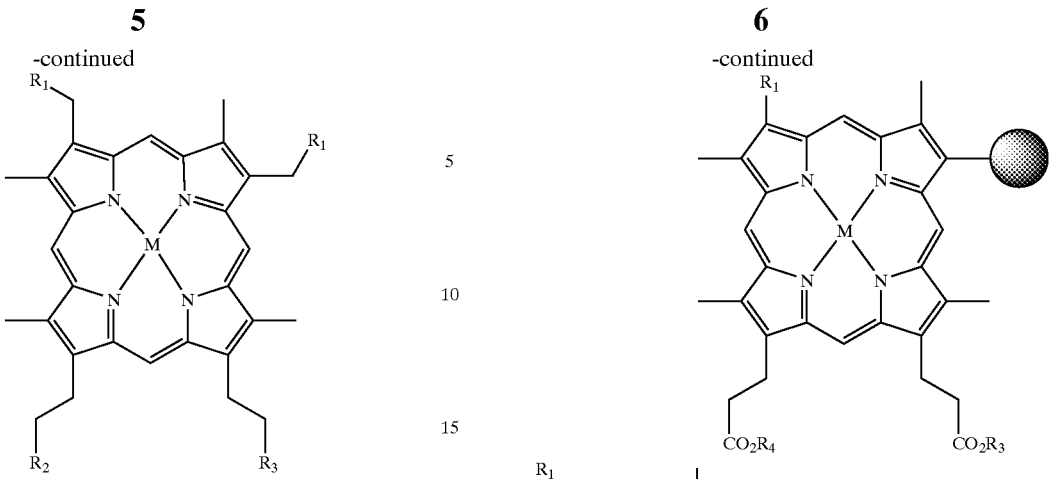

In his synthetic philosophy, Sakata has linked polyfunctional carboxyl groups that are capable of binding radioactive metals or MRI active metals to a) the $R_1$ and $R_2$ positions as shown via ether—alcohol linkages; and b) to positions $R_4$ or $R_5$ via ether linking units. This synthetic approach carries with it significant manufacturing problems. First, the linking of one metal chelating moiety to an asymmetrical porphyrin at $R_1$ or $R_2$, $R_3$ or $R_4$ (where $R_1$ and $R_2$ can be vinyl, ethyl, —CH(O-lower alkanoyl)$CH_3$, —CH(OR)$CH_3$ or —CH(O-loweralklene-OR)$CH_3$,) generates at least two new chemical porphyrinic entities in the synthesis process if $R_1$ and $R_2$ (or $R_3$ and $R_4$) are the same linking moiety. This is outlined in scheme 1.

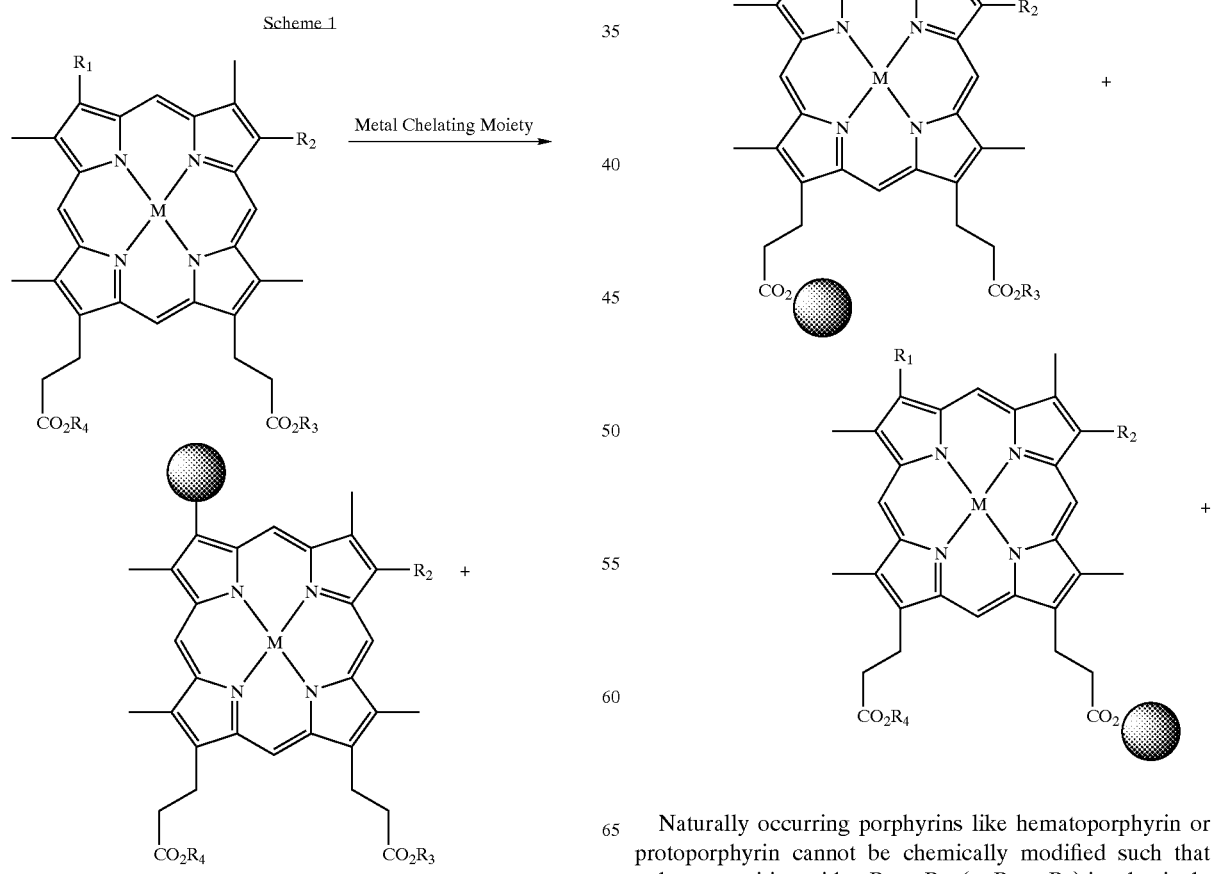

Scheme 1

Naturally occurring porphyrins like hematoporphyrin or protoporphyrin cannot be chemically modified such that only one position, either $R_1$ or $R_2$, (or $R_3$ or $R_4$) is selectively modified to form a molecule with a single linking unit as the only product. In this instance, two compounds are always formed which must be separated to obtain a pure single molecule with which to link the metal chelating moiety. The separation of the two porphyrins is often difficult (if not impossible) and complicates both the manufacturing process and the cost of the final product. If one chooses not to separate the isomers, the isomeric components will each have their own toxicities, and pharmacokinetic and distribution profiles. If one of the isomers is not optimal therapeutically due to any one of these parameters, then the route to regulatory approval is often more complex, time consuming and costly than pursuing a single defined isomer. A second limiting factor that has been highlighted previously, is the instability of the various linking groups to aqueous hydrolysis, elimination at sterilization temperatures, or prolonged storage in solution. Additionally, the use of diastereotopic mixtures as occurs with —CH(OR)CH$_3$ groups in porphyrins complicates the analysis of the molecules for development.

Niedballa and Platzek's approach also has the same synthetic manufacturing problems as explained for Sakata (except when R$_1$=H), i.e., multiple compounds are produced when a single linking moiety is attached to the molecule. These molecules may offer enhanced stability over Sakata's due to the use of amine linkages. The limitation of R$_1$=H symmetry does not, however, allow for modification of this molecule with other functionality that may enhance localization or uptake in tissues or target organelle, or changes in pharmacokinetic or elimination profiles for singly linked molecules. Compounds with high water solubility are often not taken up efficiently by tumors or cells. The ability to enhance the lipophilicity of the molecule is thus very important.

An additional problem, that has been overlooked by all of the prior workers (Sakata, Niedballa, and Platzek) in the development of short wavelength porphyrin photosensitizers, is the limited absortion profile of the porphyrin ring system metallated tetrapyrroles. In general, metallotetrapyrroles have green and yellow absorptions at about 532 and 575 nm with molar extinction coefficients of between 15,000–20,000 M$^{-1}$ cm$^{-1}$. In the field of photodynamic therapy, the depth of light penetration into tissues is a function of the wavelength of the exciting light. The theoretical efficacy of a photosensitizer largely correlates to the molar extinction coefficient of the photosensitizer's absorption peak and its ability to absorb light. This is due primarily to the fact that the ability of a photosensitizer to absorb incidental light is a function of the cross sectional area of the molecule's absorption profile. Hence, photosensitizers with low molar extinction coefficients capture photons less efficiently than molecules with high molar extinction coefficients and are thus less efficient.

Therefore, there remains a need for novel photosensitizers that are easily manufactured, have excellent stability and solubility, and have more favorable wavelength absorption characteristics. There is a further need for photosensitizers that are capable of being modified to contain a wide range of substituents making biological targeting more possible and ultimately enabling control of the properties and uses of the compounds clinically for not only MRI and radiodiagnostic imaging, but also for treatment using photodynamic therapy.

The present inventor has found novel metal-free or metallated functionalized phototherapeutic agents that may be used for imaging (MRI or radiodiagnostic) before or after photodynamic therapy. These novel phototherapeutic agents are based on tetrapyrrolic ring systems such as the porphyrins and azaporphyrins that can be covalently linked by stable linkages to metal complexing agents. These new photosensitizers are useful in short wavelength applications in photodynamic therapy.

SUMMARY OF THE INVENTION

To achieve these and other advantages, and in accordance with the purpose of the invention as embodied and broadly described herein, the present invention in one aspect provides phototherapeutic compositions of metallotetrapyrrolic compounds of formula I which may be used as MRI, radiodiagnostic and PDT agents:

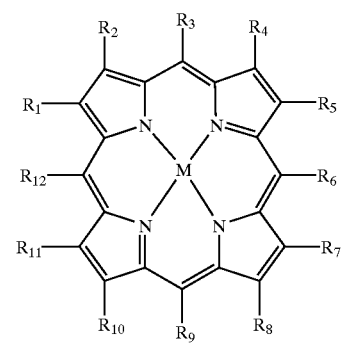

In formula I, $R_1$–$R_{12}$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, N(alkyl)$_2$, N(aryl)$_2$, CH=CH(aryl), CH=CHCH$_2$N(CH$_3$)$_2$, or a functional group of molecular weight of less than about 100,000 daltons; CH=CHCH$_2$N$^+$(CH$_3$)$_3$A, CH=N(alkyl)$_2$A, or N(alkyl)$_3$$^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, CH(CH$_3$)O-aryl;

(CH$_2$)$_n$O-alkoxy, or (CH$_2$)$_n$O-alkyl, where n is an integer from 0 to 8;

C(X)$_2$C(X)$_3$, where X is a halogen;

CO$_2$R$_{13}$, where R$_{13}$ is selected from H, a physiologically acceptable counter ion, a C1–C20 straight or branched chain alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons;

(CH$_2$)$_n$OH, or (CH$_2$)$_n$OR$_{14}$, where R$_{14}$ is selected from alkyl, haloalkyl, heteroalkyl, haloheteroalkyl, aryl, heteroaryl, heterocycle, a protecting group, a mono-, di-, or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_{15}$, (CHX)$_n$CO$_2$R$_{15}$, or (CX$_2$)$_n$CO$_2$R$_{15}$, where X is a halogen and R$_{15}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons, and n is an integer between 1 and 4;

$CONH(R_{16})$, $CONHNH(R_{16})$, $CO(R_{16})$, $CON(R_{16})_2$, $CON(R_{16})(R_{17})$, $(CH_2)_nCONH(R_{16})$, $(CH_2)_nCON(R_{16})_2$, $(CH_2)_nCOR_{16}$, $(CH_2)_nCON(R_{16})(R_{17})$, $(CX_2)_nCONH(R_{16})$, $(CX_2)_nCON(R_{16})_2$, $(CX_2)_nCON(R_{16})(R_{17})$, $(CX_2)_nCOR_{16}$, $(CH_2)_nCONHNH(R_{16})$, $(CX_2)_nCONHNH(R_{16})$, $(CHX)_nCONH(R_{16})$, $(CHX)_nCONHNH(R_{16})$, $(CHX)_nCO(R_{16})$, $(CHX)_nCON(R_{16})_2$, or $(CHX)_nCON(R_{16})(R_{17})$, where X is a halogen and $R_{16}$ and $R_{17}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{18})$, $(CH_2)_nS(R_{18})$, $(CH_2)_nNH(R_{18})$, $(CH_2)_nNHNH(R_{18})$, $(CH_2)_nN(R_{18})_2$, $(CH_2)_nN(R_{18})(R_{19})$, or $(CH_2)_nN(R_{18})(R_{19})(R_{20})^+A$, where $R_{18}$, $R_{19}$ and $R_{20}$ can be the same or different and are selected from H, $NH_2$, straight or branched chain C1–C20 alkyl, haloalkyl, heteroalkyl, haloheteroalkyl, aryl, heteroaryl, heterocycle, amino acids (provided —$NH(R_{18})$ is part of the amino acid), a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{18}$, $R_{19}$ and $R_{20}$ possess the atoms necessary to constitute an aromatic ring system, n is an integer between 0 and 4, and A is a physiologically acceptable counter ion;

$(CH_2)_nOPO_2OR_{21}$, or $(CH_2)_nPO(OR_{21})_2$, $(CH_2)_nPO_2R_{21}$, $(CH_2)_nPOR_{21}$ where $R_{21}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{22}$, or $(CH_2)_nNHNHCOR_{22}$, where $R_{22}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{23}$, $SO_2NHR_{23}$, $SO_2N(R_{23})_2$, $SO_2NHNHR_{23}$, or $SO_2R_{23}$, where $R_{23}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{23}$ can also be an amino acid, an amino acid salt, an amino acid ester residue, an amino acid amide residue, and n is an integer between 0 and 4;

aryl or substituted aryl, which may optionally bear one or more substituents with a molecular weight less than or equal to about 100,000 daltons; and $R_1$–$R_2$, $R_4$–$R_5$, $R_7$–$R_8$, $R_{10}$–$R_{11}$, $R_2$–$R_3$, $R_5$–$R_6$, $R_8$–$R_9$, and $R_{11}$–$R_{12}$ may also possess the atoms necessary to form ring systems, which themselves may possess heteroatoms that may bear one or more functional groups of molecular weight equal to or less than about 100,000 daltons;

with the proviso that at least one of the $R_1$–$R_{16}$ groups is linked to a complexing agent of general formula IIA, IIB, IIC, IID, IIE by way of an organic group that has as part or all of its structure a group Q, which is an amine, an ester, an ether or an amide link:

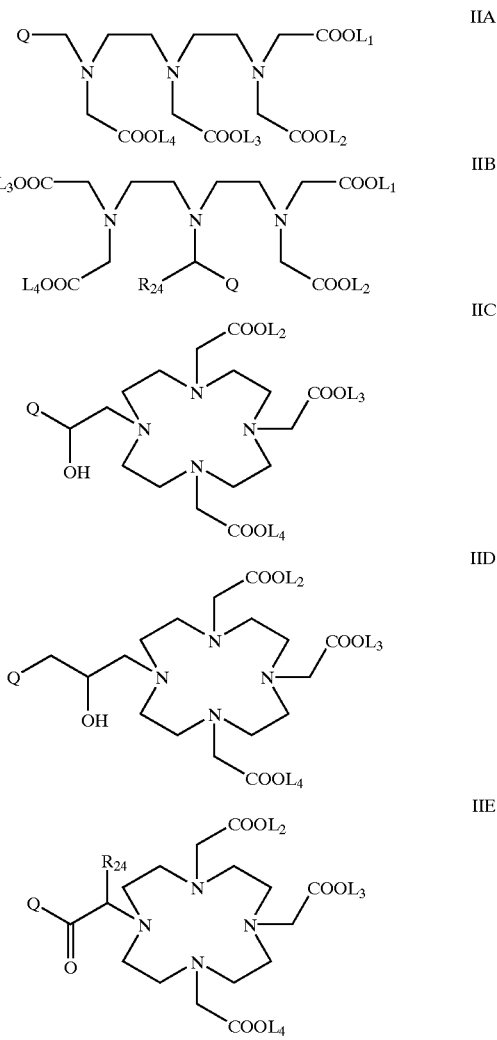

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides; and that when $R_1$ and $R_4$ are methyl, $R_2$ and $R_5$ cannot be methyl, a straight chain C1–C6 alkyl, a C7–C12 aralkyl, $CH_2O$ (C1–C3alkyl), $CH_2OH$, $CH(OH)CH_3$, $CH_2CH_2OH$, $CH(NH(CH_2)_nNH_2)CH_3$, $CH_2CH_2NH(CH_2)_nNH_2$ (where n=2, 3, 4, 6), vinyl, ethyl, CH(O-lower alkanoyl) $CH_3$, CH(O-lower alkylene-OR)$CH_3$, or CH(OR)$CH_3$ (where R=H, lower alkyl, a polyfunctional carbonyl compound excluding a hydrogen atom therefrom or a metal derivative of a polyfunctional carbonyl compound).

In formula I, M is 2H or a diamagnetic or paramagnetic metal ion that may be radioactive or not, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ either with or without a physiologically acceptable charge balancing counter ion.

In a preferred embodiment of the invention, provided are phototherapeutic compositions of metallo-tetrapyrrolic compounds of formula IA:

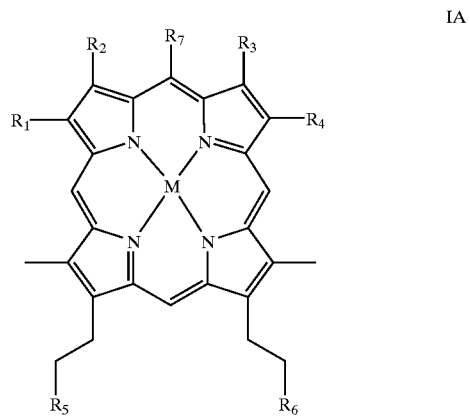

IA

In formula IA, $R_1$–$R_7$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N^+(CH_3)_3A$, $CH=N(alkyl)_2A$, or $N(alkyl)_3^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, $CH(CH_3)O$-aryl;

$(CH_2)_nO$-alkoxy, or $(CH_2)_nO$-alkyl; (where n is an integer from 0 to 8);

$C(X)_2C(X)_3$, where X is a halogen;

$CO_2R_8$, where $R_8$ is selected from a physiologically acceptable counter ion, a straight or branched chain alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, ether or polyether, or a functional group of less than about 100,000 daltons;

$(CH_2)_nOH$, or $(CH_2)_nOR_9$, where $R_9$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{10}$, $(CHX)_nCO_2R_{10}$, or $(CX_2)_nCO_2R_{10}$, where X is a halogen and $R_{10}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{11})$, $CO(R_{11})$, $CON(R_{11})_2$, $CON(R_{11})(R_{12})$, $(CH_2)_nCONH(R_{11})$, $(CH_2)_nCON(R_{11})_2$, $(CH_2)_nCOR_{11}$, $(CH_2)_nCON(R_{11})(R_{12})$, $(CX_2)_nCONH(R_{11})$, $(CX_2)_nCON(R_{11})_2$, $(CX_2)_nCON(R_{11})(R_{12})$, $(CX_2)_nCOR_{11}$, $(CH_2)_nCONHNH(R_{11})$, $(CX_2)_nCONHNH(R_{11})$, $(CHX)_nCONH(R_{11})$, $(CHX)_nCONHNH(R_{11})$, $(CHX)_nCON(R_{11})_2$, $(CHX)_nCON(R_{11})(R_{12})$, where X is a halogen and $R_{11}$ and $R_{12}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{13})$, $(CH_2)_nS(R_{13})$, $(CH_2)_nNH(R_{13})$, $(CH_2)_nNH(R_{13})$, $(CH_2)_nR_{13}$ $(CH_2)_nN(R_{13})(R_{14})$, or $(CH_2)_nN(R_{13})(R_{14})(R_{15})^+A$, where $R_{13}$, $R_{14}$ and $R_{15}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{13}$, $R_{14}$ and $R_{15}$ possess the atoms necessary to constitute an aromatic ring system, n is an integer between 0 and 4, and A is a physiologically acceptable counter ion;

$(CH_2)_nOPO_2OR_{16}$, or $(CH_2)_nPO(OR_{16})_2$, $(CH_2)_nPO_2R_{16}$, $(CH_2)_nPOR_{16}$ where $R_{16}$ is selected from H, a physiologically acceptable counter ion, a straight or branched chain C1–C20 alkyl, haloalkyl, heteroalkyl, haloheteroalkyl, aryl or heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{17}$, $(CH_2)_nNHNHCOR_{17}$, where $R_{17}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{18}$, $SO_2NHR_{18}$, $SO_2N(R_{18})_2$, $SO_2NHNHR_{18}$ or $SO_2R_{18}$, where $R_{18}$ is selected from H, a physiologically acceptable counter ion, a straight or branched chain C1–C20 alkyl, haloalkyl, heteroalkyl, haloheteroalkyl, aryl or heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

aryl or substituted aryl, which may optionally bear one or more substituents with a molecular weight of less than or equal to about 100,000 daltons; and $R_1$–$R_2$, and $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons; with the proviso that $R_1$ and $R_4$ are the same, $R_2$ and $R_3$ are the same, and that when $R_7$ is H, $R_1$–$R_4$ cannot be methyl; and that at least one of the $R_1$–$R_7$ groups is linked to a complexing agent of general formula IIA, IIB, IIC, IID, IIE by way of an organic group that has as part or all of its structure a group Q, which is an amine, a ester, a ether or an amide link:

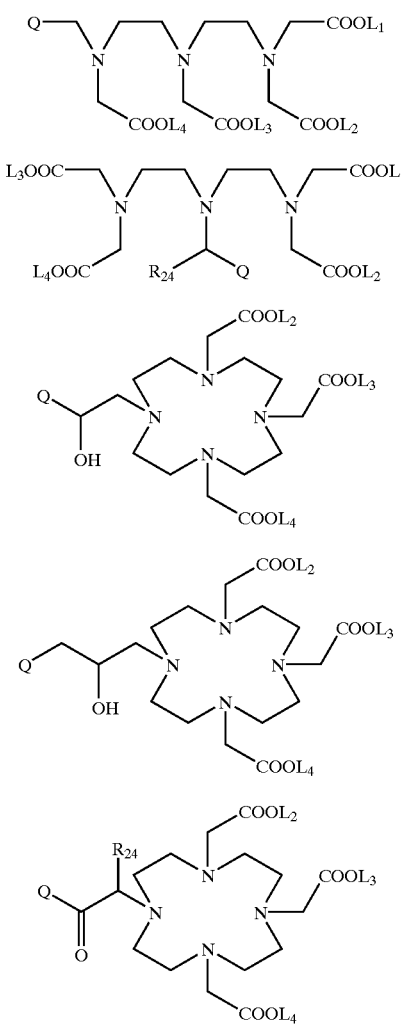

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula IA, M is 2H or a diamagnetic or paramagnetic metal ion that may be radioactive or not, photoactive metals being preferably scheduled from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ either with or without a physiologically acceptable charge balancing counter ion.

In another preferred embodiment of the invention, provided are phototherapeutic compositions of metallotetrapyrrolic compounds of the formula IB:

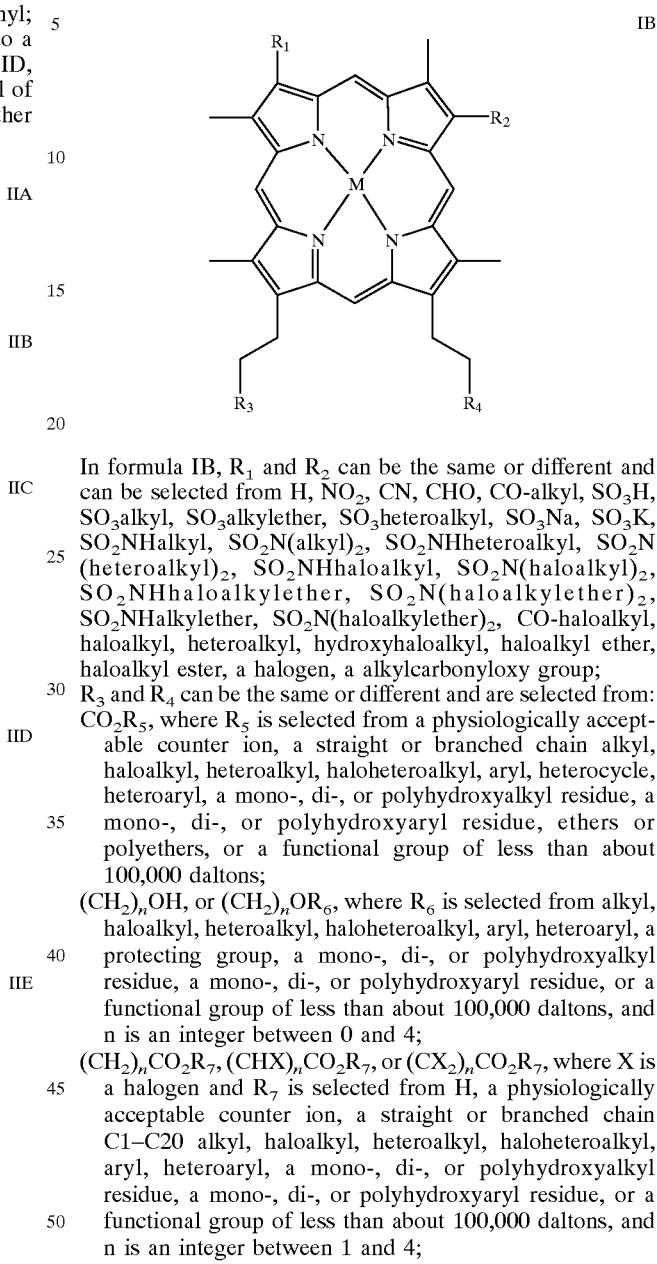

In formula IB, $R_1$ and $R_2$ can be the same or different and can be selected from H, $NO_2$, CN, CHO, CO-alkyl, $SO_3H$, $SO_3$alkyl, $SO_3$alkylether, $SO_3$heteroalkyl, $SO_3Na$, $SO_3K$, $SO_2$NHalkyl, $SO_2$N(alkyl)$_2$, $SO_2$NHheteroalkyl, $SO_2$N(heteroalkyl)$_2$, $SO_2$NHhaloalkyl, $SO_2$N(haloalkyl)$_2$, $SO_2$NHhaloalkylether, $SO_2$N(haloalkylether)$_2$, $SO_2$NHalkylether, $SO_2$N(haloalkylether)$_2$, CO-haloalkyl, haloalkyl, heteroalkyl, hydroxyhaloalkyl, haloalkyl ether, haloalkyl ester, a halogen, a alkylcarbonyloxy group;

$R_3$ and $R_4$ can be the same or different and are selected from:
$CO_2R_5$, where $R_5$ is selected from a physiologically acceptable counter ion, a straight or branched chain alkyl, haloalkyl, heteroalkyl, haloheteroalkyl, aryl, heterocycle, heteroaryl, a mono-, di-, or polyhydroxyalkyl residue, a mono-, di-, or polyhydroxyaryl residue, ethers or polyethers, or a functional group of less than about 100,000 daltons;

$(CH_2)_nOH$, or $(CH_2)_nOR_6$, where $R_6$ is selected from alkyl, haloalkyl, heteroalkyl, haloheteroalkyl, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_7$, $(CHX)_nCO_2R_7$, or $(CX_2)_nCO_2R_7$, where X is a halogen and $R_7$ is selected from H, a physiologically acceptable counter ion, a straight or branched chain C1–C20 alkyl, haloalkyl, heteroalkyl, haloheteroalkyl, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_8)$, $CO(R_8)$, $CON(R_8)_2$, $CON(R_8)(R_9)$, $(CH_2)_nCONH(R_8)$, $(CH_2)_nCON(R_8)_2$, $(CH_2)_nCOR_8$, $(CH_2)_nCON(R_8)(R_9)$, $(CX_2)_nCONH(R_8)$, $(CX_2)_nCON(R_8)_2$, $(CX_2)_nCON(R_8)(R_9)$, $(CX_2)_nCOR_8$, $(CH_2)_nCONHNH(R_8)$, $(CX_2)_nCONHNH(R_8)$, $(CHX)_nCONH(R_8)$, $(CHX)_nCONHNH(R_8)$, $(CHX)_nCON(R_8)_2$, $(CHX)_nCON(R_8)(R_9)$, where X is a halogen and $R_8$ and $R_9$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

S($R_{10}$), $(CH_2)_nS(R_{10})$, $(CH_2)_nNH(R_{10})$, $(CH_2)_nNH(R_{10})$, $(CH_2)_nR_{10}$ $(CH_2)_nN(R_{10})(R_{11})$, or $(CH_2)_nN(R_{10})(R_{11})(R_{12})^+A$, where $R_{10}$, $R_{11}$ and $R_{12}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{10}$, $R_{11}$ and $R_{12}$ possess the atoms necessary to constitute an aromatic ring system, n is an integer between 0 and 4, and A is a physiologically acceptable counter ion;

$(CH_2)_nOPO_2OR_{13}$, $(CH_2)_nPO(OR_{13})_2$, $(CH_2)_nPO_2R_{13}$, $(CH_2)_nPOR_{13}$ where $R_{13}$ is selected from H, a physiologically acceptable counter ion, a straight or branched chain C1–C20 alkyl, haloalkyl, heteroalkyl, haloheteroalkyl, aryl or heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{14}$, $(CH_2)_nNHNHCOR_{14}$, where $R_{14}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{15}$, $SO_2NHR_{15}$, $SO_2N(R_{15})_2$, $SO_2NHNHR_{15}$ or $SO_2R_{15}$, where $R_{15}$ is selected from H, a physiologically acceptable counter ion, a straight or branched chain C1–C20 alkyl, haloalkyl, heteroalkyl, haloheteroalkyl, aryl or heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

aryl or substituted aryl, which may optionally bear one or more substituents with a molecular weight of less than or equal to about 100,000 daltons;

with the proviso that at least one of the $R_1$–$R_4$ groups is linked to a complexing agent of general formula IIA, IIB, IIC, IID, IIE by way of an organic group that has as part or all of its structure a group Q, which is an amine, an ester, an ether or an amide link:

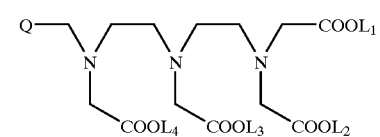

IIA

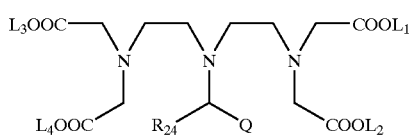

IIB

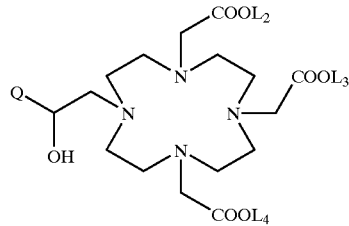

IIC

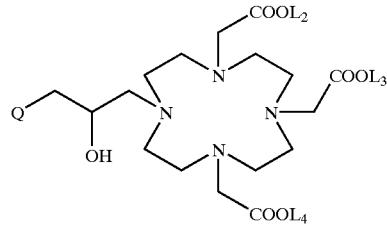

IID

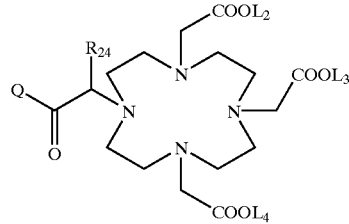

IIE wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula IB, M is 2H or a diamagnetic or paramagnetic metal ion that may be radioactive or not, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ either with or without a physiologically acceptable charge balancing counter ion.

In another aspect of the invention, provided are phototherapeutic, MRI and radiodiagnostic compositions of metallo-tetrapyrrolic compounds of formula II that may be used as photosensitizers in photodynamic therapy:

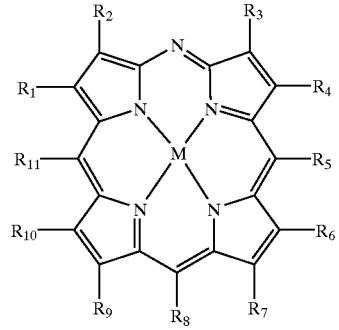

II

In formula II, $R_1$–$R_{11}$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N^+(CH_3)_3A$, $CH=N(alkyl)_2A$, or $N(alkyl)_3{}^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_{12}$, where $R_{12}$ is selected from a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{13}$, where $R_{13}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{14}$, $(CHX)_nCO_2R_{14}$, or $(CX_2)_nCO_2R_{14}$, where X is a halogen and $R_{14}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons, and n is an integer between 1 and 4;

$CONH(R_{15})$, $CONHNH(R_{15})$, $CO(R_{15})$, $CON(R_{15})_2$, $CON(R_{15})(R_{16})$, $(CH_2)_nCONH(R_{15})$, $(CH_2)_nCONHNH(R_{15})$, $(CH_2)_nCON(R_{15})_2$, $(CH_2)_nCOR_{15}$, $(CH_2)_nCON(R_{15})(R_{16})$, $(CX_2)_nCONH(R_{15})$, $(CX_2)_nCON(R_{15})_2$, $(CX_2)_nCON(R_{15})(R_{16})$, $(CX_2)_nCOR_{15}$, $(CH_2)_nCONHNH(R_{15})$, $(CX_2)_nCONHNH(R_{15})$, $(CHX)_nCONH(R_{15})$, $(CHX)_nCONHNH(R_{15})$, $(CHX)_nCON(R_{15})_2$, $(CHX)_nCON(R_{15})(R_{16})$, where X is a halogen and $R_{15}$ and $R_{16}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{17})$, $(CH_2)_nS(R_{17})$, $(CH_2)_nNH(R_{17})$, $(CH_2)_nNH(R_{17})$, $(CH_2)_nR_{17}$, $(CH_2)_nN(R_{17})(R_{18})$, or $(CH_2)_nN(R_{17})(R_{18})(R_{19})^+A$, where $R_{17}$, $R_{18}$ and $R_{19}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, an amino acid amide, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{17}$, $R_{18}$ and $R_{19}$ possess the atoms necessary to constitute an aromatic ring system, n is an integer between 0 and 4, and A is a physiologically acceptable counter ion;

$(CH_2)_nOPO_2OR_{20}$, or $(CH_2)_nPO(OR_{20})_2$, $(CH_2)_nPO_2R_{20}$, $(CH_2)_nPOR_{20}$ where $R_{20}$ is selected from H, a physiologically acceptable counter ion, a straight or branched chain C1–C20 alkyl, haloalkyl, heteroalkyl, haloheteroalkyl, aryl or heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{21}$, or $(CH_2)_nNHNHCOR_{21}$, where $R_{21}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{22}$, $SO_2NHR_{22}$, $SO_2N(R_{22})_2$, $SO_2NHNHR_{22}$ or $SO_2R_{22}$, where $R_{22}$ is selected from H, a physiologically acceptable counter ion, a straight or branched chain C1–C20 alkyl, haloalkyl, heteroalkyl, haloheteroalkyl, aryl or heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid residue, an amino acid salt, an amino acid ester residue, an amino acid amide residue, or a functional group of less than about 100,000 daltons;

aryl or substituted aryl, which may optionally bear one or more substituents with a molecular weight of less than or equal to about 100,000 daltons;

$R_1$–$R_2$, $R_3$–$R_4$, $R_6$–$R_7$, $R_9$–$R_{10}$, $R_4$–$R_5$, $R_5$–$R_6$, $R_7$–$R_8$, $R_8$–$R_9$, $R_{10}$–$R_{11}$, or $R_{11}$–$R_1$, may also possess the atoms necessary to form ring systems, either aromatic or not, which themselves may possess heteroatoms that may be charged or neutral or bear one or more functional groups of molecular weight equal to or less than about 100,000 daltons; with the proviso that at least one of the $R_1$–$R_{11}$ groups is linked to a complexing agent of general formula IIA, IIB, IIC, IID, IIE by way of an organic group that has as part or all of its structure a group Q, which is an amine, an ester, an ether or an amide link:

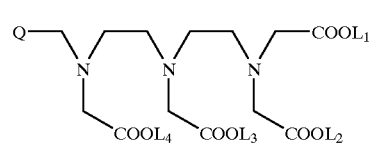

IIA

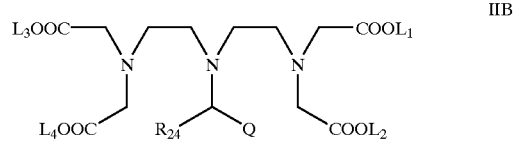

IIB

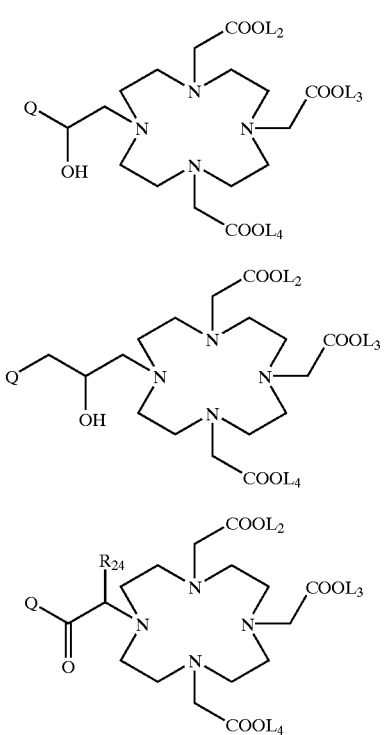

wherein $R_{24}$ is selected from a hydrogen, a straight or branched chain $C_1$-$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula II, M is 2H or a diamagnetic or paramagnetic metal ion that can be radioactive, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$, either with or without a physiologically acceptable charge balancing counter ion.

In a preferred embodiment of the invention, provided are phototherapeutic compositions of metallo-tetrapyrrolic compounds of following formula IIA:

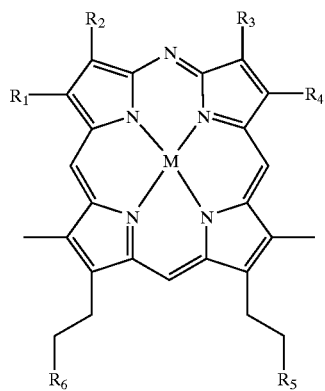

In formula IIA, $R_1$-$R_6$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N^+(CH_3)_3A$, $CH=N(alkyl)_2A$, or $N(alkyl)_3^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, or $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_7$, where $R_7$ is selected from a physiologically acceptable counter ion, a straight or branched chain alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_8$, where $R_8$ is selected from alkyl, haloalkyl, heteroalkyl, haloheteroalkyl, aryl, heteroaryl, heterocycle, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_9$, $(CHX)_nCO_2R_9$, or $(CX_2)_nCO_2R_9$, where X is a halogen and $R_9$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{10})$, $CONHNH(R_{10})$, $CO(R_{10})$, $CON(R_{10})_2$, $CON(R_{10})(R_{11})$, $(CH_2)_nCONH(R_{10})$, $(CH_2)_nCONHNH(R_{10})$, $(CH_2)_nCON(R_{10})_2$, $(CH_2)_nCOR_{10}$, $(CH_2)_nCON(R_{10})(R_{11})$, $(CX_2)_nCONH(R_{10})$, $(CX_2)_nCON(R_{10})_2$, $(CX_2)_nCON(R_{10})(R_{11})$, $(CX_2)_nCOR_{10}$, $(CH_2)_nCONHNH(R_{10})$, $(CX_2)_nCONHNH(R_{10})$, $(CHX)_nCONH(R_{10})$, $(CHX)_nCONHNH(R_{10})$, $(CHX)_nCON(R_{10})_2$, or $(CHX)_nCON(R_{10})(R_{11})$, where X is a halogen and $R_{10}$ and $R_{11}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{12})$, $(CH_2)_nS(R_{12})$, $(CH_2)_nNH(R_{12})$, $(CH_2)_nNHNH(R_{12})$, $(CH_2)_nN(R_{12})_2$, $(CH_2)_nN(R_{12})(R_{13})$, or $(CH_2)_nN(R_{12})(R_{13})(R_{14})^+A$, where $R_{12}$, $R_{13}$ and $R_{14}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, or an amino acid amide provided —$NH(R_{13})$ is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{12}$, $R_{13}$ and $R_{14}$ possess the atoms necessary to constitute an aromatic ring system, n is an integer between 0 and 4, and A is a physiologically acceptable counter ion;

$(CH_2)_nOPO_2OR_{15}$, or $(CH_2)_nPO(OR_{15})_2$, $(CH_2)_nPO_2R_{15}$, $(CH_2)_nPOR_{15}$ where $R_{11}$ is selected from H, a physiologically acceptable counter ion, a straight or branched chain C1–C20 alkyl, haloalkyl, heteroalkyl, haloheteroalkyl, aryl or heteroaryl, heterocycle, amino acids and salts, esters, or amides thereof, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{16}$, or $(CH_2)_nNHNHCOR_{16}$, where $R_{16}$ is selected from a straight or branched chain C1–C20 alkyl, haloalkyl, heteroalkyl, haloheteroalkyl, aryl, heteroaryl, heterocycle, amino acids and salts, esters, or amides thereof, or a functional group of less than about 100,000 daltons, and n is an integer between 0 and 4;

$SO_3R_{17}$, $SO_2NHR_{17}$, $SO_2N(R_{17})_2$, $SO_2NHNHR_{17}$ or $SO_2R_{17}$, where $R_{17}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, and $NHR_{17}$ can be an amino acid residue, an amino acid salt, an amino acid ester residue, an amino acid amide residue;

aryl or substituted aryl, which may optionally bear one or more substituents with a molecular weight of less than or equal to about 100,000 daltons; and $R_1$–$R_2$, and $R_3$–$R_4$ may also possess the atoms necessary to form ring systems, either aromatic or not, which themselves may possess heteroatoms that may be charged or neutral or bear one or more functional groups of molecular weight equal to or less than about 100,000 daltons;

with the proviso that at least one of the $R_1$–$R_4$ groups is linked to a complexing agent of general formula IIA, IIB, IIC, IID, IIE by way of an organic group that has as part or all of its structure a group Q, which is an amine, an ester, an ether or an amide link:

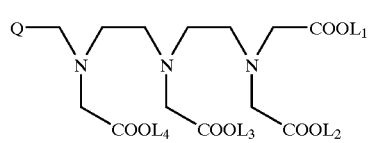

IIA

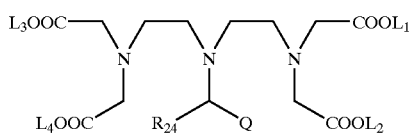

IIB

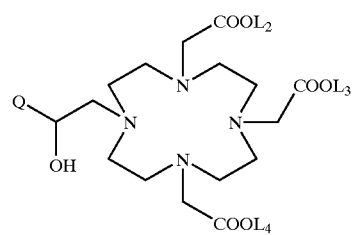

IIC

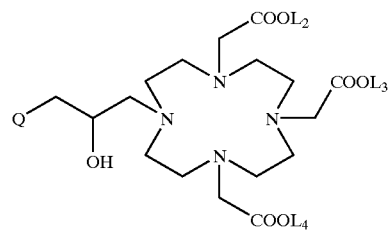

IID

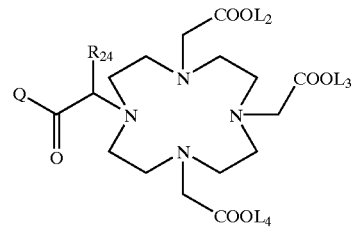

IIE wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula IIA, M is 2H or a diamagnetic or paramagnetic metal ion that may be radioactive or not, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$, either with or without a physiologically acceptable charge balancing counter ion.

Additionally and in accordance with the present invention, provided are phototherapeutic compositions of metallo-tetrapyrrolic compounds of formula III that may be used as MRI, radiodiagnostic, or PDT agents:

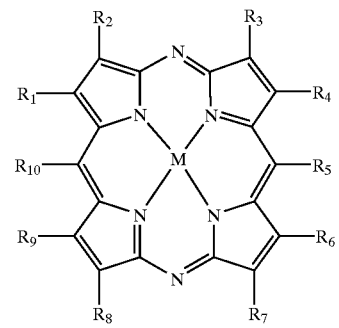

III

In formula III, $R_1$–$R_{10}$ can be the same or different and can be selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group having a molecular weight of less than about 100,000 daltons; $CH=CHCH_2N^+(CH_3)_3A$, $CH=N(alkyl)_2A$, or $N(alkyl)_3{}^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, or $CH(CH_3)O$-aryl;

$(CH_2)_nO$-alkoxy, or $(CH_2)_nO$-alkyl, where n is an integer from 0 to 8;

$C(X)_2C(X)_31$ where X is a halogen;

$CO_2R_{11}$, where $R_{11}$ is selected from a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{12}$, where $R_{12}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{13}$, $(CHX)_nCO_2R_{13}$, or $(CX_2)_nCO_2R_{13}$, where X is a halogen and $R_{13}$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{14})$, $CONHNH(R_{14})$, $CO(R_{14})$, $CON(R_{14})_2$, $CON(R_{14})(R_{15})$, $(CH_2)_nCONH(R_{14})$, $(CH_2)_nCONHNH(R_{14})$, $(CH_2)_nCON(R_{14})_2$, $(CH_2)_nCOR_{14}$, $(CH_2)_nCON(R_{14})(R_{15})$, $(CX_2)_nCONH(R_{14})$, $(CX_2)_nCON(R_{14})_2$, $(CX_2)_nCON(R_{14})(R_{15})$, $(CX_2)_nCOR_{14}$, $(CH_2)_nCONHNH(R_{14})$, $(CX_2)_nCONHNH(R_{14})$, $(CHX)_nCONH(R_{14})$, $(CHX)_nCONHNH(R_{14})$, $(CHX)_nCON(R_{14})_2$, $(CHX)_nCON(R_{14})(R_{15})$, where X is a halogen and $R_{14}$ and $R_{15}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{16})$, $(CH_2)_nS(R_{16})$, $(CH_2)_nNH(R_{16})$, $(CH_2)_nNHNH(R_{16})$, $(CH_2)_nN(R_{16})_2$ $(CH_2)_nN(R_{16})(R_{17})$, or $(CH_2)_nN(R_{16})(R_{17})(R_{18})^+A$, where $R_{16}$, $R_{17}$ and $R_{18}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, or an amino acid amide provided —$NHR_{16}$ is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{16}$, $R_{17}$ and $R_{18}$ together possess the atoms necessary to constitute an aromatic ring system, n is an integer between 0 and 4, and A is a physiologically acceptable counter ion;

$(CH_2)_nOPO_2OR_{19}$, or $(CH_2)_nPO(OR_{19})_2$, $(CH_2)_nPO_2R_{19}$, $(CH_2)_nPOR_{19}$ where $R_{19}$ is selected from H, a physiologically acceptable counter ion, a straight or branched chain C1–C20 alkyl, haloalkyl, heteroalkyl, haloheteroalkyl, aryl, heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{20}$, $(CH_2)_nNHNHCOR_{20}$, where $R_{20}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{21}$, $SO_2NHR_{21}$, $SO_2N(R_{21})_2$, $SO_2NHNHR_{21}$ or $SO_2R_{21}$, where $R_{21}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons; and $NHR_{21}$ can be an amino acid residue, an amino acid salt, an amino acid ester residue, or an amino acid amide residue;

aryl or substituted aryl, which may optionally bear one or more substituents with a molecular weight of less than or equal to about 100,000 daltons; and $R_1$–$R_2$, $R_3$–$R_4$, $R_6$–$R_7$, $R_8$–$R_9$, $R_4$–$R_5$, $R_5$–$R_6$, $R_9$–$R_{10}$ and $R_{10}$–$R_1$ may also possess the atoms necessary to form ring systems, either aromatic or not, which themselves may possess heteroatoms that may be charged or neutral or bear one or more functional groups of molecular weight equal to or less than about 100,000 daltons;

with the proviso that at least one of the $R_1$–$R_4$ groups is linked to a complexing agent of general formula IIA, IB, IIC, IID, IIE by way of an organic group that has as part or all of its structure a group Q, which is an amine, an ester, an ether or an amide link:

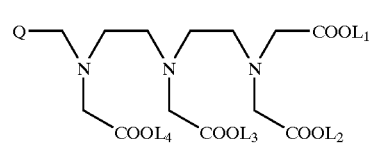

IIA

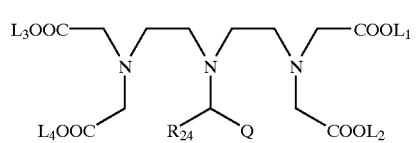

IIB

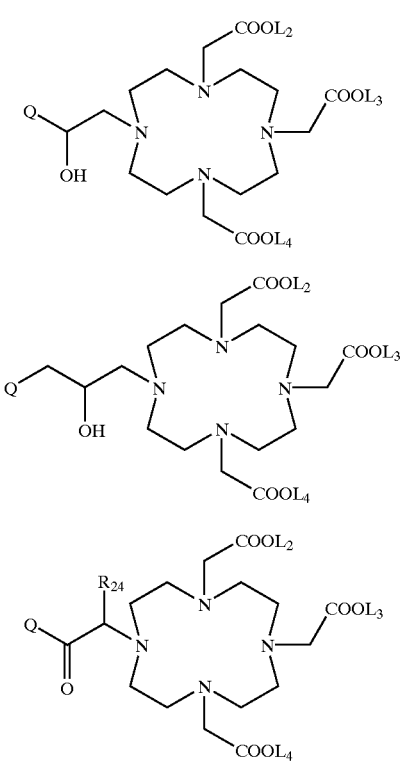

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula III, M is 2H or a diamagnetic or paramagnetic metal ion that may be radioactive or not, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ either with or without a physiologically acceptable charge balancing counter ion.

In a preferred embodiment of the invention, provided are phototherapeutic compositions of metal-tetrapyrolic compounds of formula IIIA:

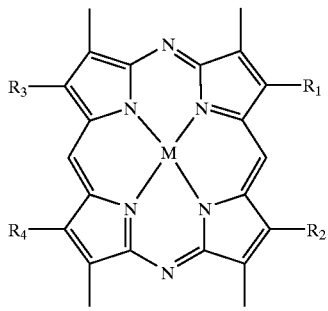

IIIA

In formula IIIA, $R_1$–$R_4$ can be the same or different and are selected from: a functional group of less than about 100,000 daltons;

$CO_2R_5$, where $R_5$ is selected from H, a physiologically acceptable counter ion, a straight or branched chain C1–C20 alkyl, haloalkyl, heteroalkyl, haloheteroalkyl, aryl, heterocycle, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_6$, where $R_6$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_7$, $(CHX)_nCO_2R_7$, or $(CX_2)_nCO_2R_7$, where X is a halogen and $R_7$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_8)$, $(CONHNH(R_8)$, $CO(R_8)$, $CON(R_8)_2$, $CON(R_8)(R_9)$, $(CH_2)_nCONH(R_8)$, $(CH_2)_nCONHNH(R_8)$, $(CH_2)_nCON(R_8)_2$, $(CH_2)_nCOR_8$, $(CH_2)_nCON(R_8)(R_9)$, $(CX_2)_nCONH(R_8)$, $(CX_2)_nCON(R_8)_2$, $(CX_2)_nCON(R_8)(R_9)$, $(CX_2)_nCOR_8$, $(CH_2)_nCONHNH(R_8)$, $(CX_2)_nCONHNH(R_8)$, $(CHX)_nCONH(R_8)$, $(CHX)_nCONHNH(R_8)$, $(CHX)_nCON(R_8)_2$, or $(CHX)_nCON(R_8)(R_9)$, where X is a halogen and $R_8$ and $R_9$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, an amino acid, an amino acid salt, an amino acid ester, an amino acid amide, or a functional group of less than about 100,000 daltons, and n is an integer between 0 and 4;

$S(R_{10})$, $(CH_2)_nS(R_{10})$, $(CH_2)_nNH(R_{10})$, $(CH_2)_nNHNH(R_{10})$, $(CH_2)_nN(R_{10})_2$, $(CH_2)_nN(R_{10})(R_{11})$, or $(CH_2)_nN(R_{10})(R_{11})(R_{12})^+A$, where $R_{10}$, $R_{11}$ and $R_{12}$ can be the same or different and are selected from H, $NH_2$, straight or branched chain $C_1$–C20 alkyl, haloalkyl, heteroalkyl, haloheteroalkyl, aryl, heteroaryl, heterocycle, amino acids, an amino acid ester, or an amino acid amide provided —$NHR_{10}$ is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{10}$, $R_{11}$ and $R_{12}$ together possess the atoms necessary to constitute an aromatic ring system, n is an integer between 0 and 4, and A is a physiologically acceptable counter ion;

$(CH_2)_nOPO_2OR_{13}$, or $(CH_2)_nPO(OR_{13})_2$, $(CH_2)_nPO_2R_{13}$, $(CH_2)_nPOR_{13}$ where $R_{13}$ is selected from H, a physiologically acceptable counter ion, a straight or branched chain C1–C20 alkyl, haloalkyl, heteroalkyl, haloheteroalkyl, aryl, heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{14}$, or $(CH_2)_nNHNHCOR_{14}$, where $R_{14}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{15}$, $SO_2NHR_{15}$, $SO_2N(R_{15})_2$, $SO_2NHNHR_{15}$ or $SO_2R_{15}$, where $R_{15}$ is selected from H, a physiologically acceptable counter ion, a straight or branched chain C1–C20 alkyl, haloalkyl, heteroalkyl, haloheteroalkyl, aryl, heteroaryl, heterocycle; $NHR_{15}$ can also be an amino acid residue, an amino acid salt, an amino acid ester residue, or an amino acid amide residue; a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons;

aryl or substituted aryl, which may optionally bear one or more substituents with a molecular weight of less than or equal to about 100,000 daltons;

with the proviso that at least one of the $R_1$–$R_4$ groups is linked to a complexing agent of general formula IIA, IIB, IIC, IID, IIE by way of an organic group that has as part or all of its structure a group Q, which is an amine, an ester, an ether or an amide link:

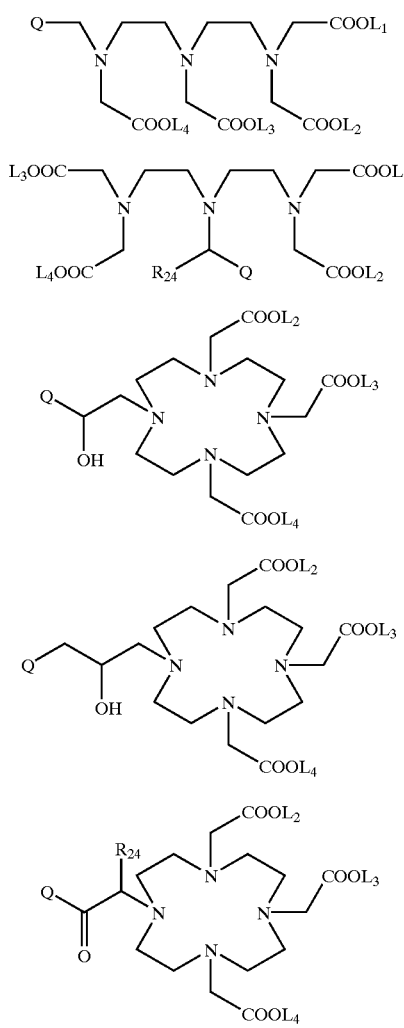

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides.

In formula IIIA, M is 2H or a diamagnetic or paramagnetic metal ion that may be radioactive or not, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ either with or without a physiologically acceptable charge balancing counter ion.

In another aspect of the invention, provided are phototherapeutic compositions of metallo-tetrapyrrolic compounds of formula IV that may be used as MRI, radiodiagnostic, or PDT agents:

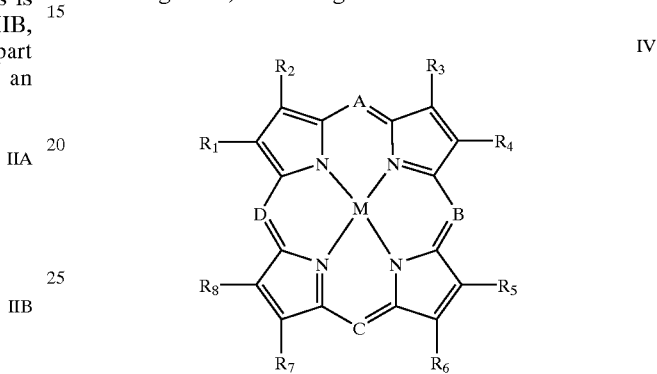

In formula IV, $R_1$–$R_8$ can be the same or different and are selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ethers, polyethers, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N(CH_3)_3{}^+A$, $CH=N(alkyl)_2{}^+A$, or $N(alkyl)_3{}^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, or $CH(CH_3)O$-aryl;

$(CH_2)_nO$-alkoxy, or $(CH_2)_nO$-alkyl; where n is an integer from 0 to 8;

$C(X)_2C(X)_3$, where X is a halogen;

$CO_2R_9$, where $R_9$ is selected from a physiologically acceptable counter ion, a straight or branched chain C1–C20 alkyl, haloalkyl, heteroalkyl, haloheteroalkyl, aryl, heterocycle, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{10}$, where $R_{10}$ is selected from alkyl, haloalkyl, heteroalkyl, haloheteroalkyl, aryl, heterocycle, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{11}$, $(CHX)_nCO_2R_{11}$, $(CX_2)_nCO_2R_{11}$, where X is a halogen and $R_{11}$ is selected from H, a physiologically acceptable counter ion, a straight or branched chain C1–C20 alkyl, haloalkyl, heteroalkyl, haloheteroalkyl, aryl, heterocycle, heteroaryl, a mono-, di-, or polyhydroxyalkyl residue, a mono-, di-, or polyhydroxyaryl residue, or a functional group of less than about 100,000 daltons, and n is an integer between 1 and 4;

$CONH(R_{12})$, $CONHNH(R_{12})$ $CO(R_{12})$, $CON(R_{12})_2$, $CON(R_{12})(R_{13})$, $(CH_2)_nCONH(R_{12})$, $(CH_2)_nCONHNH(R_{12})$, $(CH_2)_nCON(R_{12})_2$, $(CH_2)_nCOR_{12}$, $(CH_2)_nCON(R_{12})(R_{13})$, $(CX_2)_nCONH(R_{12})$, $(CX_2)_nCON(R_{12})_2$, $(CX_2)_nCON(R_{12})(R_{13})$, $(CX_2)_nCOR_{12}$, $(CH_2)_nCONHNH(R_{12})$, $(CX_2)_nCONHNH(R_{12})$, $(CHX)_nCONH(R_{12})$, $(CHX)_nCONHNH(R_{12})$, $(CHX)_nCON(R_{12})_2$, $(CHX)_nCON(R_{12})(R_{13})$, where X is a halogen and $R_{12}$ and $R_{13}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

$S(R_{14})$, $(CH_2)_nS(R_{14})$, $(CH_2)_nNH(R_{14})$, $(CH_2)_nNHNH(R_{14})$, $(CH_2)_nN(R_{14})_2$, $(CH_2)_nN(R_{14})(R_{15})$, or $(CH_2)_nN(R_{14})(R_{15})(R_{16})^+A$, where $R_{14}$, $R_{15}$ and $R_{16}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, or an amino acid amide provided-$NH(R_{14})$ is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{14}$, $R_{15}$ and $R_{16}$ together possess the atoms necessary to constitute an aromatic ring system, n is an integer between 0 and 4, and A is a physiologically acceptable counter ion;

$(CH_2)_nOPO_2OR_{17}$, or $(CH_2)_nPO(OR_{17})_2$, $(CH_2)_nPO_2R_{17}$, $(CH_2)_nPOR_{17}$ where $R_{17}$ is selected from H, a physiologically acceptable counter ion, a straight or branched chain C1–C20 alkyl, haloalkyl, heteroalkyl, haloheteroalkyl, aryl, heteroaryl, heterocycle, amino acids, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{18}$, or $(CH_2)_nNHNHCOR_{18}$, where $R_{18}$ is selected from a straight or branched chain C1–C20 alkyl, haloalkyl, heteroalkyl, haloheteroalkyl, aryl, heteroaryl, heterocycle, or a functional group of less than about 100,000 daltons, and n is an integer between 0 and 4;

$SO_3R_{19}$, $SO_2NHR_{19}$, $SO_2N(R_{19})_2$, $SO_2NHNHR_{19}$ or $SO_2R_{19}$, where $R_{19}$ is selected from H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and $NHR_{19}$ can also be an amino acid residue, an amino acid salt, an amino acid ester residue, or an amino acid amide residue; and aryl or substituted aryl, which may optionally bear one or more substituents selected from hydroxy groups, alkyl groups, carboxyl groups and its esters and amides and sulfonic acid groups and their esters and amides, and substitiuents with a molecular weight of less than or equal to about 100,000 daltons;

with the proviso that at least one of the $R_1$–$R_{12}$ groups is linked to a complexing agent of general formula IIA, IIB, IIC, IID, IIE by way of an organic group that has as part or all of its structure a group Q, which is an amine, an ester, an ether or an amide link:

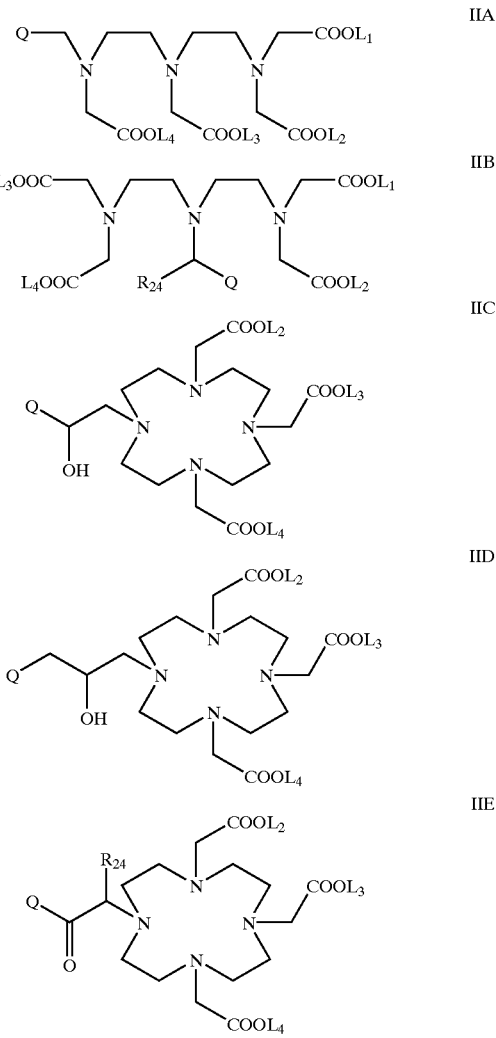

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides; and A, B, C, and D can be the same or different and can be selected from N, CH, $CR_{20}$ where $R_{20}$ is selected from a halogen, aryl, subsitituted aryl, heteroaryl, alkyl, haloalkyl, heterohaloalkyl, heterocycle, hydroxyalky, hydroxyhaloalkyl, or a functional group of molecular weight of less than about 100,000 daltons.

In formula IV, M is selected from 2H or a diamagnetic or paramagnetic metal ion that can be radioactive, photoactive metals being preferably selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, $Mg^{2+}$ the appropriate number of physiologically acceptable charge balancing counter ions.

In accordance with a preferred embodiment of the invention, the metallo-tetrapyrrolic compounds of the invention can be derived by various procedures from naturally occuring cyclic tetrapyrroles. The naturally occurring cyclic tetrapyrrolic molecules can have the basic ring structure of compounds I, II, III, and IV, whose substituents are outlined in Table 1, and are particularly preferred as starting materials for the synthesis of the compounds of structures I–IV. In particular, tetrapyrroles derived from naturally occuring ring systems that have one linking group are particularly preferred. These are shown in scheme 1.

In a second preferred aspect of this invention, the tetrapyrrole is derived by the coupling of suitably substituted dipyrromethane, dipyrromethenes, biladienes, builirubins, pyrroles and functionalized aldehydes, or functionalized maleonitriles. The cyclic tetrapyrroles that have the basic ring structure of compounds I–IV, whose substituents are outlined in Table 2, are particularly preferred as starting materials for the synthesis of compounds of structures I–IV.

It is to be understood that both the foregoing general description and the following detailed description are exemplary and explanatory only and are not restrictive of the invention as claimed.

DETAILED DESCRIPTION OF THE PREFERRED EMBODIMENTS

The terms "tetrapyrrole", tetrapyrrolic molecule and "porphyrin" are used here to designate compounds of the cyclic structure where four pyrrolic ring systems are linked via either carbon or nitrogen bonds. Compounds within the scope of the invention include porphyrins, mono-, di-, tri- and tetraazaporphyrins, and porphyrin isomers such as porphycenes, isoporphycenes, hemiporphycenes, corroles, corrphycenes, and the like.

Included in the first class of metallated tetrapyrrolic compounds of the invention are those of the porphyrins. Scheme 1 outlines an example of the synthesis of porphyrins that are derived from plants. Particularly advantageous are the porphyrins based on chloroporphyrin e6 (9), chloroporphyrin e4 (10), phylloporphyrin (11), rhodoporphyrin (7), pyrroporphyrin (8), pheoporphyrin a5 (13) and phylloerythrin (12) and compounds having similar ring systems. Such compounds can be synthesized with single linking groups, which can be modified according to the invention to increase their biological activity and MRI and radiodiagnostic capacity. In particular, the propionic esters of (2), (3), (5) and (6) can be selectively hydrolyzed to form carboxylic acids, which can then be linked to the metal coordinating moiety. Alternatively, the carboxylic acids can be converted to amides with a free amine linking unit, which can then be linked to the metal coordinating moiety. Porphyrin amide derivatives like (4) ($R_2$=$NHR_3$) may be synthesized from phylloporphyrin such that an amine linking group is present. Examples include where $R_2$=$NHCH_2CH_2NH_2$, $NHCH_2CH_2CH_2NH_2$, $NHCH_2CH_2NH_2$, $NH(CH_2)_2O(CH_2)_2NH_2$ and similar compounds. These amine groups can then be linked to the metal coordinating moiety.

While plant derived porphyrins are preferred as starting materials in the invention due to their abundant availability, a very large number of synthetic porphyrins are generally applicable to the invention. Such porphyrins can be made by synthetic methods known to those skilled in the art, via coupling of pyrrolic precursors, dipyrromethanes, dipyrromethenes and biladienes to give the required porphyrins with widely ranging functionality at both the β and meso positions. The synthesis of porphyrins via the coupling of pyrrolic intermediates is outlined in detail in chapters 1, 2, 3 in "The Porphyrin Handbook" Editors, K. M. Kadish, K. M. Smith, R. Guilard, Volume 1, Academic press, 2000, p. 1–148, the disclosure of which is hereby incorporated by reference herein. Such functionality is explained in detail below. This functionality can be modified by further chemical reactions. Such compounds can then be modified according to the invention to produce metalloporphyrins that absorb at or about 400, 532 and 575 nm. Table 1 outlines some of the preferred porphyrins that may be used as starting materials in the development of these types of compounds.

TABLE 1

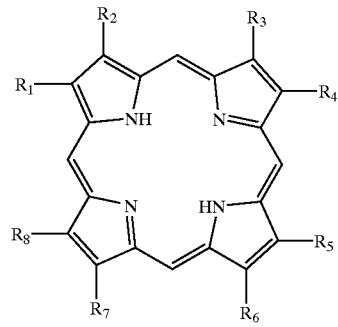

| Tetrapyrrole | $R_1$ | $R_2$ | $R_3$ | $R_4$ | $R_5$ | $R_6$ | $R_7$ | $R_8$ |
|---|---|---|---|---|---|---|---|---|
| Hematoporphyrin IX | Me | EO | Me | EO | Me | PO | PO | Me |
| Protoporphyrin IX | Me | V | Me | V | Me | PO | PO | Me |
| Mesoporphyrin IX | Me | Et | Me | Et | Me | PO | PO | Me |
| Deuteroporphyrin IX | Me | H | Me | H | Me | PO | PO | Me |

TABLE 1-continued

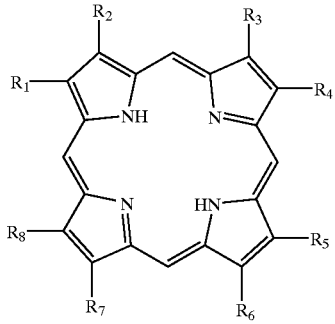

| Tetrapyrrole | $R_1$ | $R_2$ | $R_3$ | $R_4$ | $R_5$ | $R_6$ | $R_7$ | $R_8$ |
|---|---|---|---|---|---|---|---|---|
| Hematoporphyrin dialkylethers | Me | EOE | Me | EOE | Me | PO | PO | Me |
| Coproporphyrin I | PO | Me | PO | Me | PO | Me | PO | Me |
| Coproporphyrin II | Me | PO | PO | Me | Me | PO | PO | Me |
| Coproporphyrin III | Me | PO | Me | PO | Me | PO | PO | Me |
| Uroporphyrin IX | Me | EO | Me | EO | Me | PO | PO | Me |
| Pentacarboxyporphyrin I | PO | Me | PO | Me | PO | Me | PO | AO |
| Pentacarboxyporphyrin III | PO | Me | PO | Me | PO | Me | AO | PO |
| 2,4-dihalodeuteroporphyrin IX | Me | X | Me | X | Me | PO | PO | Me |
| Hexacarboxyporphyrin I | PO | Me | PO | AO | PO | Me | PO | AO |
| Hexacarboxyporphyrin III | PO | Me | PO | Me | PO | AO | PO | AO |
| Heptacarboxyporphyrin I | PO | Me | PO | AO | PO | AO | PO | AO |

AO = —$CH_2CO_2H$; PO = —$CH_2CH_2CO_2H$, EO = —$CH(OH)CH_3$, EOE = —$CH(OR)CH_3$, Me = —$CH_3$, Et = $CH_2CH_3$, V = —$CH=CH_2$

Scheme 1. Plant Derived Porphyrins

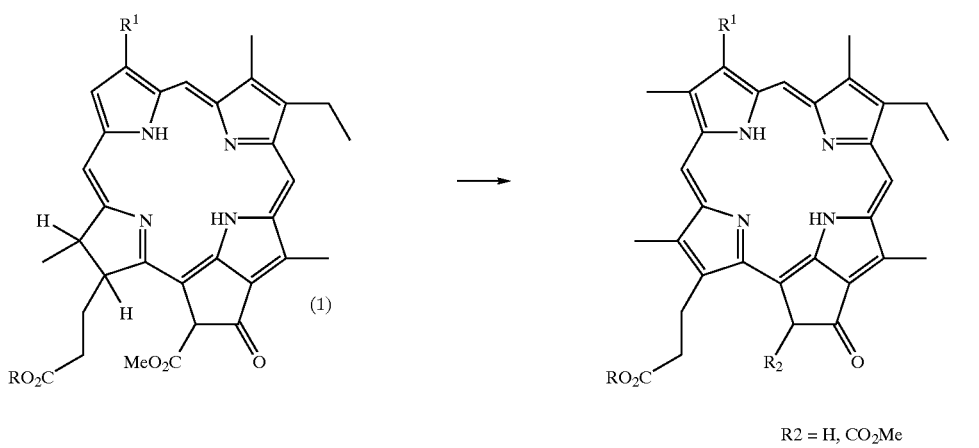

R2 = H, $CO_2Me$

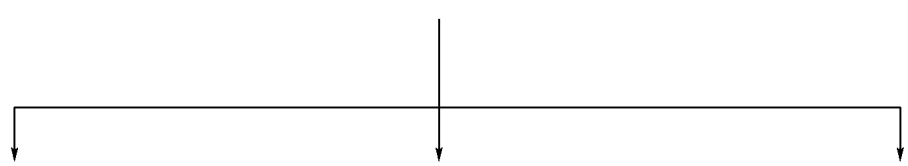

35
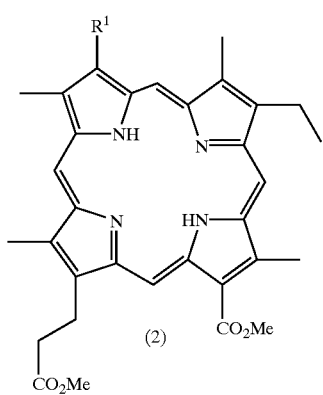
(2)
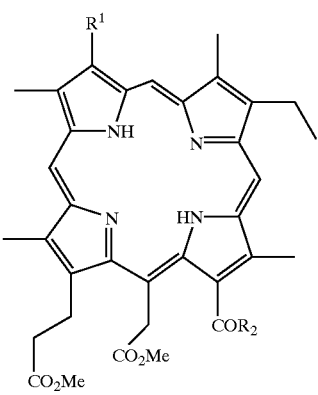
(4)
36
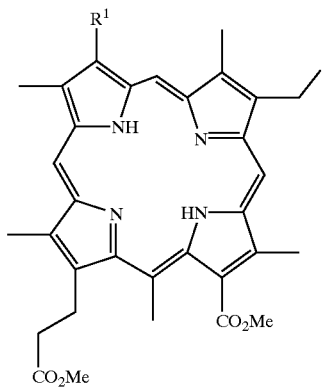
(5)
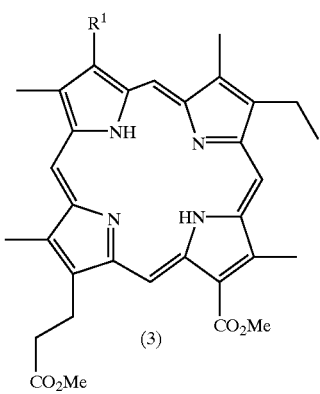
(3)
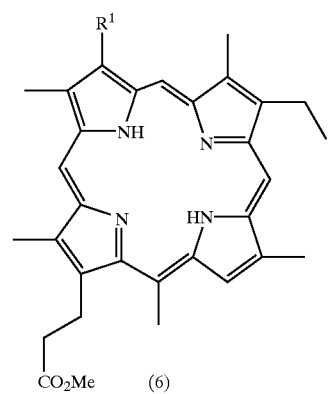
(6)
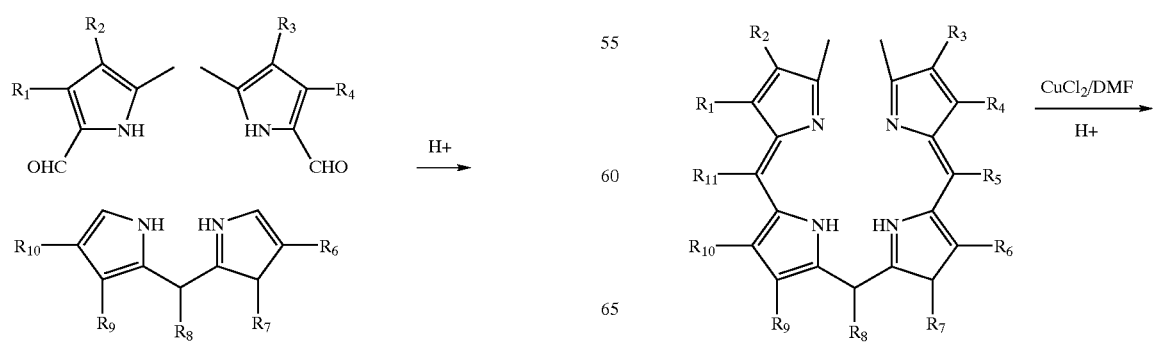
Scheme 2. Synthesis of porphyrins via pyrrolic intermediates.

37
-continued
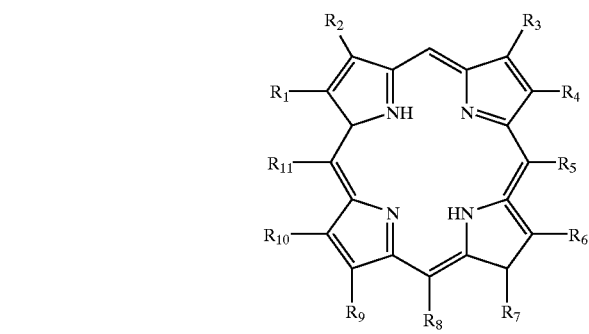
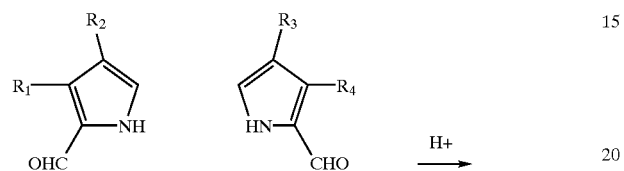
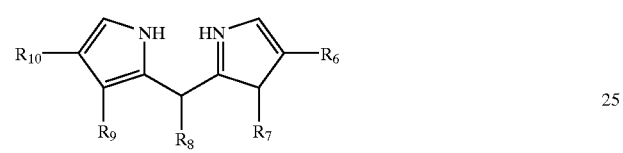
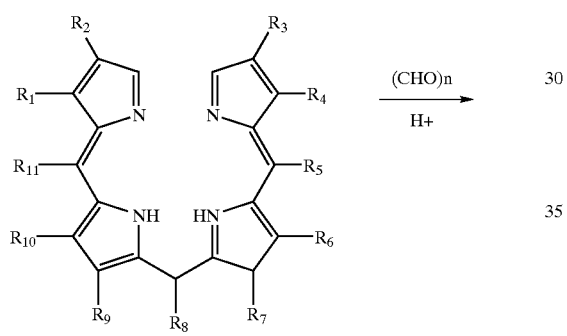
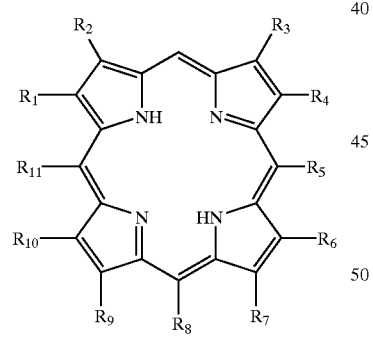
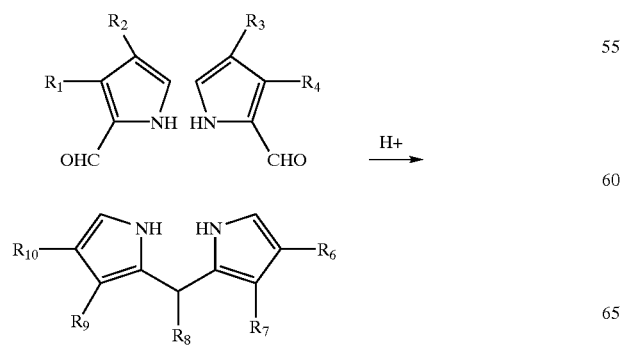
38
-continued
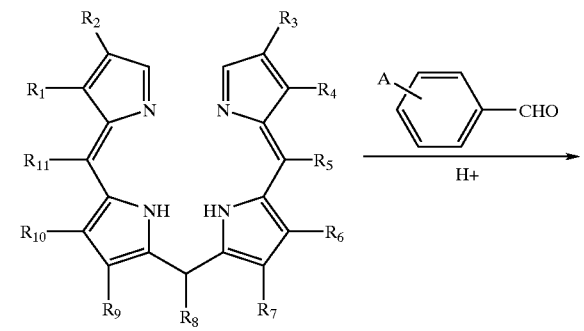
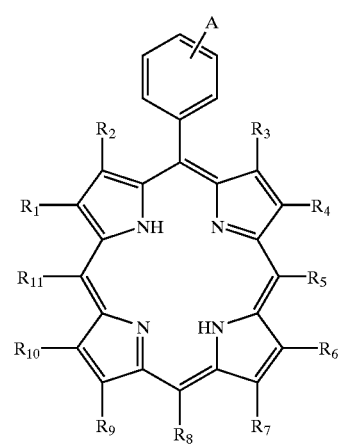
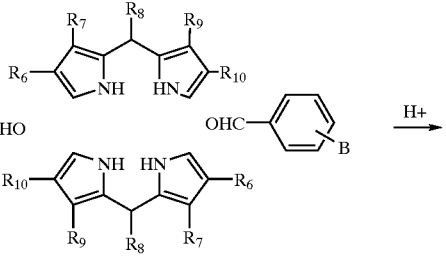
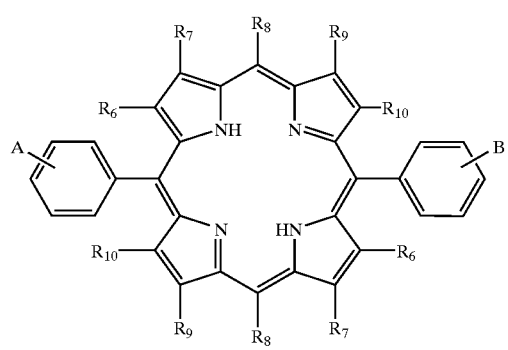

-continued

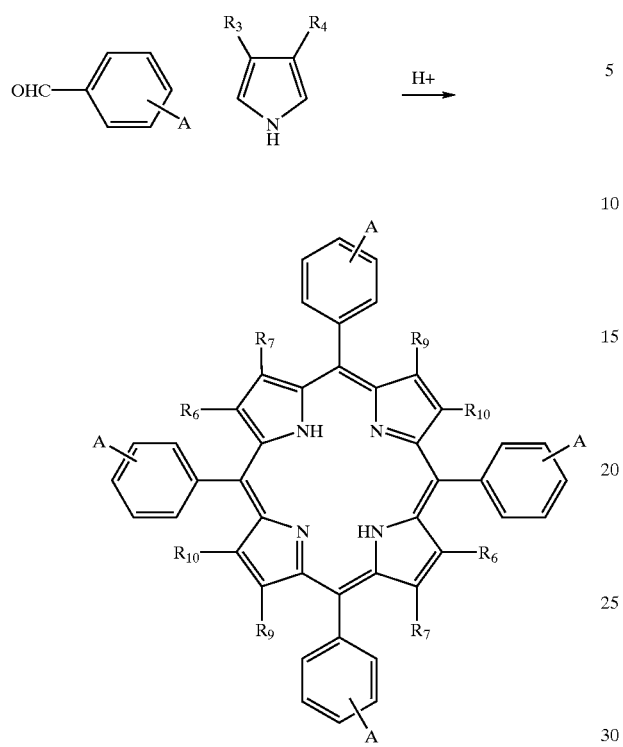

A second preferred class of compounds according to the invention are the mono-, di-, tri- and tetra-azaporphyrins. Schemes 3–7 outline the synthesis of mono-, di-, and tetra-azaporphyrins, examples of which are listed in Table 2.

Schemes 3–7 outline synthetic routes to novel tetrapyrrolic molecules that possess a linking group with terminal amine groups. Such compounds can be linked to a metal complexing reagent (MCR) and subsequently modified to be phototherapeutic and diagnostic compounds.

Scheme 3. Azaporphyrin Syntheses

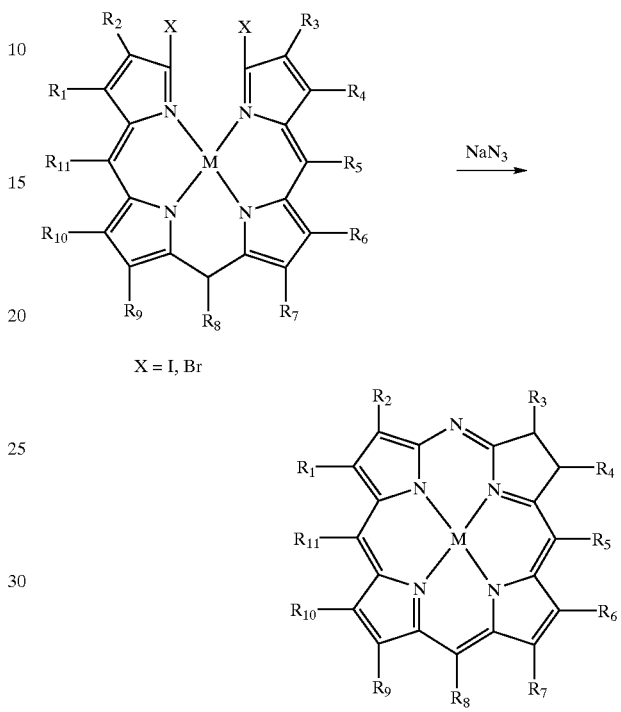

X = I, Br

TABLE 2

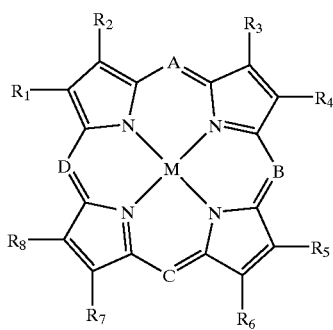

| Tetrapyrrole | A | B | C | D | $R_1$ | $R_2$ | $R_3$ | $R_4$ | $R_5$ | $R_6$ | $R_7$ | $R_8$ |
|---|---|---|---|---|---|---|---|---|---|---|---|---|
| 5-aza-coproporphyrin II | N | CH | CH | CH | Me | PO | PO | Me | Me | PO | PO | Me |
| 5-aza-protoporphyrin IX | N | CH | CH | CH | Me | V | V | Me | Me | PO | PO | Me |
| 5-aza-mesoporphyrin IX | N | CH | CH | CH | Me | Et | Me | Et | Me | PO | PO | Me |
| 5-aza-mesoporphyrin XIII | N | CH | CH | CH | Me | Et | Et | Me | Me | PO | PO | Me |
| 5-aza-uroporphyrin III | N | CH | CH | CH | PO | AO | PO | AO | PO | AO | AO | PO |
| 5-aza-isomesoporphyrin | N | CH | CH | CH | Et | Me | Me | Et | Me | PO | PO | Me |
| 5-aza-mesoporphyrin III | N | CH | CH | CH | Me | Et | Me | Et | PO | Me | Me | PO |
| 5,15-Diaza-coproporphyrin II | N | CH | N | CH | Me | PO | PO | Me | Me | PO | PO | Me |
| 5,15-diaza-mesoporphyrin III | N | CH | N | CH | Me | Et | Me | Et | PO | Me | Me | PO |

AO = —CH$_2$CO$_2$H; PO = —CH$_2$CH$_2$CO$_2$H, EO = —CH(OH)CH$_3$, EOE = —CH(OR)CH$_3$, Me = —CH$_3$, Et = CH$_2$CH$_3$, V = —CH=CH$_2$

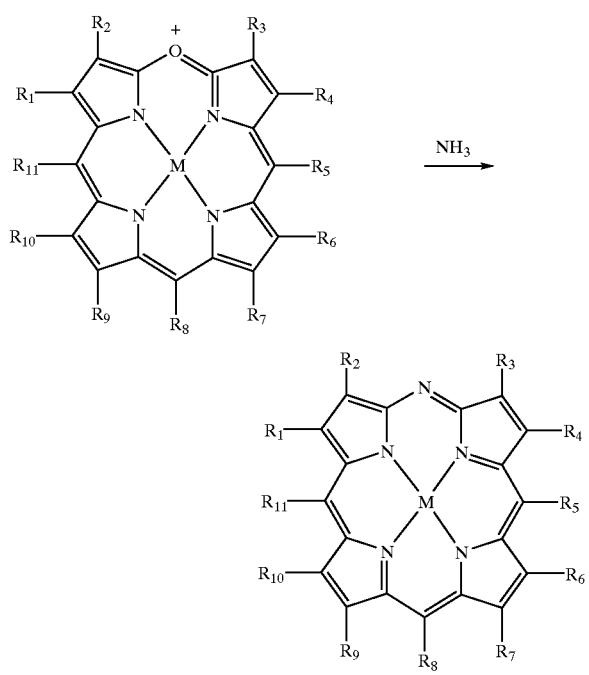

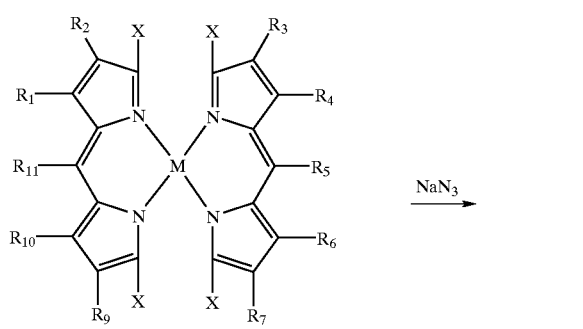

X = I, Br
M = Cu, 2H

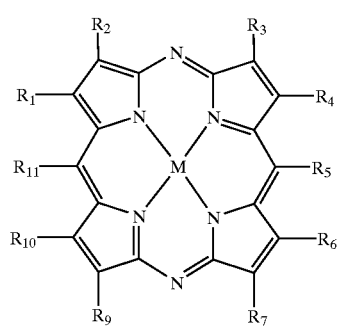

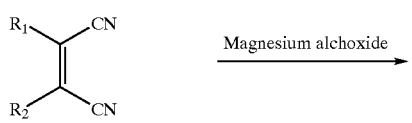

Magnesium alchoxide

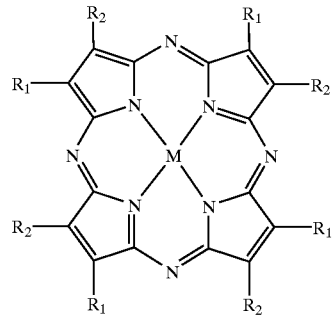

Mono-azaporphyrins are synthesized efficiently via the coupling of dibromobiladienes with sodium azide or via the reaction of oxyporphyrins with ammonia. Copper and metal free diazaporphyrins can be obtained via the coupling of 5,5'-dibromopyrromethenes with sodium azide. Tetra-azaporphyrins are synthesized most efficiently via the treatment of substituted maleonitriles with magnesium powder or magnesium alcoxides. Such reactions are well known in the art and are outlined in detail by N. Kobayashi in "The Porphyrin Handbook," K. M. Kadish, K. M. Smith, R. Guilard, Editors, Volume 2, Chapter 13, Academic Press, 2000, p. 301–360, the disclosure of which is hereby incorporated by reference herein.

The peripheral functionality of these compounds is important with respect to further derivatization to achieve the desired coupling to the metal complexing reagent (MCR) and the desired biological effect (both therapeutic and diagnostic). The types of peripheral functionality applicable to the invention are described in detail below. It is recognized that small changes in the peripheral functionality can have pronounced effects on the biological efficacy of the molecules as does metal co-ordination to the compounds. Schemes 4–7 outline synthetic routes to the novel tetrapyrrolic molecules of the invention.

The new compounds of the invention are based on the porphyrin, mono-, di-, tri- and tetra-azaporphyrin ring systems that bear peripheral functionality on the ring system. Such functionality includes esters, alcohols, amides, amines, ethers, and phosphates. Such derivatives may also have at least one hydroxylated residue present, or an amine group with which to couple the metal co-ordination compound. The new porphyrins themselves may be photodynamically active as metal free analogs and therefore useful as PDT agents. In addition, metallated derivatives of these compounds are also of particular interest for treatment and diagnosis of disorders of the cardiovascular system, normal or abnormal conditions of the hematological system, lymphatic reticuloendothelial system, nervous system, endocrine and exocrine system, skeletomuscular system including bone, connective tissue, cartilage and skeletal muscle, pulmonary system, gastrointestinal system including the liver, reproductive system, skin, immune system, cardiovascular system, urinary system, ocular system, auditory or olfactory system, where shorter wavelengths of light are necessary or advantageous to effect a desired therapy.

Scheme 4 outlines chemistry that has been undertaken to produce photosensitizing or diagnostic agents (based on non-naturally occuring porphyrin systems and azaporphyrins) that possess pendant terminal amine moieties and is exemplary only and is not intended to limit the invention. It should be noted that the functionality and position of the N and C meso atoms can be varied to produce analogs different from those shown. Additionally, the R groups in these schemes constitute functional groups that can be symmetrically substituted and can also, if desired, be modified by techniques known to those skilled in the art based on the chemistry described herein without departing from the spirit or scope of the invention.

Scheme 4. Modification of Porphyrin (X = CR$_5$) and azaporphyrin (X = N) compounds.

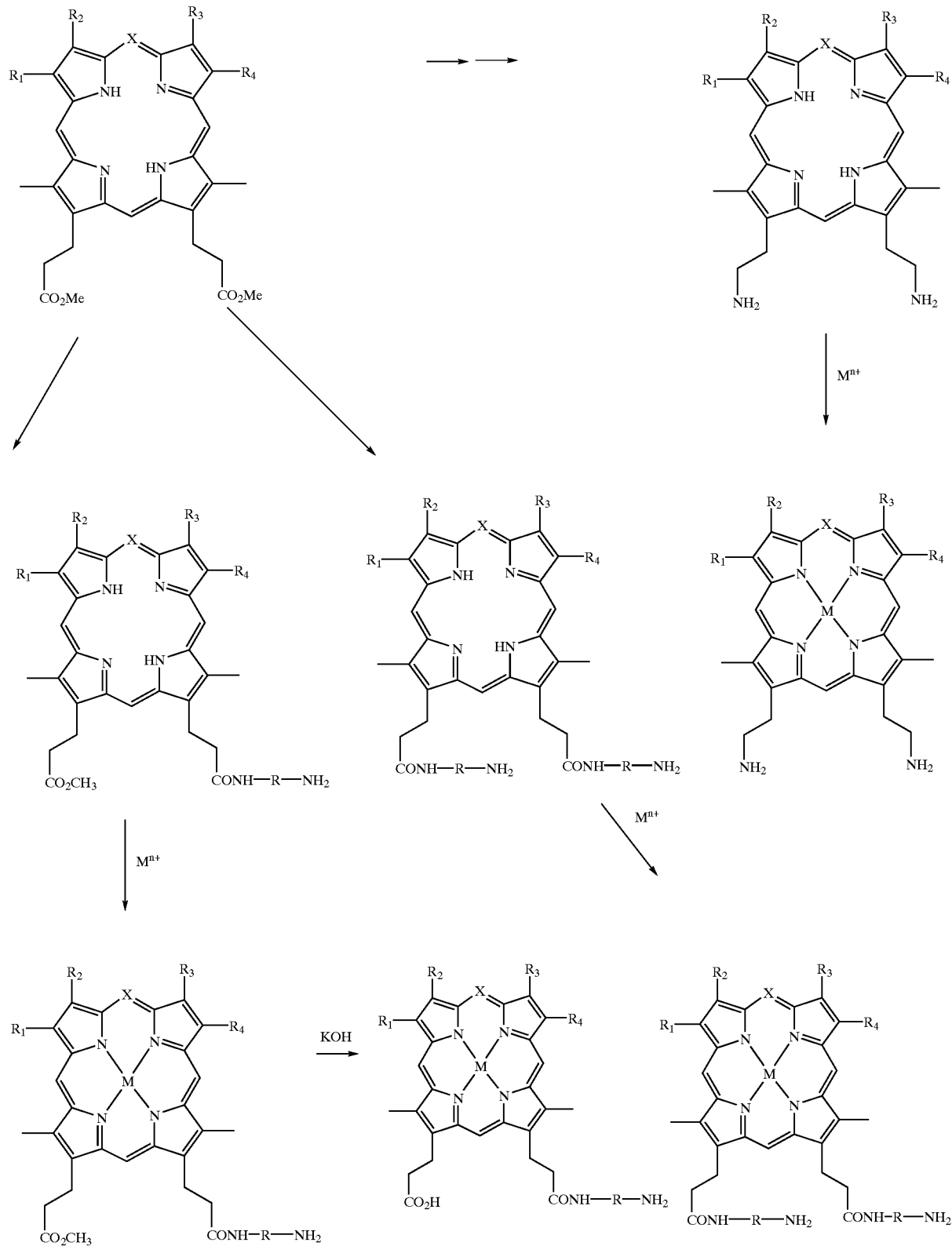

In scheme 4, the ester functionality of porphyrins or azaporphyrins can be hydrolyzed to yield both mono- and di-acid compounds. It is preferred that the synthesis of mono-acid compounds via this method occurs on compounds that are symmetrical in their substitution pattern of $R_1$–$R_4$, such that isomers are not formed. The mono- or di-acid can then be converted to the desired amide via standard techniques, to produce pendant arm groups with terminal amine moieties. Alternatively, if $R_5$ possesses a functional group that can be modified to produce a reactive linking moiety (for example $C_6H_4SO_3H$, $C_6H_4CO_2H$ and the like), these may alternatively be chemically modified to produce compounds with pendant arm groups having terminal amine moieties. Such compounds can, if desired, be reacted with metals to produce metallotetrapyrrolic complexes.

Scheme 5: Synthesis of amine porphyrins (X = CR_7) and azaporphyrins (X = N).

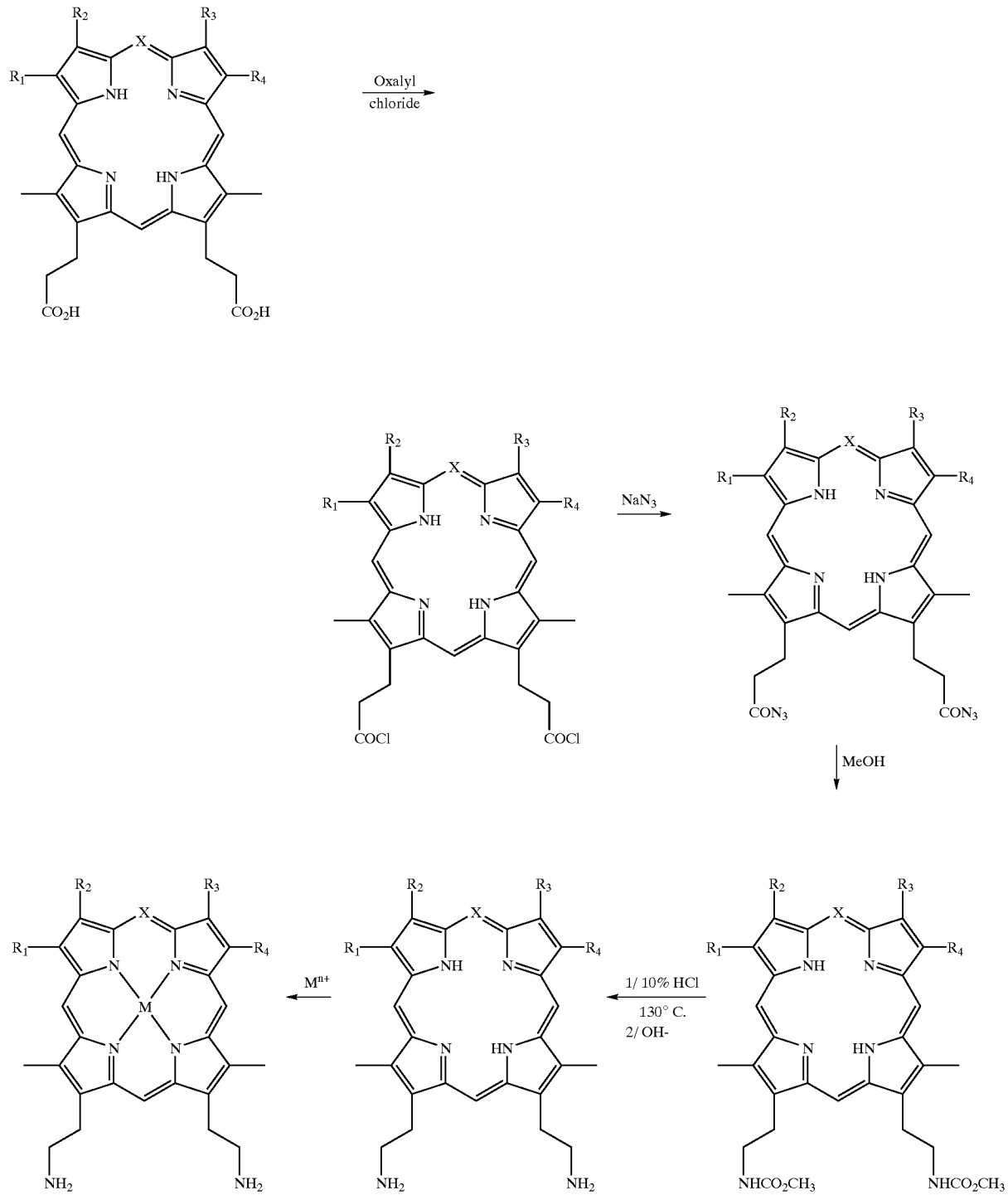

Scheme 6: Rhodoporphyrin and Pyrroporphyrin amine compounds.
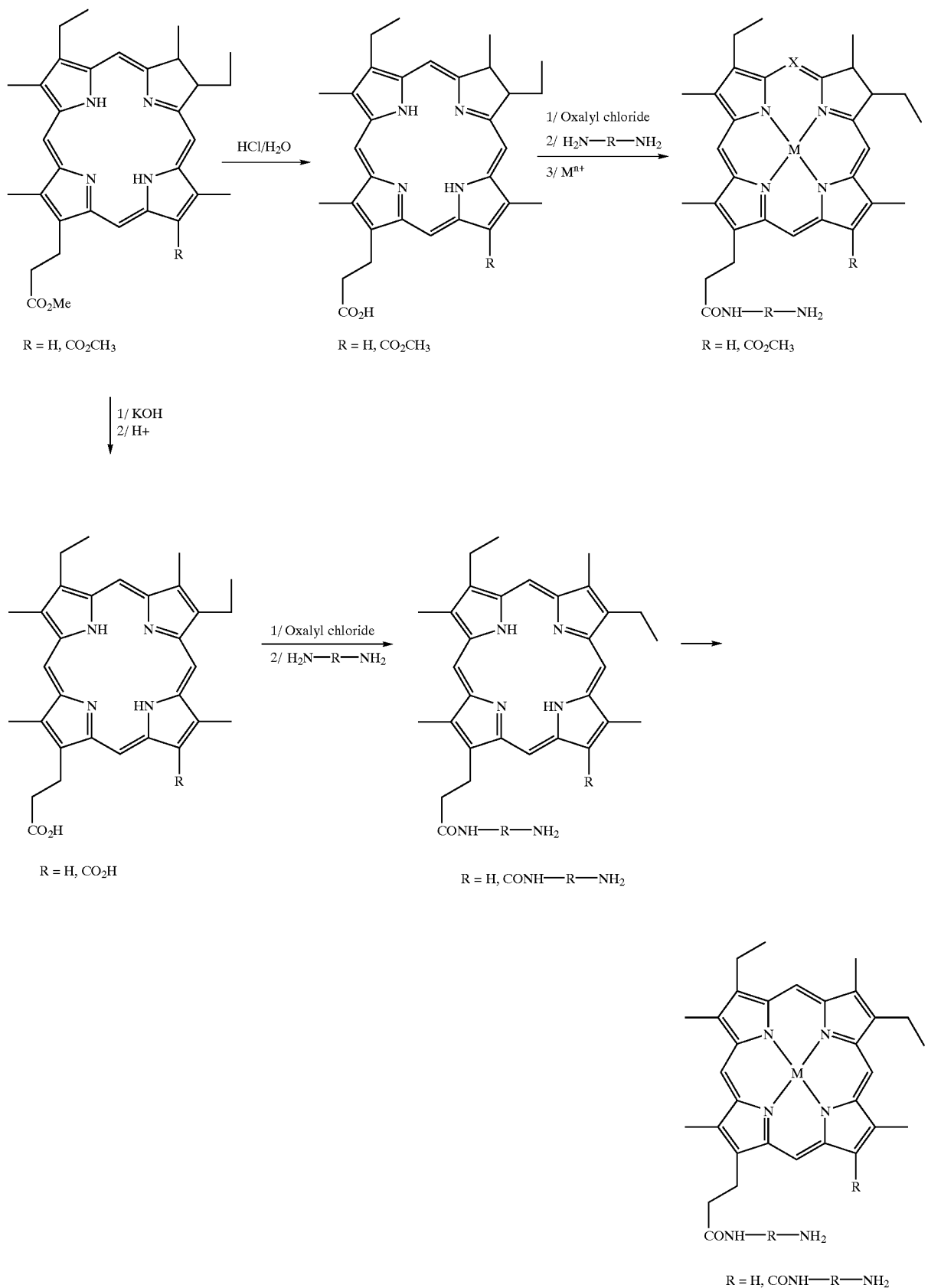

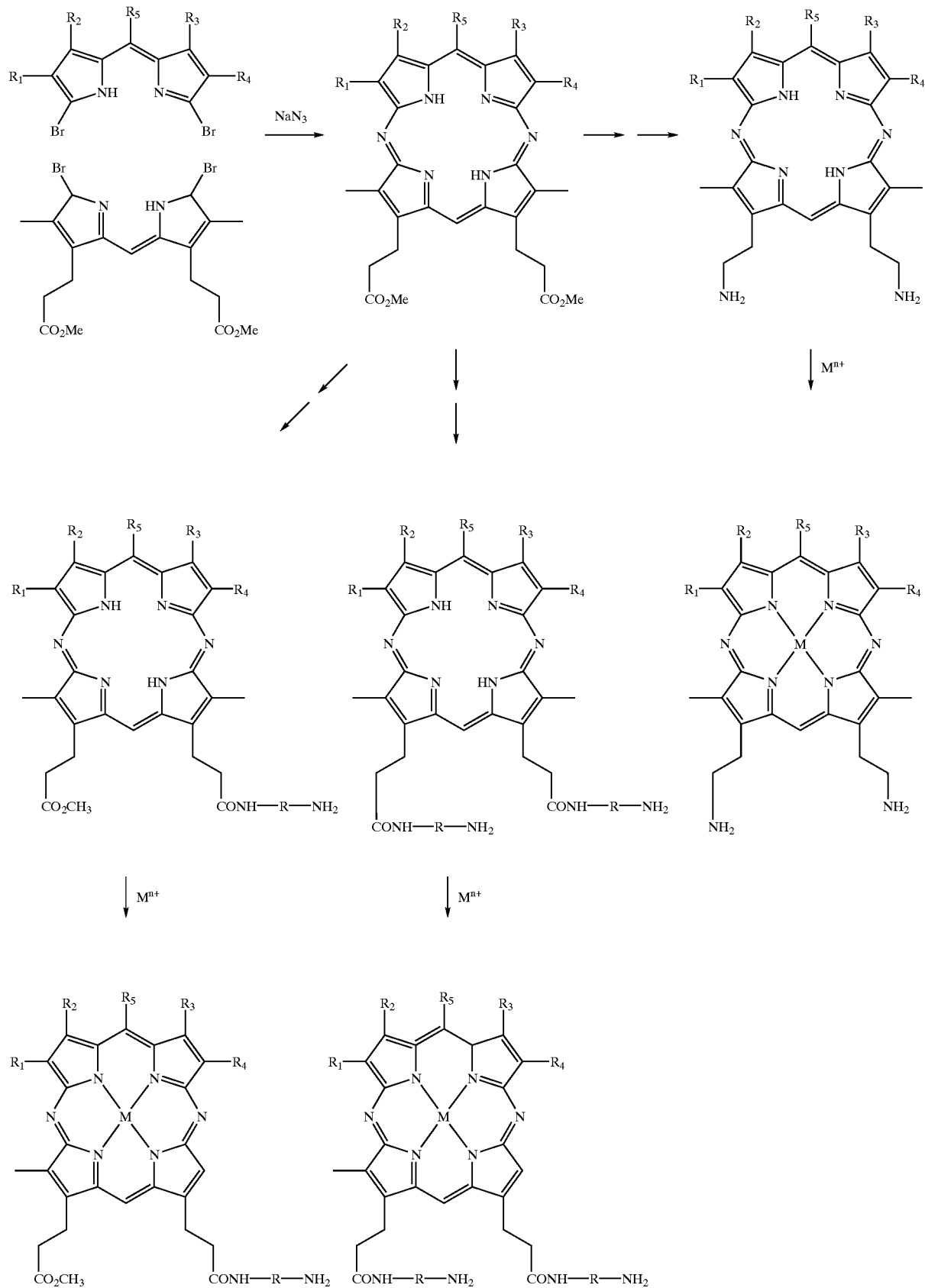
Scheme 7: Synthesis of amine linked di-azaporphyrins

Scheme 5 outlines the synthesis of porphyrins and azaporphyrins possessing two pendant arm terminal amine moieties. In this instance, the ester functionality of porphyrins or azaporphyrins can be hydrolyzed to yield di-acid compounds. The mono-or di-acid can then be converted to its di-acid chloride, which subsequently can be reacted with sodium azide in acetone to yield the di-azide compound. The di-azide then can be rearranged in methanol to give the di-urethane derivative, which can then be hydrolysed in acid to give protonated amine compounds. Neutralization with base yields the free amine compound. Such compounds can, if desired, be reacted with metals to produce metallo-tetrapyrrolic diamine complexes.

Scheme 6 outlines the synthesis route of metal-free or metallated mono- or di-amine porphyrins based on rhodoporphyrin or pyrroporphyrin. In the case of rhodoporphyrin ($R=CO_2Me$), it is possible to selectively hydrolyze the propionic acid ester with dilute HCl/water to give the mono acid derivative shown. Alternatively, both groups can be hydrolyzed with $KOH/H_2O$ to give the di-acid derivative. The acid groups can then be converted to the acid chloride derivatives and reacted with the appropriate amine to give compounds possessing one or two pendant arm terminal amine moieties. These compounds can, if desired, be reacted with metals to produce metallo-tetrapyrrolic mono or di-amine complexes.

Scheme 7 outlines the synthesis of metal-free or metallated mono or di-amine di-azaporphyrins. The di-azaporphyrins themselves can be synthesized via the coupling of appropriate brominated dipyrromethanes. Once synthesized, the peripheral functionality can be modified by similar chemistry as outlined in schemes 4 and 5. As before, it is preferred that if mono-amine functionalized compounds are to be made, $R_1$–$R_4$ should possess a symmetrical substitution pattern. This preference does not apply if di-amine substitution is desired.

The introduction of the desired metals (e.g., Zn, Ga, Al, Sn, In, Mg, Mn, Fe, etc) into the porphyrins or azaporphyrins can be carried out according to methods that are known in the literature (e.g., The Porphyrins, ed. D. Dolphin, Academic Press, New York 1980, Vol. V, p. 459; DE 4232925). In particular, metal substitution of pyrrolic NH's can be carried out by heating the metal-free ligand with the corresponding metal salt, preferably acetate or halide, optionally with the addition of acid-buffering agents, such as, for example, sodium acetate in a polar solvent. Alternatively, such substitutions can be carried out by metal exchange in which a metal that is already complexed by the porphyrin or azaporphyrin is displaced by the desired metal. An example of such a metal is cadmium. In this process, the preferred solvent is a polar solvent, such as, for example, methanol, glacial acetic acid, dimethylformamide, chloroform or water. In some instances where the metal is difficult to remove under acid conditions (Pt, Pd), it is more practical to generate the metalloporphyrin or metalloazaporphyrin compounds prior to modification to form the amine linking units. Additionally, the introduction of a diamagnetic or paramagnetic metal M into the porphyrin system can be carried out before or after linkage of the metal complexing agent radical (MCR). As a result, an especially flexible procedure for the synthesis of the compounds according to the invention is made possible.

The reaction of a metal-free or metallated porphyrin or azaporphyrin amine with a metal complexing agent (MCA) can be carried out according to methods that are known in the literature. Preferable MCA's include diethylenetriamine-pentaacetic acid and 1,4,7,10-tetraazacyclododecane-1,4,7-triacetic acid, which can be bonded via a linker to the respective porphyrin or azaporphyrin derivatives. See, e.g., DE 4232925 for IIa and IId; DE 19507822, DE 19580858 and DE 19507819 for IIb; U.S. Pat. No. 5,053,503, WO 96/02669, WO 96/01655, EP 0430863, EP 255471, U.S. Pat. No. 5,277,895, EP 0232751, and U.S. Pat. No. 4,885,363 for IIc and IIe.

In accordance with the invention, an activated MCR can be reacted with the amine porphyrin or azaporphyrin derivatives such that a covalent link between the two compounds occurs. As can be seen in schemes 4–7, the nature of the linking amine moiety on the porphyrins or azaporphyrins (P) to the MCR compounds may be varied. Preferable examples include: P—$(CH_2)_nNH_2$, where n is an integer from 1 to 10; P-(aryl)$NH_2$, P—$CONHNH_2$, or P—$(CH_2)_nCONHNH_2$, where n is an integer from 1 to 10; P—$CONH(CH_2)_nNH_2$, where n is an integer from 1 to 10; P—$CONH(CH_2)_2O(CH_2)_2NH_2$, or P—$CONH[(CH_2)_2]_nO_{n/2}[(CH_2)_2]_nNH_2$, where n is an integer from 1 to 10; P—$SO_2NHNH_2$, or P—$SO_2NH(CH_2)_nNH_2$, where n is an integer from 1 to 10; P—$SO_2NH(CH_2)_2O(CH_2)_2NH_2$, or P—$SO_2NH[(CH_2)_2]_nO_{n/2}[(CH_2)_2]_nNH_2$, where n is an integer from 1 to 10; P-(Aryl)-$SO_2NHNH_2$, or P-(Aryl)-$SO_2NH(CH_2)_nNH_2$, where n is an integer from 1 to 10; and P-(Aryl)-$SO_2NH(CH_2)_2O(CH_2)_2NH_2$, or P-(Aryl)-$SO_2NH[(CH_2)_2]_nO_{n/2}[(CH_2)_2]_nNH_2$, where n is an integer from 1 to 10. It would be apparent to those skilled in the art that other suitable linking amine units could be used in accordance with the teachings of the specification.

Alternatively, in accordance with the invention, porphyrin and azaporphyrin units can be generated that possess alcohol terminal linking groups. Preferred examples of such groups include P—$(CH_2)_nOH$, where n is an integer from 1 to 10; P-(aryl)OH, P—CONHOH, or P—$(CH_2)_nCONHOH$, where n is an integer from 1 to 10; P—$ONH(CH_2)_nOH$, where n is an integer from 1 to 10; P—$CONH(CH_2)_2O(CH_2)_2OH$, or P—$CONH[(CH_2)_2]_nO_{n/2}[(CH_2)_2]_nOH$, where n is an integer from 1 to 10; P—$SO_2NHOH$, or P—$SO_2NH(CH_2)_nOH$, where n is an integer from 1 to 10; P—$SO_2NH(CH_2)_2O(CH_2)_2OH$, or P—$SO_2NH[(CH_2)_2]_nO_{n/2}[(CH_2)_2]_nOH$, where n is an integer from 1 to 10; P-(Aryl)-$SO_2NHOH$, or P-(Aryl)-$SO_2NH(CH_2)_nOH$, where n is an integer from 1 to 10; P-(Aryl)-$SO_2NH(CH_2)_2O(CH_2)_2OH$, or P-(Aryl)-$SO_2NH[(CH_2)_2]_nO_{n/2}[(CH_2)_2]_nOH$, where n is an integer from 1 to 10; P—$CO_2(CH_2)_nOH$, where n is an integer from 1 to 10; P—$CO_2(CH_2)_2O(CH_2)_2OH$, or P—$CO_2[(CH_2)_2]_nO_{n/2}[(CH_2)_2]_nOH$, where n is an integer from 1 to 10; P—$SO_3(CH_2)_nOH$, where n is an integer from 1 to 10; P—$SO_3(CH_2)_2O(CH_2)_2OH$, or P—$SO_3[(CH_2)_2]_nO_{n/2}[(CH_2)_2]_nOH$, where n is an integer from 1 to 10; P-(Aryl)-$SO_3(CH_2)_nOH$, where n is an integer from 1 to 10; and P-(Aryl)-$SO_3(CH_2)_2O(CH_2)_2OH$, or P-(Aryl)-$SO_3[(CH_2)_2]_nO_{n/2}[(CH_2)_2]_nOH$, where n is an integer from 1 to 10. Such compounds can then be linked to the MCR group. It would be apparent to those skilled in the art that other suitable linking alcohol units or other reactive moieties can be used in accordance with the teachings of the specification.

The MCR linking group Q is an organic group that when linked to the amine or alcohol porphyrin or azaporphyrin results in a product that is an ester, an amide, an amine, an ether, or a thiolate. Preferable reactive MCR's are described in, for example, U.S. Pat. No. 4,885,363, U.S. Pat. No. 5,730,956, U.S. Pat. No. 6,136,841, and U.S. Pat. No. 5,275,801 the disclosures which are hereby incorporated herein by reference. Examples are illustrated in FIG. 2.

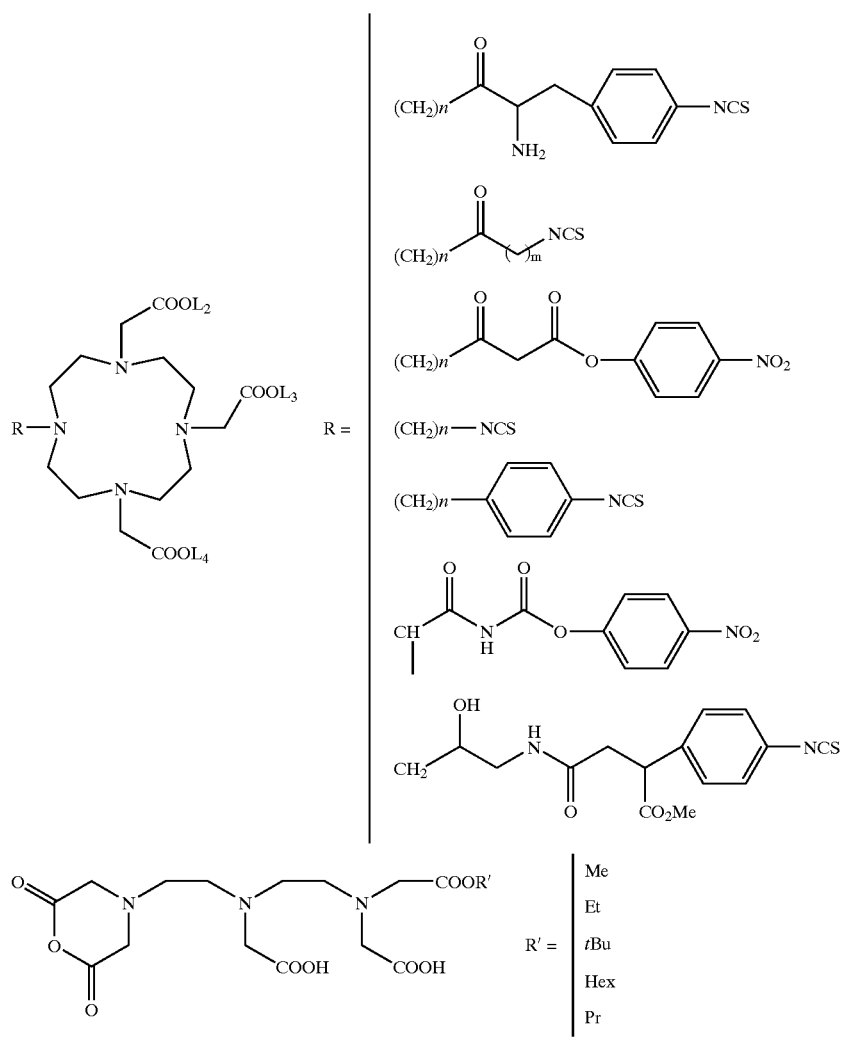

Examples of linker groups Q include —CO—, —CS—, —COCH₂NH—, —CO(CH₂)₂NH, —CO(CH₂)₂—, —COCH₂OC₆H₄CO, —COC₆H₄NH—, —COCH₂OCH₂NH—, —COC₆H₄—, —COCH₂NHCOCH₂CH(CH₂COOH)C₆H₄NH—, phenyleneoxy, a C1–C12 alkylene or a C7–C12 aralkylene group by one or more oxygen atoms. Obviously a large variety of linker groups are possible and it would be apparent to those skilled in the art that other suitable groups can be used in accordance with the teachings of the specification without deviating from the spirit of the invention.

In accordance with the invention, the porphyrin or azaporphyrin linked MCR compounds can then be modified to produce PDT/MRI radiodiagnostic compounds. If the compounds are to be used for NMR diagnosis, paramagnetic metal ions must be present in the complex. These are preferably divalent or trivalent ions of the elements of atomic numbers 21–29, 42–44 and 57–71. In this instance, the paramagnetic metal may be coordinated to either the inner pyrrolic core of the porphyrin or azaporphyrin, or in the MCR pendant arm, or in both. Suitable ions include, for example, chromium, gadolinium, dysprosium, manganese, iron, cobalt, cobalt, nickel, copper, praseodymium, neodymium, samarium, terbium, holmium, erbium and ytterbium ions. Because of their high magnetic moment, the gadolinium, dysprosium, manganese, terbium, holmium, erbium and iron ions are especially preferred.

For the use of the agents according to the invention for photodynamic therapy, the porphyrin or azaporphyrin compound should be metal free, i.e, M=2H, or should have coordinated photoactive metals, preferred examples of which include zinc, indium, gallium, tin, germanium, palladium, platinum, aluminum, silicon, ruthenium, yttrium, ytterbium, magnesium, lutetium, and cadmium.

For the use of the agents according to the invention in nuclear medicine, the metal ions must be radioactive. Examples that are suitable for the invention include radioisotopes of the elements copper, cobalt, gallium, zinc, germanium, yttrium, strontium, technetium, indium, ytterbium, gadolinium, samarium, thallium, and iridium. In this instance, the radioactive isotope may be coordinated to the porphyrin or azaporphyrin ligand or within the MCR, or both. Alternatively, such compounds can be modified such that they become active or excited using sonotherapy (e.g., M=gallium) or photothermally.

Metal chelation to the MCR group can be carried out by techniques known in the literature (see, e.g., DE3401052) by the metal oxide or metal salt (e.g., nitrate, acetate, carbonate, chloride or sulfate) of the metal that is desired. In each case the metal oxide or salt can be suspended or dissolved in polar solvents such as water or aqueous alcohols and then reacted with the corresponding amount of the complexing ligand. If desired, acidic hydrogen atoms or acid groups that are present can be substituted by cations of inorganic and/or organic bases or amino acids.

In accordance with the invention, neutralization can be carried out with the aid of inorganic bases, such as, e.g., alkali or alkaline-earth hydroxides, carbonates or bicarbonates and/or organic bases such as, for example, primary, secondary and tertiary amines, such as, e.g., ethanolamine, morpholine, glucamine, N-methyl- and N,N-dimethylglucamine, as well as basic amino acids, such as, e.g., lysine, arginine and ornithine or amides of originally neutral or acidic amino acids.

For the production of neutral complex compounds, a sufficient amount of the desired bases can be added to, for example, the acidic complex salts in aqueous solution or suspension to ensure that the neutral point is reached. The solution that is obtained can then be evaporated to the dry state in a vacuum. It is may be advantageous to precipitate the neutral salts that are formed by adding water-miscible solvents, such as, for example, lower alcohols (e.g., methanol, ethanol, isopropanol, acetonitrile), lower ketones (e.g., acetone), polar ethers (e.g., tetrahydrofuran, dioxane, 1,2-dimethoxyethane) and thus to obtain easily isolated and readily purified crystallizates. It has proven especially advantageous to add the desired base as early as during the complexing of the reaction mixture and thus eliminate a process step.

If the acidic complex compounds contain several free acid groups, it is often advantageous to produce neutral mixed salts that contain both inorganic and organic cations as counter-ions. This can be achieved, for example, by reacting the complexing ligands in aqueous suspension or solution with the oxide or salt of the element that yields the central ion and half of the amount of an organic base that is required for neutralization. The complex salt that is formed can then be isolated, optionally purified, and then mixed for complete neutralization with the required amount of inorganic base. The sequence in which the base is added can also be reversed. Another way of obtaining neutral complex compounds consists of converting the remaining acid groups in the complex completely or partially into esters. This can be achieved by subsequent reaction on the finished complex, e.g., by exhaustive reaction of free carboxy groups with dimethylsulfate.

Pharmaceutical agents of the invention can be produced by adding to the complex compounds of the invention certain additives that are commonly used in the pharmaceutical industry to suspend or dissolve the compounds in an aqueous medium, and then the suspension or solution can be sterilized by techniques known in the art. Suitable additives include, for example, physiologically harmless buffers (such as, e.g., trimethamine), small additions of complexing agents (such as, e.g., diethylenetriaminepentaacetic acid) or, if necessary, electrolytes such as, e.g., sodium chloride or antioxidants such as, e.g., ascorbic acid, butylate hydroxy toluene, or tocopherol.

If suspensions or solutions of the agents according to the invention in water or in physiological salt solution are desired for enteral administration or other purposes, they can be mixed with one or more adjuvants that are commonly used in galenicals (e.g., methylcellulose, lactose, mannitol) and/or surfactant(s) (e.g., lecithins, Tween, and/or flavoring substances for taste correction (e.g., ethereal oils).

In principle, it is possible to produce the pharmaceutical agents according to the invention even without isolating the complex salt. In any case, special care must be taken to perform the chelation such that the salts and salt solutions according to the invention are virtually free of noncomplexed metal ions that may have a toxic effect. This can be ensured, for example, by the use of color indicators such as xylenol orange by control titrations during the production process. As a final precaution, there remains purification of the isolated complex salt.

To avoid undesirable photoreactions of porphyrins and azaporphyrins, the compounds and agents according to the invention should be stored and handled as much as possible in a light-free environment.

The pharmaceutical agents according to the invention preferably contain from about 20 $\mu$mol/L to about 200 mmol/L of the complex salt and are generally dosed in amounts of 0.01 $\mu$mol to 2 mmol/kg of body weight, both for their use in PDT and for therapy monitoring using MRI diagnosis. They are intended for enteral and parenteral administration or are administered with the methods of interventional radiology.

The agents according to the invention are especially suitable for PDT and as MRI contrast media. After administration, they can enhance the informational value of the image that is obtained from a nuclear spin tomograph by increasing the signal intensity. They are effective without burdening the body with large amounts of foreign substances.

The high water-solubility of the agents according to the invention allows the production of highly concentrated solutions, so as to keep the volume burden of the circulation within acceptable limits and to compensate for dilution by bodily fluid. In addition, the agents according to the invention show not only a high stability in vitro but also a surprisingly high stability in vivo, so that a release or an exchange of the ions, which are inherently toxic and not covalently bonded in the complexes, will not be harmful within the time that it takes for the contrast media to be completely excreted.

Similar reactions can be undertaken on tetrapyrrolic molecules in which more than two carboxylic acid functionalities are present, for example, those compounds shown in Tables 1 and 2. Such reactions on mono-, di- and tetraazaporphyrin compounds are particularly preferred because metallo-derivatives of such compounds have larger molar extinction co-efficents than the porphyrins in the green and yellow region, and thus theoretically may be more efficient photosensitizers as a larger cross-sectional area of light may be absorbed. While the specification describes several chemical modifications to the tetrapyrrolic compounds, those skilled in the art would know that additional modifications can be made to the tetrapyrrolic ring systems in accordance with the teachings of the specification.

The scope of the present invention is not limited to the specific disclosure provided herein. As shown by the above disclosure, any porphyrinic molecule may be modified according to the invention to form the desired photoactive compounds with widely differing functionality as described in the literature (for example see "Porphyrins and Metalloporphyrins" Ed. K. Smith, Elsevier, 1975, N.Y., "The Porphyrins", Ed. D. Dolphin, Vol I–V, Academic Press, 1978, and "The Porphyrin Handbook", Eds. K. Kadish, K. M. Smith, R. Guilard, Academic Press, 2000). These compounds contain various and ranging substituents on the β-pyrrole positions or meso-positions of the porphyrin ring, either symmetrically or asymmetrically substituted on the ring.

Examples of such functionality include functional groups having a molecular weight less than about 100,000 daltons and can be a biologically active group or organic. Examples include, but are not limited to: (1) hydrogen; (2) halogen, such as fluoro, chloro, iodo and bromo (3) lower alkyl, such as methyl, ethyl, n-propyl, butyl, hexyl, heptyl, octyl, isopropyl, t-butyl, n-pentyl and the like groups; (4) lower alkoxy, such as methoxy, ethoxy, isopropoxy, n-butoxy, t-pentoxy and the like; (5) hydroxy; (6) carboxylic acid or acid salts, such as —$CH_2COOH$, —$CH_2COONa$, —$CH_2CH_2COOH$, —$CH_2CH_2COONa$, —$CH_2CH_2CH(Br)COOH$, —$CH_2CH_2CH(CH_3)COOH$, —$CH_2CH(Br)COOH$, —$CH_2CH(CH_3)COOH$, —$CH(Cl)CH_2CH(CH_3)COOH$, —$CH_2CH_2C(CH_3)_2COOH$, —$CH_2CH_2C(CH_3)_2COOK$, —$CH_2CH_2CH_2CH_2COOH$, $C(CH_3)_2COOH$, $CH(Cl)_2COOH$ and the like; (7) carboxylic acid esters, such as —$CH_2CH_2COOCH_3$, —$CH_2CH_2COOCH_2CH_3$, —$CH_2CH(CH_3)COOCH_2CH_3$, —$CH_2CH_2COOCH_2CH_2CH_3$, —$CH_2CH_2CH_2COOCH_2CH_2CH_3$, —$CH_2CH(CH_3)COOCH_2CH_3$, —$CH_2CH_2COOCH_2CH_2OH$, —$CH_2CH_2COOCH_2CH_2N(CH_3)_2$ and the like, particularly halogenated alkyl esters; (8) sulfonic acid or acid salts, for example, group I and group 11 salts, ammonium salts, and organic cation salts such as alkyl and quaternary ammonium salts; (9) sulfonylamides such as —$SO_2NH(alkyl)$, —$SO_2N(alkyl)_2$, —$SO_2NH(alkyl-OH)$, —$SO_2N(alkyl-OH)_2$, —$SO_2NH(alkyl)-N(alkyl)_2$, —$SO_2N(alkyl-N(alkyl)_2)_2$, $SO_2(NH(alkyl)-N(alkyl)_3{}^+Z^-)$ and the like, wherein $Z^-$ is a counterion, —$SO_2NHCH_2CO_2H$, substituted and unsubstituted benzene sulfonamides and sulfonylamides of aminoacids and the like; (10) sulfonic acid esters, such as $SO_3(alkyl)$, $SO_3(alkyl-OH)$, $SO_3(alkyl-N(alkyl)_2)$, $SO_3(alkyl-N(alkyl)_3{}^+Z^-)$ and the like, wherein $Z^-$ is a counterion, $SO_3CH_2CO_2H$, and the like; (11) amino, such as unsubstituted or substituted primary amino, methylamino, ethylamino, n-propylamino, isopropylamino, butylamino, sec-butylamino, dimethylamino, trimethylamino, diethylamino, triethylamino, di-n-propylamino, methylethylamino, dimethyl-sec-butylamino, 2-aminoethoxy, ethylenediamino, cyclohexylamino, benzylamino, phenylethylamino, anilino, N-methylanilino, N,N-dimethylanilino, N-methyl-N-ethylanilino, 3,5-dibromo-4-anilino, p-toluidino, diphenylamino, 4,4'-dinitrodiphenylamino and the like; (12) cyano; (13) nitro; (14) a biologically active group; (15) amides, such as —$CH_2CH_2CONHCH_3$, —$CH_2CH_2CONHCH_2CH_3$, —$CH_2CH_2CON(CH_3)_2$, —$CH_2CH_2CON(CH_2CH_3)_2$, —$CH_2CONHCH_3$, —$CH_2CONHCH_2CH_3$, —$CH_2CON(CH_3)_2$, —$CH_2CON(CH_2CH_3)_2$, —$CH_2CH_2CONHSO_2CH_3$; (16) iminium salts, for example $CH=N(CH_3)_2{}^+Z^-$ and the like, wherein $Z^-$ is a counterion); (17) boron containing complexes; (18) carbon cage complexes (e.g., C20 and the like); (19) polyfunctional carboxylic acid groups and their metal cluster complexes, for example metal complexes of polyfunctional carboxylic acid moieties such as of EDTA, DTPA, EGTA, crown ethers, cyclams, cyclens, and the like; (20) other porphyrin, chlorin, bacteriochlorin, isobacteriochlorin, azaporphyrin, tetraazaporphyrin, phthalocyanine, naphthalocyanine, texaphyrins, tetrapyrrolic macrocycles or dye molecules and the like; (21) alkynyl, including alkyl, aryl, acid and heteroatom substituted alkynes; (22) leaving or protecting groups; (23) aromatic ring systems (aryl), such as substituted phenyls, napthalenes, anthracenes, benzopyrenes, quinolines, benzoquinolines, benzoperylene, benzofluorenes, fluorenes, benzofurazans, benzodiphenylenes, benzofluoranthenes, benzanthracenes, benzacephenanthrylenes, bathophenanthrolines, indans, benzoquinolines, quinolines, pyrazines, quinolines, quinazoles, quinoxalines, imidazopyridines, indenes, indolines, thiazolines, bezopyrimidines, pyrimidines, benzimidazole, triazolopyrimidines, pyrazoles, tryptophans, phenanthrolines, benzooxadiazoles, benzoselenadiazole, benzocoumarins, chalcones, fluoranthenes, pyridoindoles, pentacenes, perylenes, phenatholines, phenazines, phenoxazines, phenoxathiins, phenothiazines, pyrroles, thiophenes, or heteroaromatics containing 5, 6, 7, 8, membered ring systems; 24) —NHCS groups or any other substituent that increases the hydrophilic, amphiphilic or lipophilic nature or stability of the compounds. It is recognized that such groups can affect the biological activity of the compounds in vivo.

The term "biologically active group" can be any group that selectively promotes the accumulation, elimination, binding rate, or tightness of binding in a particular biological environment. For example, one category of biologically active groups is the substituents derived from sugars, specifically: (1) aldoses such as glyceraldehyde, erythrose, threose, ribose, arabinose, xylose, lyxose, allose, altrose, glucose, mannose, gulose, idose, galactose, and talose; (2) ketoses such as hydroxyacetone, erythrulose, rebulose, xylulose, psicose, fructose, sorbose, and tagatose; (3) pyranoses such as glucopyranose; (4) furanoses such as fructofuranose; (5) O-acyl derivatives such as penta-O-acetyl-α-glucose; (6) O-methyl derivatives such as methyl α-glucoside, methyl β-glucoside, methyl α-glucopyranoside, and methyl-2,3,4,6-tetra-O-methyl-glucopyranoside; (7) phenylosazones such as glucose phenylosazone; (8) sugar alcohols such as sorbitol, mannitol, glycerol, and myo-inositol; (9) sugar acids such as gluconic acid, glucaric acid and glucuronic acid, 8-gluconolactone, 8-glucuronolactone, ascorbic acid, and dehydroascorbic acid; (10) phosphoric acid esters such as α-glucose 1-phosphoric acid, α-glucose 6-phosphoric acid, α-fructose 1,6-diphosphoric acid, and α-fructose 6-phosphoric acid; (11) deoxy sugars such as 2-deoxy-ribose, rhammose (deoxy-mannose), and fructose (6-deoxy-galactose); (12) amino sugars such as glucosamine and galactosamine; muramic acid and neurarninic acid; (13) disaccharides such as maltose, sucrose and trehalose; (14) trisaccharides such as raffinose (fructose, glucose, galactose) and melezitose (glucose, fructose, glucose); (15) polysaccharides (glycans) such as glucans and mannans; and (16) storage polysaccharides such as α-amylose, amylopectin, dextrins, and dextrans.

Amino acid derivatives are also useful biologically active substituents, such as those derived from valine, leucine, isoleucine, threonine, methionine, phenylalanine, tryptophan, alanine, arginine, aspartic acid, cystine, cysteine, glutamic acid, glycine, histidine, proline, serine, tyrosine, asparagine and glutamine. Also useful are peptides, particularly those known to have affinity for specific receptors, for example, oxytocin, vasopressin, bradykinin, LHRH, thrombin and the like.

Another useful group of biologically active substituents are those derived from nucleosides, for example, ribonucleosides such as adenosine, guanosine, cytidine, and uridine; and 2'-deoxyribonucleosides, such as 2'-deoxyadenosine, 2'-deoxyguanosine, 2'-deoxycytidine, and 2'-deoxythymidine.

Another category of biologically active groups that is particularly useful is any ligand that is specific for a particular biological receptor. The term "ligand specific for a biological receptor" refers to a moiety that binds a receptor at cell surfaces, and thus contains contours and charge patterns that are complementary to those of the biological receptor. The ligand is not the receptor itself, but a substance complementary to it. It is well understood that a wide variety of cell types have specific receptors designed to bind hormones, growth factors, or neurotransmitters. However, while these embodiments of ligands specific for receptors are known and understood, the phrase "ligand specific for a biological receptor", as used herein, refers to any substance, natural or synthetic, that binds specifically to a receptor.

Examples of such ligands include: (1) the steroid hormones, such as progesterone, estrogens, androgens, and the adrenal cortical hormones; (2) growth factors, such as epidermal growth factor, nerve growth factor, fibroblast growth factor, and the like; (3) other protein hormones, such as human growth hormone, parathyroid hormone, and the like; (4) neurotransmitters, such as acetylcholine, serotonin, dopamine, and the like; and (5) antibodies. Any analog of these substances that also succeeds in binding to a biological receptor is also included within the invention.

Particularly useful examples of substituents tending to increase the amphiphilic nature of the compounds include, but are not limited to: (1) short or long chain alcohols, such as, for example, —$C_{12}H_{24}$—OH; (2) fatty acids and their salts, such as, for example, the sodium salt of the long-chain fatty acid oleic acid; (3) phosphoglycerides, such as, for example, phosphatidic acid, phosphatidyl ethanolamine, phosphatidyl choline, phosphatidyl serine, phosphatidyl inositol, phosphatidyl glycerol, phosphatidyl 3'-O-alanyl glycerol, cardiolipin, or phosphatidyl choline; (4) sphingolipids, such as, for example, sphingomyelin; and (5) glycolipids, such as, for example, glycosyldiacylglycerols, cerebrosides, sulfate esters of cerebrosides or gangliosides. It would be known to those skilled in the art what other substituents, or combinations of the subsituents described, would be suitable for use in the invention.

The compounds of the present invention, or their pharmaceutically acceptable salts, solvates, prodrugs, or metabolites, can be administered to the host in a variety of forms adapted to the chosen route of administration, e.g., orally, intravenously, topically, intramuscularly or subcutaneously.

The active compound may be orally administered, for example, with an inert diluent or with an assimilable edible carrier, or it may be enclosed in hard or soft shell gelatin capsule, or it may be compressed into tablets, or it may be incorporated directly with food. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may, for example, conveniently be between about 2 to about 60% of the weight of the administered product. The amount of active compound in such therapeutically useful compositions is can be selected so that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions, dispersions, or liposomal or emulsion formulations. In all cases the form must be sterile and should be fluid to enable administration by a syringe. The form must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use of agents delaying absorption, for example, aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required additional ingredients from those enumerated above. In the case of sterile powders for the preparation of sterile injectable solutions, the preferred methods of preparation are vacuum drying and the freeze-drying technique, which yield a powder of the active ingredient plus any additional desired ingredient from previously sterile-filtered solutions thereof.

The new compounds of the invention may also be applied directly to tumors in the host whether internal or external, in topical compositions. Exemplary compositions include solutions of the new compounds in solvents, particularly aqueous solvents, most preferably water. Alternatively, for topical application particularly to skin tumors or psoriasis, the present new compounds may be dispersed in the usual cream or salve formulations commonly used for this purpose (such as liposomes, ointments, gels, hydrogels, cremes and oils) or may be provided in the form of spray solutions or suspensions that may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Any conventional media or agent that is compatible with the active ingredient can be used in the therapeutic compositions of the invention. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated. Each unit contains a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of cardiovascular diseases, diseases of the skin, cancers and other superficial disease conditions in living subjects.

The present invention provides a method of treating live cells, which includes, but is not limited to, animals such as humans and other mammals. The "mammals" also include farm animals, such as cows, hogs and sheep, as well as pet or sport animals, such as horses, dogs and cats. The dosage of the pharmaceutical compositions of the invention is dependent on the method of administration, the patient's age, severity of the disease, and the like.

The compounds of the invention may be taken parentally or orally, generally being administered intravascularly, subcutaneously, or intramuscularly or interperitoneally. The subject compounds may also be administered by inhalation, perivascular delivery, pericardial delivery (into perivascular sac), periadvential delivery (e.g., using a hydrogel wrap around the vessel), endovascular balloon catheters with micropores, channels, transmural injection ports, and the like.

For local catheter-based delivery of the compounds of the invention, an infusate can be placed and pressurized to facilitate intramural and transmural penetration into the target vessel. Local delivery can also be enhanced by other mechanical and electrical means. The depth of the penetration of the subject compounds by this local delivery method is a function of pressure in the perfused segment and the dwell time. Although little attention has been paid to the quantitative characteristics of the compounds of the invention in this setting, deposition of the substance should obey the principles governing transmural convection and diffusion.

Delivery of the compounds of the invention may also be via antibody-drug conjugates, internalizing antibodies or antibody fragments conjugated to compounds into cells using endocytosis. The subject compounds may also be impregnated into stent struts for local delivery. The route of administration of these pharmaceutical preparations is not critical, but may be selected according to the dosage form, the patient's age, the severity of the disease to be treated and other factors.

The compounds of the invention may find use in conjunction with other interventions, diagnostics and therapies, where lower levels of other therapies having significant side effects may be used effectively to reduce the detrimental side effects. Adjunctive interventions may include, but are not limited to: balloon angioplasty, invasive and non-invasive surgical procedures, stent deployment, cutting balloons, embolic protection devices, rotational and directional atherectomy, eximer lasers and the like.

Adjunctive therapies may include, but are not limited to radiation therapy, chemotherapy, anti-platelet agents, vasodilators, antihypertensives, antiarrhythmics, hyperthermia, cryotherapy, magnetic force, viral and non-viral gene therapy, pharmacogenetic therapy, antibodies, vaccines, glycoprotein IIb/IIIa Inhibitors, growth factors, peptides, DNA delivery, nucleic acids, anticancer drugs, steroid hormones, anti-inflammatories, proteins, anti-apoptotic therapies, anti-sense agents, immunotoxins, immunomodulators, antibody-drug conjugates, antiproliferative therapies, drug eluting stents containing pharmacologically active agents, transplant products and processes, prostaglandins and catheter based devices to detect vulnerable plaques, hormone products, chelating agents, diuretics, cardiac glycosides, bronchodilators, antibiotics, antivirals, antitioxins, cyclosporins, thrombolytic agents, interferons, blood products such as parental iron and hemin, anti-fungal agents, antianginals, anticoagulants, analgesics, narcotics, neuromuscular blockers, sedatives, bacterial vaccines, viral vaccines, DNA or RNA of natural or synthetic origin including recombinant RNA and DNA, cytokines and their antagonists/inhibitors, chemokines and their antagonists/inhibitors, Adjunctive diagnostics may include, but are not limited to: intravascular ultrasound imaging, angiography, quantitative vessel measurements and the use of radiological contrast agents, hormone products, chelating agents, diuretics, cardiac glycosides, bronchodilators, antibiotics, antivirals, antitoxins, cyclosporins, thrombolytic agents, interferons, blood products such as parental iron and hemin, anti-fungal agents, antianginals, anticoagulants, analgesics, narcotics, neuromuscular blockers, sedatives, bacterial vaccines, viral vaccines, DNA or RNA of natural or synthetic origin including recombinant RNA and DNA, cytokines and their antagonists/inhibitors, and chemokines and their antagonists/inhibitors.

Definitions

As used in the present application, the following definitions apply:

The term "alkyl" as used herein refers to substituted or unsubstituted, straight or branched chain groups, preferably having one to twenty, more preferably having one to six, and most preferably having from one to four carbon atoms. The term "$C_1$–$C_{20}$ alkyl" represents a straight or branched alkyl chain having from one to twenty carbon atoms. Exemplary $C_1$–$C_{20}$ alkyl groups include methyl, ethyl, n-propyl, isopropyl, butyl, isobutyl, sec-butyl, t-butyl, pentyl, neopentyl, hexyl, isohexyl, and the like. The term "$C_1$–$C_{20}$ alkyl" includes within its definition the term "$C_1$–$C_4$ alkyl". Such alkyl groups may themselves be ethers or thioethers, or aminoethers or dendrimers.

The term "cycloalkyl" represents a substituted or unsubstituted, saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "aryl" as used herein refers to an aromatic, monovalent monocyclic, bicyclic, or tricyclic radical containing 6, 10, 14, or 18 carbon ring atoms, which may be unsubstituted or substituted, and to which may be fused one or more cycloalkyl groups, heterocycloalkyl groups, or heteroaryl groups, which themselves may be unsubstituted or substituted by one or more suitable substituents. Illustrative examples of aryl groups include, but are not limited to, phenyl, napthalenes, anthracenes, benzopyrenes, quinolines, benzoquinolines, benzoperylene, benzofluorenes, fluorenes, benzofurazans, benzodiphenylenes, benzofluoranthenes, benzanthracenes, benzacephenanthrylenes, bathophenanthrolines, indans, benzoquinolines, quinolines, pyrazines, quinolines, quinazoles, quinoxalines, imidazopyridines, indenes, indolines, thiazolines, benzopyrimidines, pyrimidines, benzimidazole, triazolopyrimidines, pyrazoles, tryptophans, phenanthrolines, benzooxadiazoles, benzoselenadiazole, benzocoumarins, chalcones, fluoranthenes, pyridoindoles, pentacenes, perylenes, phenatholines, phenazines, phenoxazines, phenoxathiins, phenothiazines ad the like.

The term "halogen" represents chlorine, fluorine, bromine or iodine. The term "halocarbon" or "haloalkyl" represents one or more halogens bonded to a one or more carbon bearing groups. The term "heterohaloalkyl" represents for example halogenated alkylethers, halogenated alkyl amines, halogenated alkyl esters, halogenated alkyl amides, halogenated alkyl thioesters, halogenated alkyl thiols, where N, S, O, P atoms are present in the haloalkylated structure. The term heteroalkyl represents for example ethers, alkylamines, alkylated thiols and alkylate phosphorus containing groups.

The term "carbocycle" represents a substituted or unsubstituted aromatic or a saturated or a partially saturated 5–14 membered monocyclic or polycyclic ring, such as a 5- to 7-membered monocyclic or 7- to 10-membered bicyclic ring, wherein all the ring members are carbon atoms.

The term "electron withdrawing group" is intended to mean a chemical group containing an electronegative element such as halogen, sulfur, nitrogen or oxygen.

A "heterocycloalkyl group" is intended to mean a non-aromatic, monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulfur, wherein the radical is unsubstituted or substituted, and to which may be fused one or more cycloalkyl groups, aryl groups, or heteroaryl groups, which themselves may be unsubstituted or substituted. Illustrative examples of heterocycloalkyl groups include, but are not limited to azetidinyl, pyrrolidyl, piperidyl, piperazinyl, morpholinyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

A "heteroaryl group" is intended to mean an aromatic monovalent monocyclic, bicyclic, or tricyclic radical containing 5, 6, 7, 8, 9, 10, 11, 12, 13, 14, 15, 16, 17, or 18 ring atoms, including 1, 2, 3, 4, or 5 heteroatoms selected from nitrogen, oxygen and sulfur, which may be unsubstituted or substituted, and to which may be fused one or more cycloalkyl groups, heterocycloalkyl groups, or aryl groups, which themselves may be unsubstituted or substituted. Illustrative examples of heteroaryl groups include, but are not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b] thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl and the like.

The term "leaving group" as used herein refers to any group that departs from a molecule in a substitution reaction by breakage of a bond. Examples of leaving groups include, but are not limited to, halides, tosylates, arenesulfonates, alkylsulfonates, and triflates.

Suitable protecting groups are recognizable to those skilled in the art. Examples of suitable protecting groups can be found in T. Green & P. Wuts, *Protective Groups in Organic Synthesis* (2d ed. 1991), which is hereby incorporated by reference herein in its entirety.

Suitable salt anions include, but are not limited to, inorganics such as halogens, pseudohalogens, sulfates, hydrogen sulfates, nitrates, hydroxides, phosphates, hydrogen phosphates, dihydrogen phosphates, perchlorates, and related complex inorganic anions; and organics such as carboxylates, sulfonates, bicarbonates and carbonates.

Examples of substituents for alkyl and aryl groups include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for cycloalkyl groups include those listed above for alkyl and aryl, as well as alkyl.

Exemplary substituted aryls include a phenyl or naphthyl ring substituted with one or more substituents, preferably one to three substituents, independently selected from halo, hydroxy, morpholino($C_1$–$C_{20}$)alkoxy carbonyl, pyridyl ($C_1$–$C_{20}$)alkoxycarbonyl, halo ($C_1$–$C_{20}$)alkyl, $C_1$–$C_{20}$ alkyl, $C_1$–$C_{20}$ alkoxy, carboxy, $C_1$–$C_{20}$ alkocarbonyl, carbamoyl, N—($C_1$–$C_{20}$)alkylcarbamoyl, amino, $C_1$–$C_{20}$alkylamino, di($C_1$–$C_{20}$)alkylamino or a group of the formula —$(CH_2)_a$—$R_7$ where a is 1, 2, 3, 4, 5; and $R_7$ is hydroxy, $C_1$–$C_{20}$ alkoxy, carboxy, $C_1$–$C_{20}$ alkoxycarbonyl, amino, carbamoyl, $C_1$–$C_{20}$ alkylamino or di($C_1$–$C_{20}$)alkylamino, sulfonic acids, sulfonic esters, sulfonic amides, amides, esters and the like.

Another substituted alkyl is halo($C_1$–$C_{20}$)alkyl, which represents a straight or branched alkyl chain having at least one halogen atom attached to it. Exemplary halo($C_1$–$C_{20}$) alkyl groups include chloromethyl, 2-bromoethyl, 1-chloroisopropyl, 3-fluoropropyl, 2,3-dibromobutyl, 3-chloroisobutyl, trifluoromethyl, trifluoroethyl, and the like.

Another substituted alkyl is hydroxy ($C_1$–$C_{20}$)alkyl, which represents a straight or branched alkyl chain having from one to twenty carbon atoms with a hydroxy group attached to it. Exemplary hydroxy($C_1$–$C_{20}$)alkyl groups include hydroxymethyl, 2-hydroxyethyl, 3-hydroxypropyl, 2-hydroxyisopropyl, 4-hydroxybutyl, and the like.

Yet another substituted alkyl is $C_1$–$C_{20}$ alkylthio($C_1$–$C_{20}$) alkyl, which is a straight or branched $C_1$–$C_{20}$ alkyl group with a $C_1$–$C_{20}$ alkylthio group attached to it. Exemplary $C_1$–$C_{20}$ alkylthio($C_1$–$C_{20}$)alkyl groups include methylthiomethyl, ethylthiomethyl, propylthiopropyl, sec-butylthiomethyl, and the like.

Yet another exemplary substituted alkyl is heterocycle($C_1$–$C_{20}$)alkyl, which is a straight or branched alkyl chain having from one to twenty carbon atoms with a heterocycle attached to it. Exemplary heterocycle($C_1$–$C_{20}$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$–$C_{20}$)alkyl, which is a straight or branched alkyl chain having from one to twenty carbon atoms with an aryl group attached to it. Exemplary aryl($C_1$–$C_{20}$)alkyl groups include phenylmethyl, 2-phenylethyl, 3-naphthyl-propyl, 1-naphthylisopropyl, 4-phenylbutyl and the like.

The heterocycloalkyls and the heteroaryls can, for example, be substituted with 1, 2 or 3 substituents independently selected from halo, halo($C_1$–$C_{20}$)alkyl, $C_1$–$C_{20}$ alkyl, $C_1$–$C_{20}$ alkoxy, carboxy, $C_1$–$C_{20}$ alkoxycarbonyl, carbamoyl, —($C_1$–$C_{20}$)alkylcarbamoyl, amino, $C_1$–$C_{20}$alkylamino, di($C_1$–$C_{20}$)alkylamino or a group having the structure —$(CH_2)_a$—$R_7$ where a is 1, 2, 3, 4, 5 and $R_7$ is hydroxy, $C_1$–$C_{20}$ alkoxy, carboxy, $C_1$–$C_{20}$ alkoxycarbonyl, amino, carbamoyl, $C_1$–$C_{20}$alkylamino or di($C_1$–$C_{20}$)alkylamino.

Examples of substituted heterocycloalkyls include, but are not limited to, 3-N-t-butyl carboxamide decahydroisoquinolinyl and 6-N-t-butyl carboxamide octahydro-thieno[3,2-c]pyridinyl. Examples of substituted heteroaryls include, but are not limited to, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

A "pharmaceutically acceptable solvate" is intended to mean a solvate that retains the biological effectiveness and properties of the biologically active components of the inventive compounds.

Examples of pharmaceutically acceptable solvates include, but are not limited to, compounds prepared using water, isopropanol, ethanol, DMSO, and other excipients generally reffered to as GRAS ingredients.

In the case of solid formulations, it is understood that the compounds of the inventive methods may exist in different polymorph forms, such as stable and metastable crystalline forms and isotropic and amorphous forms, all of which are intended to be within the scope of the present invention.

A "pharmaceutically acceptable salt" is intended to mean those salts that retain the biological effectiveness and properties of the free acids and bases and that are not biologically or otherwise undesirable.

Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, citrates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, hydroxybutyrates, glycolates, tartrates, methanesulfoantes, propanesulfonates, naphthalene-1-sulfonates, naphthalene-2-sulfonates, and mandelates.

If a compound of the present invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, lactic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If a compound of the present invention is an acid, the desired salt may be prepared by any suitable method known to the art, including treatment of the free acid with an inorganic or organic base, such as an amine (primary, secondary or tertiary), or an alkali metal or alkaline earth metal hydroxide or the like. Illustrative examples of suitable salts include organic salts derived from amino acids such as glycine and arginine; ammonia; primary, secondary and tertiary amines; cyclic amines such as piperidine, morpholine and piperazine; and inorganic salts derived from sodium, calcium, potassium, magnesium, manganese, iron, copper, zinc, aluminum, and lithium.

In summary, there is a real need for better "shorter wavelength" absorbing photodynamic agents that do not display red absorptions, that are cleared rapidly from normal tissues, especially skin, and agents that may be used as MRI diagnostics or radiodiagnostic agents in addition to therapeutics. Additionally, as more disease indications are realized, shorter wavelength light may be equally important in other PDT applications that only require short wavelength excitation to effect a therapy. Such applications may be, for example, in hollow organ disease (for example lung cancers, barrets esophagus), or in diseases of the skin (for example psoriasis, actinic keratosis, acne vulgaris). The invention disclosed herein describes the synthesis of metallated photosensitizers having ring systems that have shown excellent efficacy in advanced animal model systems as well as preferred uptake in the target tissue, with excellent clearance characteristics and low toxicity. (See co-pending application filed on May 31, 2001 entitled "Metallotetrapyrrolic Photosensitizing Agents For Use In Photodynamic Therapy," inventors Byron C. Robinson, Ian M. Leitch, Stephanie Greene, and Steve Rychnovsky.)

The compounds of the invention are intended for use not only for effective photodynamic therapy treatment but also as MRI and radiodiagnostic diagostic agents. Such compounds may be used to diagnose, locate or treat cardiovascular disease and normal or abnormal conditions of the hematological system, lymphatic reticuloendothelial system, nervous system, endocrine and exocrine system, skeletomuscular system including bone, connective tissue, cartilage and skeletal muscle, pulmonary system, gastrointestinal system including the liver, reproductive system, skin, immune system, cardiovascular system, urinary system, ocular system, auditory or olfactory system. In particular, photoactive derivatives of porphyrins and azaporphyrins are particularly advantageous where shorter wavelengths of light are necessary to effect a photodynamic response.

EXAMPLES

Preparation of compounds according to the invention is illustrated by reference to the following non-limiting examples. It will be appreciated by persons skilled in the art with the teachings of the examples and the rest of the specification (i) how the chemistry may be applied to other peripheral groups on tetrapyrrolic ring structures that fall within the scope of this invention and (ii) that other synthetic routes may be suitable for preparation of the desired compounds.

Example 1

8,12-Diethyl-3,7,13,17-tetramethylporphyrin-2,18-dipropionylhydrazide 1.3 g of 8,12-diethyl-3,7,13,17-tetramethylporphyrin-2,18-diyl-di(methoxycarbonylpropionic acid) was modified according to H. Fischer, E. Haarer and F. Stadler, Z. Physiol. Chem. 241, 209 (1936) by treatment with hydrazine hydrate (7 mL of an 80% water solution) in pyridine (30 mL) at room temperature overnight. The solvent was removed by rotoevaporation and the solid suspended/dissolved in methanol (10 mL). Water (30 mL) was added and the methanol removed by rotary evaporation. The precipitated porphyrin was collected by filtration and dried to give the title compound. Yield: 1.25 g of a reddish-brown powder.

Example 2

Zinc 8,12-Diethyl-3,7,13,17-tetramethylporphyrin-2,18-dipropionylhydrazide

The compound produced in example 1 (100 mg) was dissolved in chloroform/methanol (80:20) and zinc acetate (200 mg) was added. The solution was refluxed until complete by UV. The solution was evaporated to dryness and redissolved in dichloromethane (50 mL). Water (100 mL) was added and the dichloromethane removed by rotary evaporation. The precipitated solid was collected by filtration, washed with water (50 mL) and dried. Yield of the title compound=110 mg.

Example 3

Platinum 8,12-Diethyl-3,7,13,17-tetramethylporphyrin-2,18-dipropionylhydrazide

Platinum 8,12-Diethyl-3,7,13,17-tetramethylporphyrin-2,18-dipropionic acid methyl ester (1.2 g) was modified according to H. Fischer, E. Haarer and F. Stadler, Z. Physiol. Chem. 241, 209 (1936) by treatment with hydrazine hydrate (7 mL of an 80% water solution) in pyridine (30 mL) at room temperature. The solution was evaporated to dryness, dissolved/suspended in methanol (10 mL) and water (30 mL) was added. The methanol was removed by rotary evaporation and the precipitated porphyrin collected by filtration and dried. Yield: 1.25 g of an orange-red powder.

Example 4

8,12-Diethyl-3,7,13,17-tetramethylporphyrin-2-{N-(6-tert-butoxycarbonylaminohexyl)propionylamide}-18-propionic acid & 8,12-Diethyl-3,7,13,17-tetramethylporphyrin-2,18-{N,N'-bis-(6-tert-butoxycarbonylaminohexyl)}dipropionylamide 8,12-Diethyl-3,7,13,17-tetramethylporphyrin-2,18-dipropionic acid (1.8 g), 1-hydroxybenzotriazole (810 mg), N-BOC-1,6-diaminohexane hydrochloride (1.52 g) and triethylamine (608 mg) is dissolved in dimethylformamide (300 mL). The solution is stirred under argon and cooled to −10° C. Dicyclohexylcarbodiimide (1.24 g) is added and the solution is stirred for 1 hr at −10° C., then left to warm to room temperature. After three hours the solution is evaporated to dryness and the residue dissolved in dichloromethane (50 mL). The solution is washed with a saturated sodium bicarbonate solution. The dichloromethane layer was dried over sodium sulfate and filtered and evaporated. The crude residue is chromatographed on silica using dichloromethane/methanol (0–10%) as eluent and the two fractions collected. The diamide is eluted first (800 mg), followed sluggishly by the mono amide title compound (1500 mg).

Example 5

8,12-Diethyl-3,7,13,17-Tetramethylporphyrin-2-{N-(6-Aminohexyl)-Propionylamide}-18-Propionic Acid The mono amide produced in example 4 (500 mg) is dissolved in 2N hydrochloric acid in glacial acetic acid (10 mL). When no more starting material could be detected, the solution is evaporated to dryness and dissolved in distilled water. A saturated sodium bicarbonate solution is added dropwise until the porphyrin precipitated. The porphyrin is collected by filtration and dried. Yield of title compound= 400 mg.

Example 6

8,12-Diethyl-3,7,13,17-Tetramethylporphyrin-2,18-{N,N'-Bis-(6-Aminohexyl}Propionylamide The di-amide produced in example 4 (500 mg) is dissolved in 2N hydrochloric acid in glacial acetic acid (10 mL) and the solution is stirred overnight. When no more starting material could be detected, the solution is evaporated to dryness and dissolved in distilled water. A saturated sodium bicarbonate solution is added dropwise until the porphyrin precipitated. The porphyrin was collected by filtration and dried. Yield of title compound=400 mg.

Example 7

Zinc 8,12-Diethyl-3,7,13,17-Tetramethylporphyrin-2-{N-(6-Aminohexyl}Propionylamide-18-Propionic Acid The porphyrin prepared in Example 5 (100 mg) is metallated as described in example 2. Yield of title compound= (100 mg).

Example 8

Zinc 8,12-Diethyl-3,7,13,17-Tetramethylporphyrin-2,18-(N,N'-Bis-(6-Aminohexyl)Propionylamide The porphyrin prepared in Example 6 (100 mg) is metallated as described in example 2. Yield of title compound= (100 mg).

Example 9

Platinum 8,12-diethyl-3,7,13,17-tetramethylporphyrin-2,18-{N,N'-bis-(6-tert-butoxycarbonylaminohexyl}dipropionylamide The porphyrin prepared in Example 2 (100 mg) is hydrolyzed in THF (50 mL) containing KOH/methanol (0.4 g; 5 mL). The solution is neutralized using acetic acid and evaporated to 10 mL. Water (50 mL) is added and the precipitated porphyrin collected by filtration and dried under vacuum. The diacid porphyrin is converted to the protected amide according to example 4, except that the solution is reacted over night. The diamide protected compound is chromatographed on silica using 5% methanol/dichloromethane as eluent. Yield of title compound=85 mg.

Example 10

Platinum 8,12-Diethyl-3,7,13,17-Tetramethylporphyrin-2,18-{N,N'-Bis-(6-Aminohexyl)}Propionylamide The porphyrin of example 9 (85 mg) is dissolved in dichloromethane (20 mL) and trifluoroacetic acid (10 mL) is added. The solution is stirred for 4 hrs, after which the solvent is removed by rotary evaporation. The compound is partially dissolved in methanol and triethylamine (0.4 mL) added. The precipitated porphyrin is collected and washed with water and dried. Yield of title compound=72 mg.

Example 11

8,12-Diethyl-3,7,13,17-Tetramethylporphyrin-2,18-{N,N'-Bis-(2-Aminoethyl}Propionylamide 8,12-diethyl-3,7,13,17-tetramethylporphyrin-2,18-propionic acid (250 mg) is suspended in dichloromethane (50 mL) and oxalyl chloride (5 mL) is added. The solution is refluxed for 2 hrs under a dry inert atmosphere and the solvent removed by rotary evaporation. The solid is redissolved in dichloromethane (dry, 20 mL) and ethylenediamine (4 mL) is added all at once. The resulting solution is stirred at room temperature for 2 hrs and the solvent removed by rotary evaporation. The solid is suspended in methanol and triethylamine (5 drops) added. The flocculated porphyrin is collected by filtration, dissolved in dichloromethane (30 mL) and chromatographed on silica using 10–15% methanol/dichloromethane (with 1% triethylamine) and the major red band collected. The solvent is removed and the porphyrin dissolved in dichloromethane and precipitated from methanol by slow evaporation of dichloromethane. The solid is collected and washed with methanol. Yield of title compound=210 mg.

Example 12

Gallium Hydroxide 8,12-Diethyl-3,7,13,17-Tetramethylporphyrin-2,18-{N,N'-Bis-(2-Aminoethyl)}Propionylamide The porphyrin prepared in Example 11 (100 mg) is metallated by refluxing a solution of the porphyrin and gallium acetylacetonate (100 mg) in acetic acid for 1.5 hrs. The solvent is removed and the solid dissolved in dichloromethane (50 mL) and washed with a saturated sodium bicarbonate solution. The organic layer is dried over sodium sulfate, filtered, evaporated to 10 ml, and hexane (10 mL) is added. The dichloromethane is slowly removed by rotary evaporation and the precipitated porphyrin collected by filtration. Yield of title compound=(100 mg).

Example 13

Indium hydroxide 8,12-diethyl-3,7,13,17-tetramethylporphyrin-2,18-{(N,N'-bis-(2-aminoethyl)}propionylamide The porphyrin prepared in Example 11 (100 mg) is metallated by refluxing a solution of the porphyrin, indium chloride (100 mg) and sodium acetate (100 mg) in acetic acid for 2 hrs. The solvent is removed and the solid dissolved in dichloromethane (50 mL) and washed with a saturated sodium bicarbonate solution. The organic layer is dried over sodium sulfate, filtered, evaporated to 10 ml, and hexane (10 mL) is added. The dichloromethane is slowly removed by rotary evaporation and the precipitated porphyrin collected by filtration. Yield of title compound=(100 mg).

Example 14

7,8,12,13-tetraethyl-12,17-dimethyl-10-azaporphyrin-2,18-di(propionic Acid Methyl Ester)

To a solution of 5,5'-dicarboxy-3,3'-di(2-methoxycarbonylethyl)-4,4'-dimethylpyrromethane (5 g) in methanol (70 mL) was added ammonium hydroxide (2.6 ml) and the solution stirred until the dipyrromethane had dissolved. 2-bromo-5-formyl-3,4-diethylpyrrole (5.3 g) and HBr (33%, 25 mL) were added. The solution was stirred at room temperature for 2 hrs after which time the solid 1,19-dibromobiladiene was filtered and dried to yield=7.2 g. A smaller amount of 1,19-dibromobiladiene (3 g) was refluxed in methanol containing sodium azide (4 g) for 4 hrs. The solvent was removed and the residue dissolved in dichloromethane and chromatographed on silica using dichloromethane as eluent. The major purple band was collected and evaporated to dryness. The compound was dissolved in dichloromethane (50 mL) and methanol (50 mL) added. The dichloromethane was removed by rotary evaporation and the precipitated azaporphyrin collected by filtration. Yield of title compound=1.7 g.

Example 15

7,8,12,13-tetraethyl-12,17-dimethyl-10-azaporphyrin-2,18-di(propanyl Hydrazide)

The azaporphyrin synthesized in example 13 (250 mg) was modified according to H. Fischer, E. Haarer and F. Stadler, Z. Physiol. Chem. 241, 209 (1936) by treatment with hydrazine hydrate (1.5 mL of an 80% water solution) in pyridine (20 mL) at room temperature. The solution was evaporated to dryness, dissolved/suspended in methanol (10 mL) and water (30 mL) was added. The methanol was removed by rotary evaporation and the precipitated porphyrin collected by filtration and dried. Yield of title compound: 250 g of a purple powder.

Example 16

Zinc 7,8,12,13-tetraethyl-12,17-dimethyl-10-azaporphyrin-2,18-di(propanyl Hydrazide)

The azaporphyrin prepared in example 14 (100 mg) was metallated according to example 2. Yield of title compound=110 mg.

Example 17

Gallium 7,8,12,13-tetraethyl-12,17-dimethyl-10-azaporphyrin-2,18-di(propanyl Hydrazide)

The azaporphyrin prepared in example 14 (100 mg) was metallated according to example 12. Yield of title compound=110 mg.

Example 18

7,8,12,13-tetraethyl-12,17-dimethyl-10-azaporphyrin-2,18-(N,N'-bis-(2-aminoethyl)propionylamide 8,12-diethyl-3,7,13,17-tetramethylporphyrin-2,18-propionic acid potassium salt (250 mg)(prepared by hydrolysis of the azaporphyrin prepared in example 14 with KOH/methanol) was converted to the title compound via the procedure described in example 11. Yield=200 mg.

Example 19

Zinc 7,8,12,13-tetraethyl-12,17-dimethyl-10-azaporphyrin-2,18-{N N'-bis-(2-aminoethyl)}propionylamide The porphyrin prepared in example 18 (100 mg) was metallated by the procedure of example 14. Yield of title compound=100 mg.

Example 20

Gallium hydroxyl 7,8,12,13-tetraethyl-12,17-dimethyl-10-azaporphyrin-2,18-(N,N'-bis-(2-aminoethyl)propionylamide The porphyrin prepared in example 18 (100 mg) was metallated by the procedure of example 12. Yield of title compound=100 mg.

Example 21

Indium hydroxyl 7,8,12,13-tetraethyl-12,17-dimethyl-10-azaporphyrin-2,18-(N,N'-bis-(2-aminoethyl)propionylamide The porphyrin prepared in example 18 (100 mg) was metallated by the procedure of example 13. Yield of title compound=100 mg.

Example 22

8,12-Diethyl-3,8,13,17-tetramethyl-2,18-bis{3,6,16-trioxo-8,11,14-tris(carboxymethyl)-17-oxa-4,5,8,11,14-pentaazanonadec-1-yl}porphyrin 806.8 mg (2 mmol) of 3-ethoxy-carbonylmethyl-6-[2-(2,6-dioxomorpholino)ethyl]-3,6-diazaoctanedioic acid (DTPA-monoethylester-monoanhydride) is suspended in 250 ml of absolute dimethylformamide. It is then covered with a layer of nitrogen, 1.0 g (10 mmol) of triethylamine and 593 mg (1 mmol) of the title compound synthesized via Example I are added, and the resulting reaction mixture is stirred for 3 days at room temperature. After the reaction is complete, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%). Yield of title compound: 1.30 g of a reddish-brown powder

Example 23

[8,12-Diethyl-3,8,13,17-tetramethyl-2,18-bis{3,6,16-trioxo-8,11,14-tris(carboxymethyl)-17-oxa-4,5,8,11,14-pentaazanonadec-1-yl}porphyrinato(2-)]-zinc The zinc porphyrin (658 mg) of example 2 is reacted as described in example 22. Yield of title compound=1.0 g

Example 24

[8,12-Diethyl-3,8,13,17-tetramethyl-2,18-bis{3,6,16-trioxo-8,11,14-tris(carboxymethyl)-17-oxa-4,5,8,11,14-pentaazanonadec-1-yl}porphyrinato(2-)]platinum The platinum porphyrin of example 3 (786 mg) is reacted as described in example 22. Yield of title compound=1.5 g

Example 25

[8,12-Diethyl-3,8,13,17-tetramethyl-2,-propionicacid-18-{3,12,22-trioxo-14,17,20-tris(carboxymethyl)-23-oxa-4,11,14,17,20-pentaazapentacosan-1-yl}porphyrin The mono-hexylamine porphyrin (663 mg) of example 5 is reacted analogously as described in example 22, except using DTPA-monoethylester-monoanhydride (404 mg) and triethylamine (0.5 g). Yield of title compound=900 mg.

Example 26

[8,12-Diethyl-3,8,13,17-tetramethyl-2,18-{3,12,22-trioxo-14,17,20-tris(carboxymethyl)-23-oxa-4,11,14,17,20-pentaazapentacosan-1-yl}porphyrin The dihexylamine porphyrin (663 mg) of example 5 is reacted as described in example 22, using DTPA-monoethylester-monoanhydride (808 mg) and triethylamine (1.0 g). Yield of title compound=1.3 g.

Example 27

[7,8,12,13-Tetraethyl-3,17-dimethyl-2,18-{3,8,18-trioxo-10,13,16-tris(carboxymethyl)-19-oxa-4,7,10,13,16-pentaazaheneicosan-1-yl}-10-azaporphyrin The diamine azaporphyrin (663 mg) of example 18 is reacted as described in example 24, using DTPA-monoethylester-monoanhydride (808 mg) and triethylamine (1.0 g). Yield of title compound=1.32 g.

Example 28

[7,8,12,13-Tetraethyl-3,17-dimethyl-2,18-{3,6,16-trioxo-8,11,14-tris(carboxymethyl)-17-oxa-4,5,8,11,14-pentaazanonadec-1-yl}-10-azaporphyrinato(2-)] zinc The zinc dihydrazide azaporphyrin (686 mg) of example 16 is reacted as described in example 22, using DTPA-monoethylester-monoanhydride (808 mg) and triethylamine (1.0 g). Yield of title compound=1.22 g.

Example 29

[7,8,12,13-Tetraethyl-3,17-dimethyl-2,18-{3,6,16-trioxo-8,11,14-tris(carboxymethyl)-17-oxa-4,5,8,11,14-pentaazanonadec-1-yl}-10-azaporphyrinato(2-)] galliumhydroxide The gallium dihydrazide azaporphyrin (707 mg) of example 17 is reacted as described in example 22, using DTPA-monoethylester-monoanhydride (808 mg) and triethylamine (1.0 g). Yield of title compound=1.31 g.

Example 30

[7,8,12,13-Tetraethyl-3,17-dimethyl-2,18-{3,8,18-trioxo-10,13,16-tris(carboxymethyl)-19-oxa-4,7,10,13,16-pentaazaheneicosan-1-yl}-10-azaporphyrinato(2-)]zinc The zinc azaporphyrin of example 19 (742 mg) is reacted as described in example 22, using DTPA-monoethylester-monoanhydride (808 mg) and triethylamine (1.0 g). Yield of title compound=1.35 g.

Example 31

7,8,12,13-tetraethyl-12,17-dimethyl-2-(3-carboxypropyl)-18-(3-methoxycarbonylpropyl)-10-azaporphyrin The dimethyl ester azaporphyrin of example 14 (1.0 g, 1.6 mmol) is dissolved in THF (200 ml) and a solution of KOH (100 mg)/MeOH (5 mL) is added. The solution is closely monitored until only a trace of starting material remains and the major product is the mono-hydrolyzed azaporphyrin. Acetic acid (107 mg) is added and the solution diluted with water (100 mL). The THF was removed by rotary evaporation and the precipitated azaporphyrins were collected and washed with methanol (20 mL) and dried. The solid was dissolved in dichloromethane containing 2% methanol and the solution is chromatographed on silica using 2% methanol/dichloromethane as eluent. The second major fraction is collected and evaporated to dryness. Yield of title compound=0.62 g.

Example 32

7,8,12,13-tetraethyl-12,17-dimethyl-2-{N-(2-aminoethyl)propionylamide}-18-(3-methoxycarbonylpropyl)-10-azaporphyrin The monoacid azaporphyrin prepared in example 30 (500 mg) is dissolved in dichloromethane (50 ml) and oxalyl chloride (5 ml) added. The solution is refluxed under dry conditions for 2 hrs and then evaporated to dryness, care being taken not to expose the crude material to moisture. The residue is dissolved in dichloromethane (50 mL, dry) and ethylene diamine (3 ml, dry) added all at once. The resulting solution is washed with a saturated sodium bicarbonate solution, followed by water and the organic layer is collected, dried over sodium sulfate, filtered and evaporated. The crude reaction mixture is chromatographed on silica using 4% methanol/dichloromethane/0.5% triethylamine as eluent, and the major fraction collected. The dichloromethane is removed by rotary evaporation and the precipitated porphyrin collected by filtration and dried. Yield of title compound=0.51 g.

Example 33

[7,8,12,13-Tetraethyl-3,17-dimethyl-2-(3-methoxycarbonylpropyl)-18-{3,8,18-trioxo-10,13,16-tris(carboxymethyl)-19-oxa-4,7,10,13,16-pentaazaheneicosan-1-yl}-10-azaporphyrin The azaporphyrin of example 32 (0.5 g, 0.76 mmol) is reacted as described in example 22, using DTPA-monoethylester-monoanhydride (404 mg) and triethylamine (0.5 g). Yield of title compound=0.8 g.

Example 34

8,12-Diethyl-3,8,13,17-tetramethyl-2,18-bis{3,6,16-trioxo-8,11,14-tris(carboxymethyl)-4,5,8,11,14-pentaazahexadecanoato-1-yl}porphyrin The ligand that is produced by Example 22 (1.0 g, 0.74 mmol) is dissolved in THF (50 mL) and water (350 mL). Sodium hydroxide solution (10 mol) is added and it is stirred overnight at room temperature. After the ester groups have been completely saponified, the THF is removed by roto-evaporation. A pH of 4 is set with concentrated hydrochloric acid. It is evaporated to the dry state in a vacuum. The residue is chromatographed on RP 18 (eluant: $H_2O$/tetrahydrofuran/gradient). Yield of title compound: 0.90 g of a reddish-brown powder.

Example 35

[8,12-Diethyl-3,8,13,17-tetramethyl-2,18-bis{3,6,16-trioxo-8,11,14-tris(carboxymethyl)-4,5,8,11,14-pentaazahexadecanoato-1-yl}porphyrinato(2-)]zinc The esters on the ligand produced by Example 23 (1.3 g, 0.885 mmol) are hydrolyzed and acidified as described in example 34. Yield of title compound=1.12 g.

Example 36

[8,12-Diethyl-3,8,13,17-tetramethyl-2,18-bis{3,6,16-trioxo-8,11,14-tris(carboxymethyl)-4,5,8,11,14-pentaazahexadecanoato-1-yl}porphyrinato(2-)] platinum The esters on the ligand produced by Example 24 (1.0 g, 0.62 mmol) are hydrolyzed and acidified as described in example 34. Yield of title compound=1.12 g.

Example 37

[7,8,12,13-Tetraethyl-3,17-dimethyl-2,18-{3,6,16-trioxo-8,11,14-tris(carboxymethyl)-4,5,8,11,14-pentaazahexadecanoato-1-yl}-10-azaporphyrinato(2-)]zinc The esters on the ligand produced in Example 28 (1.0 g, 0.69 mmol) are hydrolyzed and acidified as described in example 34. Yield of title compound=0.85 g.

Example 38

[7,8,12,13-Tetraethyl-3,17-dimethyl-2-propionic acid-18-{3,8,18-trioxo-10,13,16-tris(carboxymethyl)-4,7,10,13,16- pentaazaheneicosan-1-yl}-10-azaporphyrin The esters on the ligand produced in Example 33 (1.0 g, 1 mmol) are hydrolyzed and acidified as described in example 34. Yield of title compound=0.85 g.

Example 39

[7,8,12,13-Tetraethyl-3,17-dimethyl-2-18-{3,6,16-trioxo-8,11,14-tris(carboxymethyl)-4,5,8,11,14-pentaazahexadecanoato-1-yl}-10-azaporphyrinato(2-)]gallium chloride The esters on the ligand produced in Example 29 (1.0 g, 0.68 mmol) are hydrolyzed and acidified as described in example 34. Yield of title compound=0.85 g.

Example 40

7,8,12,13-Tetraethyl-3,17-dimethyl-2-18-{3,8,18-trioxo-10,13,16-tris(carboxymethyl)4,7,10,13,16-pentaazaheneicosan-1-yl}-10-azaporphyrin The esters on the ligand produced in Example 27 (1.0 g, 0.7 mmol) are hydrolyzed and acidified as described in example 34. Yield of title compound=0.82 g.

Example 41

Mu-[(16,16'-[zinc(II)-8,12-Diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}digadolinato(2-), disodium The ligand produced by example 35 (200 mg, 0.14 mmol) is dissolved in water (100 mL), and gadolinium chloride (74 mg, 0.28 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=260 mg.

Example 42

Mu-[(16,16'-[Platinum(II)-8,12-Diethyl-3,8,13,17-
tetramethylporphyrin-2,18-diyl]-bis[3,6,9-tris
(carboxymethyl)-11,14-dioxo-3,6,9,12,13-
pentaazahexadecanoato]}(8-)]}digadolinato(2-),
disodium The ligand produced by example 36 (200 mg, 0.13 mmol) is dissolved in water (100 mL), and gadolinium chloride (69 mg, 0.26 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=247 mg.

Example 43

{Mu-[(16,16'-[8,12-Diethyl-3,8,13,17-
tetramethylporphyrin-2,18-diyl]-bis[3,6,9-tris
(carboxymethyl)-11,14-dioxo-3,6,9,12,13-
pentaazahexadecanoato]}(8-)]}digadolinato(2-),
disodium The ligand produced by example 34 (200 mg, 0.15 mmol) is dissolved in water (100 mL), and gadolinium chloride (79 mg, 0.30 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=258 mg.

Example 44

{Mu-[(16,16'-[Zinc (11)[7,8,11,12- tetraethyl-13,17-
dimethyl-10-azaporphyrin-2,18-diyl]-bis[3,6,9-tris
(carboxymethyl)-11,14-dioxo-3,6,9,12,13-
pentaazahexadecanoato]}(8-)]}digadolinato(2-),
disodium The ligand produced by example 37 (200 mg, 0.15 mmol) is dissolved in water (100 mL), and gadolinium chloride (79 mg, 0.30 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=260 mg.

Example 45

{Mu-[18'-[Zinc (11)[7,8,11,12- tetraethyl-13,17-
dimethyl-10-azaporphyrin-2-(3-carboxypropanyl)-
18-yl]-[{3,6,9-tris(carboxymethyl)-11,16-dioxo-3,6,
9,12,15-pentaazaheneicosanato})](8-)]}digadolinato
(2-), disodium The ligand produced by example 38 (200 mg, 0.21 mmol) is dissolved in water (100 mL), and gadolinium chloride (110 mg, 0.42 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=260 mg.

Example 46

8,12- Diethyl-3,7,13,17-tetramethyl-2,18-(3-
methoxycarboxylpropyl)-5,15-diazaporphyrin This compound was prepared via the method of Neya, S., Hori, H., Imai, K., Konishi, Y. K., Suzuki, H., Shiro, Y., Lizuka, T., Funasaki, N., J. Biochem, 1997, 121, 654. The free bases of 5,5'-dibromo-3,3'-diethyldipyrromethene (2.00 g, 5.18 mmol) and 5,5'-dibromo-3,3'-di (methoxycarbonylethyl)-4,4'-dimethyldipyrromethene (2.60 g, 5.18 mmol) and sodium azide (10 g, 154 mmol) were placed in a round bottom flask containing methanol (1 L). the mixture was gently refluxed for 72 hrs. After solvent evaporation the residue was chromatographed on silica using chloroform as eluent. The title compound was eluted as the middle fraction of the three possible diazaporphyrins. The middle fraction was collected and recrystallized from dichloromethane/methanol. Yield=240 mg.

Example 47

8,12- Diethyl-3,7,13,17-tetramethyl-2,18-
dipropionylhydrazide-5,15-diazaporphyrin The compound produced by example 46 (1.0 g) was modified according to H. Fischer, E. Haarer and F. Stadler, Z. Physiol. Chem. 241, 209 (1936) by treatment with hydrazine hydrate (7 mL of an 80% water solution) in pyridine (30 mL) at room temperature overnight. The solvent was removed by rotoevaporation and the solid suspended/dissolved in methanol (10 mL). Water (30 mL) was added and the methanol removed by rotary evaporation. The precipitated porphyrin was collected by filtration and dried to give the title compound. Yield: 1.25 g of purple powder.

Example 48

8,12-Diethyl-3,7,13,17-tetramethyl-2,18-{3,6,16-
trioxo-8,11,14-tris(carboxymethyl)-17-oxa-4,5,8,11,
14-pentaazanonadec-1-yl}-5,15-diazaporphyrin The compound produced by example 47 (500 mg, 0.83 mmol) is modified according to example 22 except using DTPA-monoethylester-monoanhydride (674 mg, 1.67 mmol) and triethylamine (1.0 g) Yield of title compound= 990 mg.

Example 49

{Mu-[(16,16'-[8,12-Diethyl-3,7,13,17-tetramethyl-5,
15-diazaporphyrin-2,18-diyl]-bis[3,6,9-tris
(carboxymethyl)-11,14-dioxo-3,6,9,12,13-
pentaazahexadecanoato]}(8-)]}digadolinato(2-),
Disodium The compound produced by example 48 (200 mg, 0.148 mmol) is dissolved in water (100 mL), and gadolinium chloride (78.2 mg, 0.296 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=258 mg.

Example 50

8,13-Diethyl-3,7,12,17-tetramethyl-18-(methoxycarbonyl)-2-(3-carboxypropyl)porphyrin Rhodoporphyrin (1.0 g) was stirred in 25%HCl/H$_2$O and the reaction was closely monitored by TLC by neutralizing a small aliquot of sample taken from the solution. When no more starting material remained, the solution was neutralized by addition of sodium bicarbonate solution. The solid precipitate was dissolved in dichloromethane (200 mL) and washed with water (200 mL). The organic layer was separated and methanol (50 mL) was added. The dichloromethane was removed by rotary evaporation and the precipitated solid collected by filtration and dried. Yield of title compound=0.89 g.

Example 51

8,13-Diethyl-3,7,12,17-tetramethyl-18-(methoxycarbonyl)-2-(2-aminoethylpropylamide)porphyrin The porphyrin produced by example 50 (0.5 g) is dissolved in dichloromethane and converted to its ethylene diamine adduct via the procedure described in example 32. Yield of title compound=0.5 g.

Example 52

8,13-Diethyl-3,7,12,17-tetramethyl-18-(methoxycarbonyl)-2-{3,8,18-trioxo-10,13,16-tris(carboxymethyl)-19-oxa-4,7,10,13,16-pentaazaheneicosan-1-yl}porphyrin The porphyrin produced by example 51 (0.5 g, 0.99 mmol) is reacted as explained in described 22, using DTPA-monoethylester-monoanhydride (404 mg) and triethylamine (0.5 g). Yield of title compound=0.75 g.

Example 53

8,13-Diethyl-3,7,12,17-tetramethyl-18-(carboxylate)-2-{3,8,18-trioxo-10,13,17-tris(carboxymethyl)-4,7,10,13,17-pentaazaheneicosan-1-yl}porphyrin The esters on the porphyrin and complex produced by example 52 (0.5 g) is hydrolyzed and acidified as described in example 34. Yield of title compound=0.39 g.

Example 54

Mu-[(18'-[8,13-Diethyl-3,7,12,17-tetramethyl-18-(carboxylate)-2-yl-{11,16-dioxo-3,6,9-tris(carboxymethyl)-3,6,9,12,15-pentaazaheneicosanato}(8-)]}digadolinato(2-)porphyrin, Disodium The compound of example 53 (200 mg, 0.192 mmol) is dissolved in water (100 mL), and gadolinium chloride (51 mg, 0.192 mmol) and 2N aqueous sodium hydroxide solution are added alternately in portions, such that the pH of the reaction mixture remains between 6.8 and 7.2. After all of the gadolinium chloride is added, stirring is continued overnight at room temperature. The solvent is drawn off in a vacuum, and the residue is chromatographed on silica gel RP-18 (eluent:water/THF: 0–30%). Yield of title compound=230 mg.

Example 55

Production of a Contrast Agent for Nuclear Medicine with [111]In (General Procedure)

30 mg (0.029 mmol) of the compound produced in example 53 is dissolved in sterile, pyrogen free 0.1M citrate buffer (3 mL, pH 5.8). The solution is filtered (0.2 microns) into a multivial and mixed with 0.1 ml of a physiological salt solution containing 18.8 mCi [111]InCl$_3$. The solution is ready to use.

Example 56

Production of a Contrast Agent for Nuclear Medicine with [99m]Tc (General Procedure)

30 mg (0.029 mmol) of the compound produced in example 53 are dissolved in sterile, distilled water (1.5 mL) and mixed with sodium hydrogen sulfite (0.029 mmol). After the addition of 0.1 N HCl to pH 5.8, the solution is passed through a millipore filter (0.2 micron) into a multivial under nitrogen. After the addition of 0.5 mL of a physiological salt solution containing 96.6 mCi of $^{99m}$Tc pertechnetate, a solution ready to use is obtained.

Example 57

7,8,12,13-tetraethyl-12,17-dimethyl-2,18-bis[15,15-dimethyl-3,6,13-trioxo-8-(2-{N,N-bis[(t-butoxycarbonyl)methyl]amino}ethyl)-11-[(t-butoxycarbonyl)-methyl]14-oxa-4,5,8,11-tetraazahexadec-1-yl]-10-azaporphyrin 0.831 g (1.35 mmol) of 3,9-bis(t-butoxycarbonylmethyl)-6-carboxymethyl-3,6,9-triaza-undecanedioic acid-di-t-butyl ester, produced according to DE 19507819 (Example 1f), and 0.21 g (1.5 mmol) of 4-nitrophenol is dissolved in 10 ml of dimethylformamide, and 0.52 g (2.5 mmol) of N,N'-dicyclohexylcarbodiimide is added at ~0° C. The mixture is stirred for 3 hours at ~0° C., then overnight at room temperature. The azaporphyrin dihydrazide prepared in example 15 (209 mg (0.336 mmol) is dissolved in 50 ml of pyridine) and added in drops to the active ester solution that is thus produced, and it is stirred overnight. The solution is evaporated to dryness by rotoevaporation and the residue is chromatographed on silica gel using dichloromethane/2-propanol (20:1) as eluent. The major band is collected and evaporated to dryness. Yield of title compound=0.47 g.

Example 58

{Mu-[{13,13'-[7,8,12,13-Tetraethyl-12,17-Dimethyl-10-Azaporphyrin-2,18-Diyl]-Bis{3-Carboxymethyl-6-(2-{Nn-Bis[(Carboxy)Methyl]Amino}Ethyl)-8,11-Dioxo-3,6,9,10-Tetraazatridecanoato]}(8-)]} Digadolinato(2-), Disodium 0.5 g (0.27 mmol) of the title compound of Example 15 is dissolved in 30 ml of trifluoroacetic acid and stirred for 8 hours at room temperature. The solution is evaporated to the dry state in a vacuum. The ligand that is thus obtained is dissolved in 10 ml of water, and 0.10 g (0.279 mmol) of gadolinium oxide is added, with stirring at 60° C., and the pH is kept at 5 by adding 1 N aqueous sodium hydroxide solution as needed. The solution is filtered, and the filtrate is set at pH 7.2 with 1 N aqueous sodium hydroxide solution. Then, the filtrate is chromatographed on RP 18 (mobile solvent: gradient consisting of water/acetonitrile). Yield of title compound=0.43 g.

It will be apparent to those skilled in the art that various modifications and variations can be made in the compounds and methods of the present invention without departing from the spirit or scope of the invention. Thus, it is intended that the present invention cover the modifications and variations of this invention provided they fall within the scope of the appended claims and their equivalents.

What is claimed is:

1. A compound of formula II:

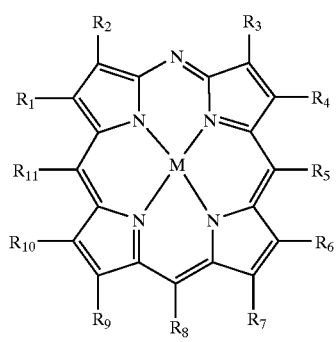

II wherein $R_1$–$R_{11}$ can be the same or different and are selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, $N(alkyl)_2$, $N(aryl)_2$, $CH=CH(aryl)$, $CH=CHCH_2N(CH_3)_2$, or a functional group of molecular weight of less than about 100,000 daltons; $CH=CHCH_2N^+(CH_3)_3A$, $CH=N(alkyl)_2A$, or $N(alkyl)_3^+A$, where A is a charge balancing ion; CN, OH, CHO, $COCH_3$, CO(alkyl), $CO_2H$, $CO_2Na$, $CO_2K$, $CH(CH_3)OH$, $CH(CH_3)O$-alkyl, $CH(CH_3)O$-alkoxy, and $CH(CH_3)O$-aryl;

$(CH_2)_nO$-alkoxy, or $(CH_2)_nO$-alkyl, where n is an integer from 0 to 8;

$C(X)_2C(X)_3$, where X is a halogen;

$CO_2R_{12}$, where $R_{12}$ is selected from a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons;

$(CH_2)_nOH$, or $(CH_2)_nOR_{13}$, where $R_{13}$ is selected from alkyl, haloalkyl, heteroalkyl, haloheteroalkyl, heterocycle, aryl, heteroaryl, a protecting group, a mono-, di-, or polyhydroxyalkyl residue, a mono-, di-, or polyhydroxyaryl residue, or a functional group of less than about 100,000 daltons, and n is an integer between 0 and 4;

$(CH_2)_nCO_2R_{14}$, $(CHX)_nCO_2R_{14}$, or $(CX_2)_nCO_2R_{14}$, where X is a halogen and $R_{14}$ is selected from H, a physiologically acceptable counter ion, a straight or branched chain C1–C20 alkyl, haloalkyl, heteroalkyl, haloheteroalky;, aryl, heteroaryl, heterocycle, a mono-, di-, or polyhydroxyalkyl residue, a mono-, di-, or polyhydroxyaryl residue, or a functional group of less than about 100,000 daltons, and n is an integer between 1 and 4;

$CONH(R_{15})$, $CONHNH(R_{15})$, $CO(R_{15})$, $CON(R_{15})_2$, $CON(R_{15})(R_{16})$, $(CH_2)_nCONH(R_{15})$, $(CH_2)_nCONHNH(R_{15})$, $(CH_2)_nCON(R_{15})_2$, $(CH_2)_nCOR_{15}$, $(CH_2)_nCON(R_{15})(R_{16})$, $(CX_2)_nCONH(R_{15})$, $(CX_2)_nCON(R_{15})_2$, $(CX_2)_nCON(R_{15})(R_{16})$ $(CX_2)_nCOR_{15}$, $(CH_2)_nCONHNH(R_{15})$, $(CX_2)_nCONHNH(R_{15})$, $(CHX)_nCONH(R_{15})$, $(CHX)_nCONHNH(R_{15})$, $(CHX)_nCON(R_{15})_2$, $(CHX)_nCON(R_{15})(R_{16})$ where X is a halogen and $R_{15}$ and $R_{16}$ can be the same or different and are selected from H, $NH_2$, straight or branched chain C1–C20 alkyl, haloalkyl, haloheteroalkyl, heteroalkyl, aryl, heteroaryl, heterocycle, a mono-, di-, or Polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100, 000 daltons, and n is an integer between 0 and 4;

$S(R_{17})$, $(CH_2)_nS(R_{17})$, $(CH_2)_nNH(R_{17})$, $(CH_2)_nNH(R_{17})$, $(CH_2)_nR_{17}$, $(CH_2)_nN(R_{17})(R_{18})$, or $(CH_2)_nN(R_{17})(R_{18})(R_{19})^+A$ where $R_{17}$, $R_{18}$ and $R_{19}$ can be the same or different and are selected from H, $NH_2$, straight or branched chain C1–C20 alkyl, haloalkyl, heteroalkyl, haloheteroalkyl, aryl, heteroaryl, heterocycle, amino acids, an amino acid ester, an amino acid amide provided —$NH(R_{17})$ is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where $R_{17}$, $R_{18}$ and $R_{19}$ together possess the atoms necessary to constitute an aromatic ring system, n is an integer between 0 and 4, and A is a physiologically acceptable counter ion;

$(CH_2)_nOPO_2OR_{20}$, $(CH_2)_nPO(OR_{20})_2$, $(CH_2)_nPO_2R_{20}$, or $(CH_2)_nPOR_{20}$ where $R_{20}$ is selected from H, a physiologically acceptable counter ion, a straight or branched chain C1–C20 alkyl, haloalkyl, heteroalkyl, haloheteroalkyl, aryl or heteroaryl, heterocycle, amino acids and salts, esters, or amides thereof, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

$(CH_2)_nNHCOR_{21}$, or $(CH_2)_nNHNHCOR_{21}$, where $R_{21}$ is selected from a straight or branched chain C1–C20 alkyl, haloalkyl, heteroalkyl, haloheteroalkyl, aryl, heteroaryl, heterocycle, amino acids and salts, esters, or amides thereof, or a functional group of less than about 100,000 daltons, and n is an integer between 0 and 4;

$SO_3R_{22}$, $SO_2NHR_{22}$, $SO_2N(R_{22})_2$, $SO_2NHNHR_{22}$ or $SO_2R_{22}$, where $R_{22}$ is select H, a physiologically acceptable counter ion, a straight or branched chain C1–C20 alkyl, haloalkyl, heteroalkyl, haloheteroalkyl, aryl or heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, and $NHR_{22}$ can be an amino acid residue, an amino acid salt, an amino acid ester residue, an amino acid amide residue, or a functional group of less than about 100,000 daltons;

Aryl or substituted aryl, which may bear one or more substituents with a molecular weight of less than or equal to about 100,000 daltons;

$R_1-R_2$, $R_3-R_4$, $R_6-R_7$, $R_9-R_{10}$, $R_4-R_5$, $R_5-R_6$, $R_7-R_8$, $R_8-R_9$, $R_{10}-R_{11}$, or $R_{11}-R_1$, may also possess the atoms necessary to form ring systems, which themselves may possess heteroatoms that may bear one or more functional groups of molecular weight equal to or less than about 100,000 daltons;

with the proviso that at least one of the $R_1-R_{11}$ groups is linked via an organic group that has as part or all of its structure a group Q, which is an amine, an ester, an ether or an amide link, to a complexing agent of general formula IIa, IIb, IIc, IId, IIe:

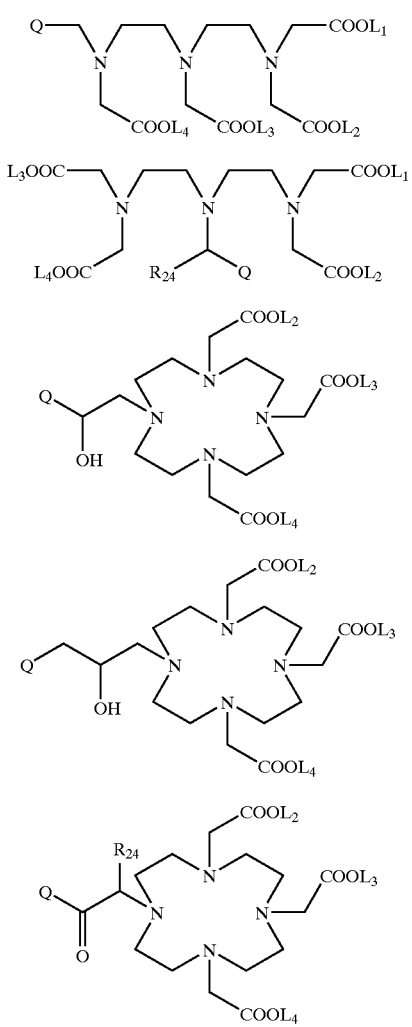

wherein $R_{24}$ is selected from a hydrogen, a straight or branched chain $C_1-C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxyhic acid groups that are not required for complexing are optionally present as salts with physiologically compatible inorganic cations, or organic cations, or as esters or amides; and wherein M is 2H or a diamagnetic or paramagnetic photoactive metal ion selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, and $Mg^{2+}$.

2. A method of using the compound of claim 1 comprising administering the compound to a patient and, after a period of time, imaging targeted tissue of the patient through MRI or radio-diagnostic imaging.

3. A method of using the compound of claim 1 comprising administering the compound to a patient and, after a period of time, irradiating targeted tissue of the patient with an energy source that excites the compound thereby producing a desired therapeutic response in the target tissue.

4. A method of using the compound of claim 1 comprising administering the compound to a patient and, after a period of time, imaging targeted tissue of the patient through MRI or radio-diagnostic imaging then, after a second period of time, irradiating the targeted tissue with an energy source that excites the compound thereby producing a desired therapeutic response in the target tissue.

5. A method for the detection or treatment of tissue comprising administering to a patient a therapeutic amount of the compound of claim 1 locally, systemically, intramuscularly or interperitoneally and irradiating said compound with energy at a wavelength able to excite the molecule, such that a desired therapeutic effect is observed, whereby said tissue belongs to the hematological system, lymphatic reticuloendothelial system, nervous system, endocrine and exocrine system, skeletomuscular system, skin, pulmonary system, gastrointestinal, reproductive system, immune system, cardiovascular system, urinary system, auditory or olfactory system.

6. The method of claim 2, wherein said method is for diagnosing disorders in a vessel wall, tissue adjoining the vessel wall, or material attached to the vessel wall of a coronary, carotid or peripheral vasculature.

7. The method of claim 6 wherein said vessel is an artery or a vein.

8. The method of claim 2 wherein the tissue is atherosclerosis, restenosis or graft disease.

9. The method of claim 3 wherein the tissue is atherosclerosis, restenosis or graft disease.

10. The method of claim 4 wherein the tissue is atherosclerosis, restenosis or graft disease.

11. The method of claim 5 wherein the tissue is atherosclerosis, restenosis or graft disease.

12. The method of claim 4 wherein the therapy is selected from ablation, reduction and stabilization of vessel wall plaque.

13. The method of claim 4 wherein said energy source is selected from light, ultrasound, magnetic force, and electromagnetic radiation in the UV/visible electromagnetic spectrum or near infrared.

14. The method of claim 4 wherein said administration of the compound is prior to, concomitant with, or subsequent to adjunctive interventions, diagnostics or therapies.

15. The method of claim 4 wherein said administration is a single bolus or plurality of doses administered to the patient.

16. A compound of formula IIA:

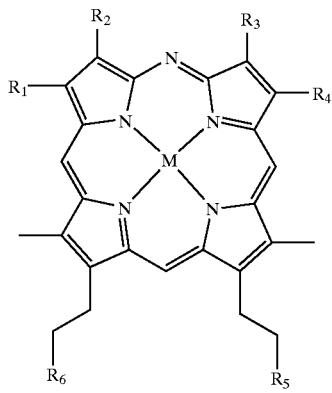

wherein $R_1$–$R_6$ can be the same or different and are selected from: H, halide, substituted or unsubstituted alkyl, heteroalkyl, haloalkyl, heterohaloalkyl, cyclic alkyl, aryl, substituted aryl, alkenyl, substituted alkenyl, alkynyl, substituted alkynyl, amide, ester, ether, polyether, alkoxy group, aryloxy group, haloalkoxy group, amino group, alkylcarbonyloxy group, alkoxycarbonyl group, aryloxycarbonyl group, azo group, arylcarbonyloxy group, alkoxycarbonyloxy group, aryloxycarbonyloxy group, sulfinyl group, sulfonyl group, silil group, carbamoyl group, heterocyclic group, nitro group, nitroso group, formyloxy group, isocyano group, cyanate group, isocyanate group, thiocyanate group, isothiocyanate group, N(alkyl)$_2$, N(aryl)$_2$, CH=CH(aryl), CH=CHCH$_2$N(CH$_3$)$_2$, or a functional group of molecular weight of less than about 100,000 daltons; CH=CHCH$_2$N$^+$(CH$_3$)$_3$A, CH=N(alkyl)$_2$A, or N(alkyl)$_3^+$A, where A is a charge balancing ion; CN, OH, CHO, COCH$_3$, CO(alkyl), CO$_2$H, CO$_2$Na, CO$_2$K, CH(CH$_3$)OH, CH(CH$_3$)O-alkyl, CH(CH$_3$)O-alkoxy, or CH(CH$_3$)O-aryl;

(CH$_2$)$_n$O-alkoxy, or (CH$_2$)$_n$O-alkyl, where n is an integer from 0 to 8;

C(X)$_2$C(X)$_3$, where X is a halogen;

CO$_2$R$_7$, where R$_7$ is selected from a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, or a functional group of less than about 100,000 daltons;

(CH$_2$)$_n$OH, or (CH$_2$)$_n$OR$_8$, where R$_8$ is selected from alkyl, haloalkyl, heteroalkyl, haloheteroalkyl, aryl, heteroaryl, heterocycle, a protecting group, a mono-, di-, or polyhydroxyalkyl residue, a mono-, di-, or polyhydroxyaryl residue, or a functional group of less than about 100,000 daltons, and n is an integer between 0 and 4;

(CH$_2$)$_n$CO$_2$R$_9$, (CHX)$_n$CO$_2$R$_9$, or (CX$_2$)$_n$CO$_2$R$_9$, where X is a halogen and R$_9$ is selected from H, a physiologically acceptable counter ion, a straight or branched chain C1–C20 alkyl, haloalkyl, heteroalkyl, haloheteroalkyl, heterocycle, aryl, heteroaryl, a mono-, di-, or polyhydroxyalkyl residue, a mono-, di-, or polyhydroxyaryl residue, or a functional group of less than about 100,000 daltons, and n is an integer between 1 and 4;

CONH(R$_{10}$), CONHNH(R$_{10}$), CO(R$_{10}$), CON(R$_{10}$)$_2$, CON(R$_{10}$)(R$_{11}$), (CH$_2$)$_n$CONH(R$_{10}$), (CH$_2$)$_n$CONHNH(R$_{10}$), (CH$_2$)$_n$CON(R$_{10}$)$_2$, (CH$_2$)$_n$COR$_{10}$, (CH$_2$)$_n$CON(R$_{10}$)(R$_{11}$), (CX$_2$)$_n$CONH(R$_{10}$), (CX$_2$)$_n$CON(R$_{10}$)$_2$, (CX$_2$)$_n$CON(R$_{10}$)(R$_{11}$), (CX$_2$)$_n$COR$_{10}$, (CH$_2$)$_n$CONHNH(R$_{10}$), (CX$_2$)$_n$CONHNH(R$_{10}$), (CHX)$_n$CONH(R$_{10}$), (CHX)$_n$CONHNH(R$_{10}$), (CHX)$_n$CON(R$_{10}$)$_2$, or (CHX)$_n$CON(R$_{10}$)(R$_{11}$), where X is a halogen and R$_{10}$ and R$_{11}$ can be the same or different and are selected from H, NH$_2$, straight or branched chain C1–C20 alkyl, haloalkyl, haloheteroalkyl, heteroalkyl, aryl, heteroaryl, heterocycle, a mono-, di-, or polyhydroxyalkyl residue, a mono-, di-, or polyhydroxyaryl residue, an amino acid, an amino acid salt, an amino acid ester, an amino acid amide, a mono-, di-, or polyetheralkyl residue, a mono-, di-, or polyetheraryl residue, or a functional group of less than about 100,000 daltons, and n is an integer between 0 and 4;

S(R$_{12}$), (CH$_2$)$_n$S(R$_{12}$), (CH$_2$)$_n$NH(R$_{12}$), (CH$_2$)$_n$NHNH(R$_{12}$), (CH$_2$)$_n$N(R$_{12}$)$_2$, (CH$_2$)$_n$N(R$_{12}$)(R$_{13}$), or (CH$_2$)$_n$N(R$_{12}$)(R$_{13}$)(R$_{14}$)$^+$A, where R$_{12}$, R$_{13}$ and R$_{14}$ can be the same or different and are selected from H, NH$_2$, straight or branched chain C1–C20 alkyl, haloalkyl, heteroalkyl, haloheteroalkyl, aryl, heteroaryl, heterocycle, amino acids, an amino acid ester, or an amino acid amide provided —NH(R$_{13}$) is part of the amino acid, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, or where R$_{12}$, R$_{13}$ and R$_{14}$ together possess the atoms necessary to constitute an aromatic ring system, n is an integer between 0 and 4, and A is a physiologically acceptable counter ion;

(CH$_2$)$_n$OPO$_2$OR$_{15}$, (CH$_2$)$_n$PO(OR$_{15}$)$_2$, (CH$_2$)$_n$PO$_2$R$_{15}$, or (CH$_2$)$_n$POR$_{15}$ where R$_{15}$ is selected from H, a physiologically acceptable counter ion, a straight or branched chain C1–C20 alkyl, haloalkyl, heteroalkyl, haloheteroalkyl, aryl or heteroaryl, heterocycle, amino acids and salts, esters, or amides thereof, a mono-, di-, or polyhydroxyalkyl residue, a mono-, di-, or polyhydroxyaryl residue, a mono-, di-, or polyetheralkyl residue, a mono-, di-, or polyetheraryl residue, or a functional group of less than about 100,000 daltons, and n is an integer between 0 and 4;

(CH$_2$)$_n$NHCOR$_{16}$, or (CH$_2$)$_n$NHNHCOR$_{16}$, where R$_{16}$ is selected from a straight or branched chain C1–C20 alkyl, haloalkyl, heteroalkyl, haloheteroalkyl, aryl, heteroaryl, heterocycle, amino acids and salts, esters, or amides thereof, or a functional group of less than about 100,000 daltons, and n is an integer between 0 and 4;

SO$_3$R$_{17}$, SO$_2$NHR$_{17}$, SO$_2$N(R$_{17}$)$_2$, SO$_2$NHNHR$_{17}$ or SO$_2$R$_{17}$, where R$_{17}$ is select H, a physiologically acceptable counter ion, a straight or branched chain C1–C20 alkyl, haloalkyl, heteroalkyl, haloheteroalkyl, aryl, heteroaryl, heterocycle, a mono-, di-, or polyhydroxyalkyl residue, a mono-, di-, or polyhydroxyaryl residue, a mono-, di-, or polyetheralkyl residue, a mono-, di-, or polyetheraryl residue, a functional group of less than about 100,000 daltons, and NHR$_{17}$ can be an amino acid residue, an amino acid salt, an amino acid ester residue, an amino acid amide residue;

Aryl or substituted aryl, which may bear one or more substituents with a molecular weight of less than or equal to about 100,000 daltons; and R$_1$—R$_2$, and R$_3$—R$_4$ may also possess the atoms necessary to form ring systems, which themselves may possess heteroatoms that may bear one or more functional groups of molecular weight equal to or less than about 100,000 daltons;

with the proviso that at least one of the $R_1$–$R_4$ groups is linked via an organic group that has as part or all of its structure a group Q, which is an amine, an ester, an ether or an amide link, to a complexing agent of general formula IIa, IIb, IIc, IId, IIe:

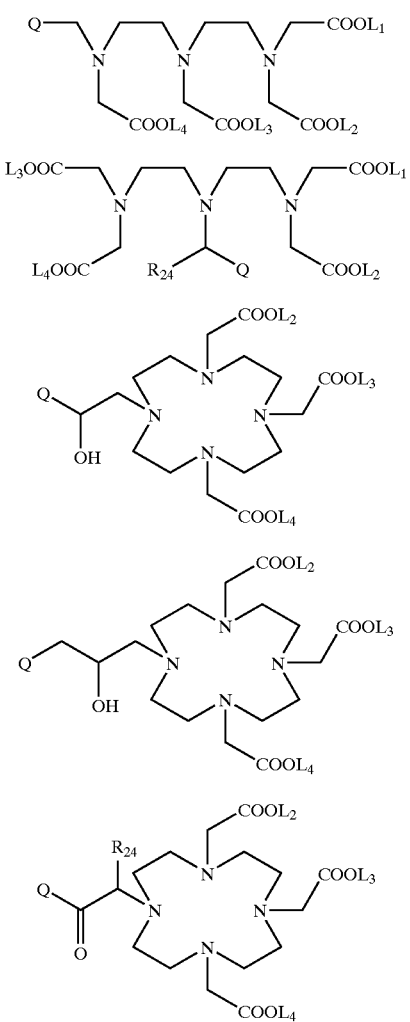

wherein $R_{24}$ is selected from a hydrogen, a straight or branched chain $C_1$–$C_7$ alkyl group, a phenyl or benzyl group; $L_1$, $L_2$, $L_3$, $L_4$, independently of one another, are selected from a hydrogen atom or a metal ion equivalent of an element of the atomic numbers 20–32, 37–39, 42–51, or 57–83, which may be radioactive, provided that at least two of $L_1$, $L_2$, $L_3$ and $L_4$ are metal ion equivalents, that other anions are present to compensate for optionally present charges on the porphyrin, and free carboxylic acid groups that are not required for complexing are optionally present as salts with physiologically compatible inorganic cations, or organic cations, or as esters or amides; and wherein M is 2H or a diamagnetic or paramagnetic photoactive metal ion selected from $Ga^{3+}$, $Pt^{2+}$, $Pd^{2+}$, $Sn^{4+}$, $In^{3+}$, $Ge^{4+}$, $Si^{4+}$, $Al^{3+}$, $Zn^{2+}$, and $Mg^{2+}$.

17. A method of using the compound of claim 16 comprising administering the compound to a patient and, after a period of time, imaging targeted tissue of the patient through MRI or radio-diagnostic imaging.

18. A method of using the compound of claim 16 comprising administering the compound to a patient and, after a period of time, irradiating targeted tissue of the patient with an energy source that excites the compound thereby producing a desired therapeutic response in the target tissue.

19. A method of using the compound of claim 16 comprising administering the compound to a patient and, after a period of time, imaging targeted tissue of the patient through MRI or radio-diagnostic imaging then, after a second period of time, irradiating the targeted tissue with an energy source that excites the compound thereby producing a desired therapeutic response in the target tissue.

20. A method for the detection or treatment of tissue comprising administering to a patient a therapeutic amount of the compound of claim 16 locally, systemically, intramuscularly or interperitoneally and irradiating said compound with energy at a wavelength able to excite the molecule, such that a desired therapeutic effect is observed, whereby said tissue belongs to the hematological system, lymphatic reticuloendothelial system, nervous system, endocrine and exocrine system, skeletomuscular system, skin, pulmonary system, gastrointestinal, reproductive system, immune system, cardiovascular system, urinary system, auditory or olfactory system.

21. The method of claim 17, wherein said method is for diagnosing disorders in a vessel wall, tissue adjoining the vessel wall, or material attached to the vessel wall of a coronary, carotid or peripheral vasculature.

22. The method of claim 21 wherein said vessel is an artery or a vein.

23. The method of claim 17 wherein the tissue is atherosclerosis, restenosis or graft disease.

24. The method of claim 18 wherein the tissue is atherosclerosis, restenosis or graft disease.

25. The method of claim 19 wherein the tissue is atherosclerosis, restenosis or graft disease.

26. The method of claim 20 wherein the tissue is atherosclerosis, restenosis or graft disease.

27. The method of claim 19 wherein the therapy is selected from ablation, reduction and stabilization of vessel wall plaque.

28. The method of claim 19 wherein said energy source is selected from light, ultrasound, magnetic force, and electromagnetic radiation in the UV/visible electromagnetic spectrum or near infrared.

29. The method of claim 19 wherein said administration of the compound is prior to, concomitant with, or subsequent to adjunctive interventions, diagnostics or therapies.

30. The method of claim 19 wherein said administration is a single bolus or plurality of doses administered to the patient.

* * * * *

UNITED STATES PATENT AND TRADEMARK OFFICE
CERTIFICATE OF CORRECTION

PATENT NO. : 6,906,050 B2  Page 1 of 1
APPLICATION NO. : 10/159580
DATED : June 14, 2005
INVENTOR(S) : Byron C. Robinson It is certified that error appears in the above-identified patent and that said Letters Patent is hereby corrected as shown below:

Claim 1, col. 79, lines 46-47, "CH=N(alkyl)$_2$A" should read -- CH=N$^+$(alkyl)$_2$A --.

Claim 1, col. 80, line 5, "haloheteroalky:," should read -- haloheteroalkyl, --.

Claim 1, col. 82, line 2, "carboxyhic" should read -- carboxylic --.

Claim 16, col. 83, lines 36-37 "CH=N(alkyl)$_2$A" should read -- CH=N$^+$(alkyl)$_2$A --.

Claim 16, col. 84, line 53, "is select H" should read -- is selected from H --.

Signed and Sealed this

Nineteenth Day of September, 2006

JON W. DUDAS
*Director of the United States Patent and Trademark Office*